US012630595B2

(12) United States Patent
Iglesias et al.

(10) Patent No.: US 12,630,595 B2
(45) Date of Patent: **\*May 19, 2026**

(54) REGULATORY NUCLEIC ACID SEQUENCES

(71) Applicant: ASKLEPIOS BIOPHARMACEUTICAL, INC., Research Triangle Park, NC (US)

(72) Inventors: Juan Manuel Iglesias, Midlothian (GB); Jorge Omar Yanez-Cuna, Midlothian (GB); Nicolle Kippen, Midlothian (GB); Michael Roberts, Midlothian (GB)

(73) Assignee: ASKBIO INC.

( * ) Notice: Subject to any disclaimer, the term of this patent is extended or adjusted under 35 U.S.C. 154(b) by 1133 days.

This patent is subject to a terminal disclaimer.

(21) Appl. No.: 17/295,210

(22) PCT Filed: Nov. 19, 2019

(86) PCT No.: PCT/GB2019/053268

§ 371 (c)(1),
(2) Date: May 19, 2021

(87) PCT Pub. No.: WO2020/104783

PCT Pub. Date: May 28, 2020

(65) Prior Publication Data

US 2021/0388347 A1 Dec. 16, 2021

(30) Foreign Application Priority Data

Nov. 19, 2018 (GB) ..................................... 1818816

(51) Int. Cl.
| | |
|---|---|
| *C07K 14/47* | (2006.01) |
| *A61K 48/00* | (2006.01) |
| *C12N 5/071* | (2010.01) |
| *C12N 15/86* | (2006.01) |

(52) U.S. Cl.
CPC ...... *C07K 14/4705* (2013.01); *A61K 48/0058* (2013.01); *C12N 5/067* (2013.01); *C12N 15/86* (2013.01); *C12N 2830/008* (2013.01)

(58) Field of Classification Search
CPC .............. C07K 14/4705; C07K 14/435; A61K 48/0058; C12N 5/067; C12N 15/86; C12N 2830/008
See application file for complete search history.

(56) References Cited

U.S. PATENT DOCUMENTS

| | | | |
|---|---|---|---|
| 5,721,096 A | 2/1998 | Karathanasis et al. | |
| 6,521,225 B1 | 2/2003 | Srivastava et al. | |
| 7,351,813 B2 | 4/2008 | Miao et al. | |
| 9,617,548 B2 | 4/2017 | Chuah et al. | |
| 11,161,890 B2 | 11/2021 | Wong | |
| 11,535,866 B2 | 12/2022 | Wilson et al. | |
| 2002/0076798 A1 | 6/2002 | Miao et al. | |

| | | | |
|---|---|---|---|
| 2003/0077812 A1 | 4/2003 | McArthur et al. | |
| 2003/0124530 A1 | 7/2003 | Edwards et al. | |
| 2011/0065100 A1 | 3/2011 | Aldred et al. | |
| 2020/0199582 A1 | 6/2020 | Roberts | |

FOREIGN PATENT DOCUMENTS

| | | |
|---|---|---|
| CN | 102628041 A | 8/2012 |
| CN | 102634515 A | 8/2012 |
| CN | 108588097 A | 9/2018 |
| JP | 2001500376 A | 1/2001 |
| JP | 2004500880 A | 1/2004 |
| JP | 2011517955 A | 6/2011 |
| JP | 2014506456 A | 3/2014 |
| WO | 2009130208 A1 | 10/2009 |
| WO | 2016146757 A1 | 9/2016 |
| WO | 2017180857 A1 | 10/2017 |
| WO | 2018215613 A1 | 11/2018 |

OTHER PUBLICATIONS

Li et al. "A small regulatory element from chromosome 19 enhances liver-specific gene expression." Gene Therapy 16(1): 43-51 (2009).
Database accession No. ABK29876. "Wild type hepatitis B virus (HBV) X promoter." Geneseq Apr. 23, 2002 (Apr. 23, 2002), retrieved from EBI accession No. GSN: ABK29876.
Database accession No. ABX09226. "Arteriosclerosis-detecting probe from PROC #4." Geneseq Jan. 22, 2003 (Jan. 22, 2003), retrieved from EBI accession No. GSN: ABX09226.
Database accession No. ADE80458. "Duplex oligonucleotide for DNA protein binding assay seq id 428." Geneseq Jan. 29, 2004 (Jan. 29, 2004), retrieved from EBI accession No. GSN: ADE80458.
Database accession No. BDS84014. "Micro RNA mutation detecting probe H2." Geneseq May 18, 2017 (May 18, 2017), retrieved from EBI accession No. GSN: BDS84014.
Database accession No. BFJ18268. "HBV enhancer DNA sequence (ENHL)." Geneseq Jul. 26, 2018 (Jul. 26, 2018), retrieved from EBI accession No. GSN: BFJ18268.
Nair et al. "Computationally designed liver-specific transcriptional modules and hyperactive factor IX improve hepatic gene therapy." Blood, The Journal of the American Society of Hematology 123(20): 3195-3199 (2014).

(Continued)

*Primary Examiner* — J. E. Angell
(74) *Attorney, Agent, or Firm* — NIXON PEABODY LLP; Ronald I. Eisenstein; Jeanne N. Jodoin

(57) ABSTRACT

The present invention relates to regulatory nucleic acid sequences, in particular liver-specific cis-regulatory elements, cis-regulatory modules, promoters and other such nucleic acid sequences, that are capable of enhancing liver-specific expression of genes. The invention also relates to expression constructs, vectors and cells comprising such liver-specific regulatory nucleic acid sequences, and to methods of their use. The liver-specific regulatory nucleic acid sequences are of particular utility for gene therapy applications, but also find utility in other areas such as bioprocessing and biotechnology.

17 Claims, 7 Drawing Sheets

Specification includes a Sequence Listing.

(56) References Cited

OTHER PUBLICATIONS

Rouet et al. "A potent enhancer made of clustered liver-specific elements in the transcription control sequences of human alpha 1-microglobulin/bikunin gene." Journal of Biological Chemistry 267(29): 20765-20773 (1992).

Lv et al. "Progress in the molecular biology of apolipoprotein CI." Chinese Journal of Arteriosclerosis, vol. 6, Issue 4: 356-362 (1998) [English Translation Provided].

Fig. 3

REGULATORY NUCLEIC ACID SEQUENCES

CROSS REFERENCE TO RELATED APPLICATIONS

This Application is a 35 U.S.C. § 371 National Phase Entry of International Patent Application No. PCT/GB2019/053268 filed Nov. 19, 2019, which designates the U.S. and claims benefit of foreign priority under 35 U.S.C. § 119(b) of GB Application Number 1818816.9 filed Nov. 19, 2018, the contents of which are incorporated herein in their entireties by reference.

SEQUENCE LISTING

The instant application contains a Sequence Listing which has been submitted electronically in ASCII format and is hereby incorporated by reference in its entirety. Said ASCII copy, created on May 18, 2021, is named Sequence_listing_7878087.txt and is 34,260 bytes in size.

FIELD OF THE INVENTION

The present invention relates to regulatory nucleic acid sequences, in particular liver-specific cis-regulatory elements, cis-regulatory modules, promoters and other such nucleic acid sequences, that are capable of enhancing liver-specific expression of genes. The invention also relates to expression constructs, vectors and cells comprising such liver-specific regulatory nucleic acid sequences, and to methods of their use. The liver-specific regulatory nucleic acid sequences are of particular utility for gene therapy applications, but also find utility in other areas such as bioprocessing and biotechnology.

BACKGROUND OF THE INVENTION

The following discussion is provided to aid the reader in understanding the disclosure and does not constitute any admission as to the contents or relevance of the prior art.

In many areas, including gene therapy, it is desirable to provide regulatory nucleic acid sequences that are capable of driving expression of a gene to produce a protein or nucleic acid expression product within a desired cell, tissue or organ.

Expression in the liver is of particular interest as it is involved in a wide range of essential functions in the body, including the synthesis of many proteins involved in metabolism, haemostasis, and protection against infection. Given that many diseases are linked to disruption of gene expression in the liver, there is a significant interest in developing gene therapy strategies that allow expression of a transgene in the liver to produce a therapeutic expression product. Examples of diseases of the liver associated with abnormal expression of genes include haemophilia (including haemophilia A or B), familial hypercholesterolemia, ornithine transcarbamylase deficiency, α-antitrypsin deficiency, hepatitis virus infection, non-viral hepatitis, liver cancer, and various other liver diseases (such as non-alcoholic fatty liver disease (NAFLD), and alcohol-related liver disease (ARLD).

A significant challenge in using gene therapy to treat liver diseases is the ability to provide liver-specific (also known as hepato-specific) therapeutic gene expression. It is known to target of mammalian hepatocytes by injecting DNA or viral vectors into the liver parenchyma, hepatic artery or portal vein. Adenoviral vectors have also been reported to primarily target the liver in mice. However, they also infect other tissues, in particular lung and skeletal muscle, leading to "off-target" effects. Some forms of adeno-associated viral vectors (AAV) or lentiviral vectors preferentially transduce hepatocytes, but off-target effects do again arise.

It is therefore desirable to provide systems to regulate gene expression in a liver-specific manner. Ideally, such systems are highly-specific to the liver (thereby avoiding or minimising off-target expression in non-target tissues) and are also powerful, i.e. they drive high expression levels in the liver. The use of cis-acting regulatory elements has been proposed to provide both specificity and activity. Typically, this concerns cis-regulatory enhancer sequences, i.e. nucleic acid sequences that act in cis to increase the activity of a promoter. Enhancers are typically active regardless of their orientation, and they can act over distances of up to several kilobases away from the promoter in some cases, though they typically also act when much closer to the promoter.

Various enhancer sequences for liver-specific expression of genes have been described in the literature. WO95/011308 and WO01/098482 describe a gene therapy vector comprising a hepatocyte-specific apolipoprotein E-Hepatocyte Control Region enhancer linked to a promoter and a transgene. Other liver-specific constructs have also been proposed in the literature, e.g. with the AAT promoter and the albumin or hepatitis B enhancers, or the alcohol dehydrogenase 6 (ADH6) basal promoter linked to two tandem copies of the apolipoprotein E enhancer element. WO2009/130208 describes various liver-specific regulatory elements, which are described as advantageous because of their comparatively short length. Regulatory sequences of short length are desirable to minimise the proportion of a gene therapy vector taken up by regulatory sequences; this is particularly important for gene therapy vectors with limited capacity (payload) such as AAV vectors.

There remains a need in the art for regulatory nucleic acids which are able to drive liver-specific gene expression. In particular, there is a need for liver-specific cis-regulatory enhancer elements, and for liver-specific cis-regulatory modules comprising such elements, which can be incorporated in expression constructs, promoters and vectors for liver-specific expression desired gene (e.g. a therapeutic transgene in a gene therapy context).

SUMMARY OF THE INVENTION

In a first aspect of the invention, there is provided a synthetic liver-specific cis-regulatory enhancer element comprising a sequence according to SEQ ID NO: 2 (also referred to herein as V1 or LVR_CRE0077_V1) or SEQ ID NO: 3 (also referred to herein as V2 or LVR_CRE0078_V2), or a functional variant of SEQ ID NO: 2 or SEQ ID NO: 3.

The present inventors have identified that the cis-regulatory enhancer elements referred to herein as V1 and V2 represent versatile and highly active (powerful) liver-specific enhancers of gene expression. V1 or V2, or functional variants thereof, can be combined with other regulatory sequences (e.g. other cis-regulatory enhancer elements, a minimal and/or proximal promoter) to confer or potentiate liver-specific expression of an operably linked gene. Thus, V1 and/or V2 can be used as enhancer sequences in a broad range of synthetic promoters to enhance liver-specific gene expression.

It is generally preferred that the functional variant of SEQ ID NO: 2 comprises transcription factor binding sites (TFBS) for the same transcription factors (TF) as SEQ ID NO: 2. The TFBS present in SEQ ID NO: 2, listed in order (5' to 3'), are: HNF3, HNF3, HNF1, HNF3, and HNF3. A functional variant of SEQ ID NO: 2 thus preferably comprises all of these TFBS. Preferably, the TFBS are present in the same order that they are present in SEQ ID NO: 2, i.e. in the order HNF3, HNF3, HNF1, HNF3, then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some preferred embodiments the functional variant of SEQ ID NO: 2 comprises the following TFBS sequences: AGCAAATATTT (HNF3) (SEQ ID NO: 49), AAATAT-TTGTGG (HNF3) (SEQ ID NO: 50), GGTTATGGAT-TAACT (HNF1) (SEQ ID NO: 51), CTGTTTGCCC (HNF3) (SEQ ID NO: 52), CTATTTGCCC (HNF3) (SEQ ID NO: 53), sequences complementary thereto, or functional variants of these TFBS sequences that maintain the ability to bind to bind to their respective TF (see Table 6 for further details). These may be present in the same order as SEQ ID NO: 2, i.e. the order in which they are set out above. It is well-known in the art that there is sequence variability associated with TFBS, and that for a given TFBS there is typically a consensus sequence, from which some degree of deviation is typically present. (Details of TF consensus sequences and associated positional weight matrices can be found in, for example, the Jaspar or Transfac databases http://jaspar.genereg.net/and http://gene-regulation.com/pub/databases.html)

In some embodiments of the invention, the functional variant of SEQ ID NO: 2 comprises the sequence: AGCAAATATTTGTGGTTATGGATTAACT-Na-CTGTTTGCCC-Nb-CTATTTGCCC (SEQ ID NO: 65), or a sequence that is at least 60%, 70%, 80%, 90%, 95% or 99% identical thereto, wherein Na and Nb each represent an optional spacer sequence. Where present, the spacer sequences Na and Nb are suitably from 0 to 10 nucleotides in length. Optionally, Na is from 2 to 8 nucleotides in length, preferably from 3 to 6 nucleotides in length, and more preferably 4 nucleotides in length. Optionally Nb is from 2 to 8 nucleotides in length, preferably from 2 to 6 nucleotides in length, and more preferably 3 nucleotides in length.

In some embodiments of the invention, the functional variant of SEQ ID NO: 2 comprises a sequence that is at least 60% identical to SEQ ID NO: 2, more preferably at least 70%, 80%, 90%, 95% or 99% identical to SEQ ID NO: 2. Additionally or alternatively, a functional variant of SEQ ID NO: 2 suitably comprises a sequence which hybridises under stringent conditions to SEQ ID NO: 2.

In some embodiments of the invention the cis-regulatory enhancer element consists of SEQ ID No: 2 or a functional variant thereof.

It will be noted that the synthetic liver-specific cis-regulatory enhancer element comprising a sequence according to SEQ ID NO: 2 or a functional variant thereof can be provided on either strand of a double stranded polynucleotide and can be provided in either orientation. As such, complementary and reverse complementary sequences of SEQ ID NO: 2 or a functional variant thereof fall within the scope of the invention. Single stranded nucleic acids comprising the sequence according to SEQ ID NO: 2 or a functional variant thereof also fall within the scope of the invention.

In some embodiments it is preferred that the functional variant of SEQ ID NO: 3 comprises transcription factor binding sites (TFBS) for the same transcription factors (TF) as SEQ ID NO: 3. The TFBS present in SEQ ID NO: 3, listed in order, are: HNF4, c/EBP, HNF3, and HNF3. The functional variant of SEQ ID NO: 3 thus preferably comprises these TFBS. Preferably, they are present in the same order that they are present in SEQ ID NO: 3, i.e. in the order HNF4, c/EBP, HNF3, and HNF3. When the cis-regulatory element is associated with a promoter and gene, this order is preferably considered in an upstream to downstream direction (i.e. in the direction from distal from the transcription start site (TSS) to proximal to the TSS). In some embodiments the TFBS overlap, provided they remain functional, i.e. overlapping sequences are both able to bind their respective TFs.

In some embodiments the functional variant of SEQ ID NO: 3 comprises the following TFBS sequences: CGCCCTTTGGACC (HNF4) (SEQ ID NO: 54), GACCTTTTGCAATCCTGG (c/EBP) (SEQ ID NO: 55), CTGTTTGCT (HNF3) (SEQ ID NO: 56), GTGTTTGCTG (HNF3) (SEQ ID NO: 57), sequences complementary thereto, or functional variants of these TFBS sequences that maintain the ability to bind to bind to their respective TF (see Table 7 for further details). It is well-known in the art that there is sequence variability associated with TFBS, and that for a given TFBS a consensus sequence is typically defined based upon multiple sequence alignments, with some degree of deviation from the consensus sequence typically being present.

In some embodiments of the invention, the functional variant of SEQ ID NO: 3 comprises the sequence: CGCCCTTTGGACCTTTTGCAATCCTG-GAGCAAACAGCAAACAC (SEQ ID NO: 66), or a sequence that is at least 60%, 70%, 80%, 90%, 95% or 99% identical thereto.

In some embodiments of the invention, the functional variant of SEQ ID NO: 3 comprises a sequence that is at least 60% identical to SEQ ID NO: 3, more preferably at least 70%, 80%, 90%, 95% or 99% identical to SEQ ID NO: 3. Additionally or alternatively, a functional variant of SEQ ID NO: 3 suitably comprises a sequence which hybridises under stringent conditions to SEQ ID NO: 3.

In some embodiments of the invention the cis-regulatory enhancer element consists of SEQ ID No: 3 or a functional variant thereof.

It will be noted that the synthetic liver-specific cis-regulatory enhancer element comprising a sequence according to SEQ ID NO: 3 or a functional variant thereof can be provided on either strand of a double stranded polynucleotide and can be provided in either orientation. As such, complementary and reverse complementary sequences of SEQ ID NO: 3 or a functional variant thereof fall within the scope of the invention. Single stranded nucleic acids comprising the sequence according to SEQ ID NO: 3 or a functional variant thereof also fall within the scope of the invention.

In some embodiments of the invention the cis-regulatory enhancer element which comprises SEQ ID NO: 2 or a functional variant of SEQ ID NO: 2 is 100 or fewer nucleotides in length, suitably 90 or fewer, optionally 80 or fewer, 70 or fewer, 60 or fewer, and in some cases 56 or fewer.

In some embodiments of the invention the cis-regulatory enhancer element which comprises SEQ ID NO: 3 or a functional variant of SEQ ID NO: 3 is 100 or fewer nucleotides in length, suitably 90 or fewer, optionally 80 or fewer, 70 or fewer, 60 or fewer, 50 or fewer, and in some cases 45 or fewer.

The relatively small size of such cis-regulatory enhancer elements according to the present invention is advantageous because it allows for the cis-regulatory enhancer element to be used in vectors while taking up the minimal amount of the payload of the vector. This is particularly important when the cis-regulatory enhancer element is used in a vector with limited capacity, such as and AAV-based vector.

The cis-regulatory enhancer elements as set out above can be provided as part of a synthetic liver-specific cis-regulatory module (CRM). Such a liver-specific CRM comprises additional cis-regulatory enhancer elements, preferably other liver specific cis-regulatory enhancer elements. Some specific CRMs which comprise a cis-regulatory enhancer element as set out above are described below, but cis-regulatory enhancer elements as set out above can be provided in other CRMs.

Accordingly, in a further aspect, the present invention provides a CRM comprising a cis-regulatory enhancer element according to the first aspect of the invention. Preferably the synthetic liver-specific CRM comprises a CRE according to the first aspect of the invention operably linked to at least one further liver-specific CRE.

In some embodiments of invention there is provided a CRM comprising both of the cis-regulatory enhancer elements as defined above. Accordingly, there is provided a synthetic liver-specific CRM comprising a cis-regulatory enhancer element comprising SEQ ID NO: 2 or a functional variant of SEQ ID NO: 2 operably liked to a cis-regulatory enhancer element comprising SEQ ID NO: 3 or a functional variant of SEQ ID NO: 3.

The cis-regulatory enhancer element or synthetic liver-specific CRM as set out above can be provided as part of a synthetic liver-specific promoter, synthetic nucleic acid expression construct, vector, virion, pharmaceutical composition, or cell as discussed in more detail below, and it can be used in various methods as discussed below.

In a further aspect of the invention, there is provided a synthetic liver-specific cis-regulatory module comprising at least two cis-regulatory enhancer elements selected from the group consisting of:

A1 or a functional variant thereof;
V1 or a functional variant thereof;
V2 or a functional variant thereof;
LVR_CRE0074_SEPP1 or a functional variant thereof;
LVR_CRE0058_APOB or a functional variant thereof;
LVR_CRE0065_APOA1 or a functional variant thereof;
LVR_CRE0065_APOA1_v1 or a functional variant thereof; and
LVR_CRE0066_NR1I2 or a functional variant thereof.

A1 (also referred to as LVR_CRE0051_AMBP) has a sequence according to SEQ ID NO: 1; V1 has a sequence according to SEQ ID NO: 2; V2 has a sequence according to SEQ ID NO: 3; LVR_CRE0074_SEPP1 has a sequence according to SEQ ID NO: 4; LVR_CRE0058_APOB has a sequence according to SEQ ID NO: 5; LVR_CRE0065_APOA1 has a sequence according to SEQ ID NO: 6; LVR_CRE0065_APOA1_v1 has a sequence according to SEQ ID NO: 7; and LVR_CRE0066_NR1I2 has a sequence according to SEQ ID NO: 8.

In some embodiments of the invention, the synthetic liver-specific cis-regulatory module comprises at least three cis-regulatory elements selected the group consisting of:

A1 or a functional variant thereof;
V1 or a functional variant thereof;
V2 or a functional variant thereof;
LVR_CRE0074_SEPP1 or a functional variant thereof;
LVR_CRE0058_APOB or a functional variant thereof;

LVR_CRE0065_APOA1 or a functional variant thereof;
LVR_CRE0065_APOA1_v1 or a functional variant thereof; and
LVR_CRE0066_NR1I2 or a functional variant thereof.

In some preferred embodiments of the invention the synthetic liver-specific cis-regulatory module comprises at least one cis-regulatory enhancer element which is selected from the group consisting:

A1 or a functional variant thereof;
V1 or a functional variant thereof; and
V2 or a functional variant thereof,
combined with at least one, preferably two cis-regulatory elements selected the group consisting of:
LVR_CRE0074_SEPP1 or a functional variant thereof;
LVR_CRE0058_APOB or a functional variant thereof;
LVR_CRE0065_APOA1 or a functional variant thereof;
LVR_CRE0065_APOA1_v1 or a functional variant thereof; and
LVR_CRE0066_NR1I2 or a functional variant thereof.

Functional variants of A1 (SEQ ID NO: 1):

In some preferred embodiments it is preferred that the functional variant of A1 (SEQ ID NO: 1) comprises transcription factor binding sites (TFBS) for the same transcription factors (TF) as SEQ ID NO: 1. The TFBS present in SEQ ID NO: 1, listed in the order in which they are present, are: HNF1, HNF4, HNF3, HNF1 and HNF3. The functional variant of SEQ ID NO: 1 thus preferably comprises all of these TFBS. Preferably, they are present in the same order that they are present in SEQ ID NO: 1, i.e. in the order HNF1, HNF4, HNF3, HNF1 then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of A1 (SEQ ID NO: 1) comprises the following TFBS sequences: GTTAATTTTTAAA (HNF1) (SEQ ID NO: 74), GTGGCCCTTGG (HNF4) (SEQ ID NO: 75), TGTTTGC (HNF3) (SEQ ID NO: 76), TGGTTAATAATCTCA (HNF1) (SEQ ID NO: 77) then ACAAACA (HNF3) (SEQ ID NO: 78), sequences complementary thereto, or functional variants of these TFBS sequences that maintain the ability to bind to bind to their respective TF (see Table 5 for further details). These may be present in the same order as SEQ ID NO: 1, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of A1 (SEQ ID NO: 1) comprises the sequence:

GTTAATTTTTAAA-Na-GTGGCCCTTGG-Nb-
TGTTTGC-Nc-TGGTTAATAATCTCA-Nd-
ACAAACA (SEQ ID NO: 67), or a sequence that is at least 60%, 70%, 80%, 90%, 95% or 99% identical thereto, wherein Na, Nb, Nc, and Nd represent optional spacer sequences. When present, Na optionally has a length of from 10 to 26 nucleotides, preferably from 14 to 22 nucleotides, and more preferably 18 nucleotides. When present, Nb optionally has a length of from 8 to 22 nucleotides, preferably from 12 to 20 nucleotides, more preferably 16 nucleotides. When present, Nc optionally has a length of from 1 to 10 nucleotides, preferably 1 to 5 nucleotides, and more preferably 2 nucleotides. When present, Nd suitably has a length of from 1 to 13 nucleotides, preferably from 2 to 9 nucleotides in length, and more preferably 5 nucleotides in length.

In some embodiments, a functional variant of A1 (LVR_CRE0051_AMBP) suitably comprises a sequence that is at least 70% identical to SEQ ID NO: 1, more preferably at least 60%, 70%, 80%, 90%, 95% or 99% identical to SEQ ID NO: 1. Additionally or alternatively, a functional variant of SEQ ID NO: 1 suitably comprises a sequence which hybridises under stringent conditions to SEQ ID NO: 1.

In some embodiments of the invention the cis-regulatory enhancer element consists of SEQ ID No: 1 or a functional variant thereof.

It will be noted that the synthetic liver-specific cis-regulatory enhancer element comprising a sequence according to SEQ ID NO: 1 or a functional variant thereof can be provided on either strand of a double stranded polynucle-otide and can be provided in either orientation. As such, complementary and reverse complementary sequences of SEQ ID NO: 1 or a functional variant thereof fall within the scope of the invention. Single stranded nucleic acids com-prising the sequence according to SEQ ID NO: 1 or a functional variant thereof also fall within the scope of the invention.

Functional Variants of V1 and V2 (Also Referred to as LVR_CRE0077_V1 and LVR_CRE0078_V2, Respec-tively):

Functional variants of V1 (SEQ ID NO: 2) and V2 (SEQ ID NO: 3) are discussed in detail above.

Functional Variants of LVR_CRE0074_SEPP1:

In some embodiments it is preferred that the functional variant of LVR_CRE0074_SEPP1 (SEQ ID NO: 4) com-prises transcription factor binding sites (TFBS) for the same transcription factors (TF) as SEQ ID NO: 4. The TFBS present in SEQ ID NO: 4, listed in the order in which they are present, are: HNF4 and FoxO1a. The functional variant of SEQ ID NO: 4 thus preferably comprises all of these TFBS. Preferably, they are present in the same order that they are present in SEQ ID NO: 4, i.e. in the order HNF4 then FoxO1a. When the cis-regulatory element is associated with a promoter and gene, this order is preferably considered in an upstream to downstream direction (i.e. in the direction from distal from the transcription start site (TSS) to proxi-mal to the TSS). Spacer sequences may be provided between adjacent TFBS. In some embodiments the TFBS may suit-ably overlap, provided they remain functional, i.e. overlap-ping sequences are both able to bind their respective TFs.

In some embodiments the functional variant of LVR_CRE0074_SEPP1 (SEQ ID NO: 4) comprises the following TFBS sequences: AACATTGAACTTTGGACTA (HNF4) and GTAAACAA (FoxO1a), sequences comple-mentary thereto, or functional variants of these TFBS sequences that maintain the ability to bind to bind to their respective TF (see Table 8 for further details). These may be present in the same order as SEQ ID NO: 2, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of LVR_CRE0074_SEPP1 (SEQ ID NO: 4) com-prises the sequence:

AACATTGAACTTTGGACTA-Na-GTAAACAA (SEQ ID NO: 68), or a sequence that is at least 60%, 70%, 80%, 90%, 95% or 99% identical thereto, wherein Na represents an optional spacer sequence. When present, Na optionally has a length of from 7 to 23 nucleotides, preferably from 11 to 19 nucleotides, and more preferably 15 nucleotides.

In some embodiments, a functional variant of LVR_CRE0074_SEPP1 (SEQ ID NO: 4) suitably comprises a sequence that is at least 60% identical to SEQ ID NO: 4, more preferably at least 70%, 80%, 90%, 95% or 99% identical to SEQ ID NO: 4. Additionally or alternatively, a functional variant of SEQ ID NO: 4 suitably comprises a sequence which hybridises under stringent conditions to SEQ ID NO: 4.

In some embodiments of the invention the cis-regulatory enhancer element consists of SEQ ID No: 4 or a functional variant thereof.

It will be noted that the synthetic liver-specific cis-regulatory enhancer element comprising a sequence accord-ing to SEQ ID NO: 4 or a functional variant thereof can be provided on either strand of a double stranded polynucle-otide and can be provided in either orientation. As such, complementary and reverse complementary sequences of SEQ ID NO: 4 or a functional variant thereof fall within the scope of the invention. Single stranded nucleic acids com-prising the sequence according to SEQ ID NO: 4 or a functional variant thereof also fall within the scope of the invention.

Functional Variants of LVR_CRE0058_APOB:

In some embodiments it is preferred that the functional variant of LVR_CRE0058_APOB (SEQ ID NO: 5) com-prises transcription factor binding sites (TFBS) for the same transcription factors (TF) as SEQ ID NO: 5. The TFBS present in SEQ ID NO: 5, listed in the order in which they are present, are: HNF4 and c/EBP. The functional variant of SEQ ID NO: 5 thus preferably comprises all of these TFBS. Preferably, they are present in the same order that they are present in SEQ ID NO: 4, i.e. in the order HNF4 then c/EBP. When the cis-regulatory element is associated with a pro-moter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suit-ably overlap, provided they remain functional, i.e. overlap-ping sequences are both able to bind their respective TFs.

In some embodiments the functional variant of LVR_CRE0058_APOB (SEQ ID NO: 5) comprises the following TFBS sequences: CGCCCTTTGGACC (HNF4) (SEQ ID NO: 60) and GACCTTTTGCAATCCTGG (c/EBP) (SEQ ID NO: 61), sequences complementary thereto, or functional variants of these TFBS sequences that maintain the ability to bind to bind to their respective TF (see Table 9 for further details). These may be present in the same order as SEQ ID NO: 5, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of LVR_CRE0058_APOB (SEQ ID NO: 5) com-prises the sequence:

GCGCCCTTTGGACCTTTTGCAATCCTGG (SEQ ID NO: 69), or a sequence that is at least 60%, 70%, 80%, 90%, 95% or 99% identical thereto.

In some embodiments, a functional variant of LVR_CRE0058_APOB suitably comprises a sequence that is at least 60% identical to SEQ ID NO: 5, more preferably at least 70%, 80%, 90%, 95% or 99% identical to SEQ ID NO: 5. Additionally or alternatively, a functional variant of SEQ ID NO: 5 suitably comprises a sequence which hybridises under stringent conditions to SEQ ID NO: 5.

In some embodiments of the invention the cis-regulatory enhancer element consists of SEQ ID No: 5 or a functional variant thereof.

It will be noted that the synthetic liver-specific cis-regulatory enhancer element comprising a sequence according to SEQ ID NO: 5 or a functional variant thereof can be provided on either strand of a double stranded polynucleotide and can be provided in either orientation. As such, complementary and reverse complementary sequences of SEQ ID NO: 5 or a functional variant thereof fall within the scope of the invention. Single stranded nucleic acids comprising the sequence according to SEQ ID NO: 5 or a functional variant thereof also fall within the scope of the invention.

Functional Variants of LVR_CRE0065_APOA1:

In some embodiments it is preferred that the functional variant of LVR_CRE0065_APOA1 (SEQ ID NO: 6) comprises transcription factor binding sites (TFBS) for the same transcription factors (TF) as SEQ ID NO: 6. The TFBS present in SEQ ID NO: 6, listed in the order in which they are present, are: RXR Alpha, HNF3 and HNF3. The functional variant of SEQ ID NO: 6 thus preferably comprises all of these TFBS. Preferably, they are present in the same order that they are present in SEQ ID NO: 6, i.e. in the order RXR Alpha, HNF3 then HNF3. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of LVR_CRE0065_APOA1 (SEQ ID NO: 6) comprises the following TFBS sequences: ACTGAACCCTTGACCCCTGCCCT (RXR Alpha) (SEQ ID NO: 62), CTGTTTGCCC (HNF3) (SEQ ID NO: 63), and CTATTTGCCC (HNF3) (SEQ ID NO: 53), sequences complementary thereto, or functional variants of these TFBS sequences that maintain the ability to bind to bind to their respective TF (see Table 10 for further details). These may be present in the same order as SEQ ID NO: 6, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of LVR_CRE0065_APOA1 (SEQ ID NO: 6) comprises the sequence:
ACTGAACCCTTGACCCCT-Na-CTGTTTGCCC-Nb-TATTTGCCC (SEQ ID NO: 70), or a sequence that is at least 60%, 70%, 80%, 90%, 95% or 99% identical thereto, wherein Na and Nb represent optional spacer sequences. When present, Na optionally has a length of from 14 to 30 nucleotides, preferably from 18 to 26 nucleotides, and more preferably 22 nucleotides. When present, Nb optionally has a length of from 1 to 10 nucleotides, preferably from 2 to 6 nucleotides, and more preferably 4 nucleotides.

In some embodiments, a functional variant of LVR_CRE0065_APOA1 suitably comprises a sequence that is at least 70% identical to SEQ ID NO: 6, more preferably at least 80%, 90% or 95% identical to SEQ ID NO: 6. Additionally or alternatively, a functional variant of SEQ ID NO: 6 suitably comprises a sequence which hybridises under stringent conditions to SEQ ID NO: 6.

In some embodiments of the invention the cis-regulatory enhancer element consists of SEQ ID No: 6 or a functional variant thereof.

It will be noted that the synthetic liver-specific cis-regulatory enhancer element comprising a sequence according to SEQ ID NO: 6 or a functional variant thereof can be provided on either strand of a double stranded polynucleotide and can be provided in either orientation. As such, complementary and reverse complementary sequences of SEQ ID NO: 6 or a functional variant thereof fall within the scope of the invention. Single stranded nucleic acids comprising the sequence according to SEQ ID NO: 6 or a functional variant thereof also fall within the scope of the invention.

Functional Variants of LVR_CRE0065_APOA1_v1:

In some embodiments it is preferred that the functional variant of LVR_CRE0065_APOA1_v1 (SEQ ID NO: 7) comprises transcription factor binding sites (TFBS) for the same transcription factors (TF) as SEQ ID NO: 7. The TFBS present in SEQ ID NO: 7, listed in the order in which they are present, are: RXR Alpha, HNF3, HNF3 and HNF4. The functional variant of SEQ ID NO: 7 thus preferably comprises all of these TFBS. Preferably, they are present in the same order that they are present in SEQ ID NO: 7, i.e. in the order RXR Alpha, HNF3, HNF3 then HNF4. When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of LVR_CRE0065_APOA1_v1 (SEQ ID NO: 7) comprises the following TFBS sequences: ACTGAACCCTTGACCCCTGCCCT (RXR Alpha) (SEQ ID NO: 62), CTGTTTGCCC (HNF3) (SEQ ID NO: 63), CTATTTGCCC (HNF3) (SEQ ID NO: 53) and TGATCCTTGAACTCT (HNF4) (SEQ ID NO: 64), sequences complementary thereto, or functional variants of these TFBS sequences that maintain the ability to bind to bind to their respective TF (see Table 11 for further details). These may be present in the same order as SEQ ID NO: 7, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of LVR_CRE0065_APOA1_v1 (SEQ ID NO: 7) comprises the sequence:
ACTGAACCCTTGACCCCT-Na-CTGTTTGCCC-Nb-TATTTGCCC-Nc-TGATCCTTGAACTCT (SEQ ID NO: 71), or a sequence that is at least 60%, 70%, 80%, 90%, 95% or 99% identical thereto,
wherein Na, Nb and Nc represent optional spacer sequences. When present, Na optionally has a length of from 14 to 30 nucleotides, preferably from 18 to 26 nucleotides, and more preferably 22 nucleotides. When present, Nb optionally has a length of from 1 to 10 nucleotides, preferably from 2 to 6 nucleotides, and more preferably 4 nucleotides. When present, Nc optionally has a length of from 9 to 25 nucleotides, preferably from 13 to 21 nucleotides, and more preferably 17 nucleotides.

In some embodiments, a functional variant of LVR_CRE0065_APOA1_v1 suitably comprises a sequence that is at least 60% identical to SEQ ID NO: 7, more preferably at least 70%, 80%, 90%, 95% or 99% identical to SEQ ID NO: 7. Additionally or alternatively, a functional variant of SEQ ID NO: 7 suitably comprises a sequence which hybridises under stringent conditions to SEQ ID NO: 7.

In some embodiments of the invention the cis-regulatory enhancer element consists of SEQ ID No: 7 or a functional variant thereof.

It will be noted that the synthetic liver-specific cis-regulatory enhancer element comprising a sequence according to SEQ ID NO: 7 or a functional variant thereof can be provided on either strand of a double stranded polynucleotide and can be provided in either orientation. As such, complementary and reverse complementary sequences of SEQ ID NO: 7 or a functional variant thereof fall within the scope of the invention. Single stranded nucleic acids comprising the sequence according to SEQ ID NO: 7 or a functional variant thereof also fall within the scope of the invention.

Functional Variants of LVR_CRE0066_NR1I2:

In some embodiments it is preferred that the functional variant of LVR_CRE0066_NR1I2 (SEQ ID NO: 8) comprises transcription factor binding sites (TFBS) for the same transcription factors (TF) as SEQ ID NO: 8. The TFBS present in SEQ ID NO: 8, listed in the order in which they are present, are: HNF4G and FOS::JUN. The functional variant of SEQ ID NO: 8 thus preferably comprises all of these TFBS. Preferably, they are present in the same order that they are present in SEQ ID NO: 8, i.e. in the order HNF4G then FOS::JUN When the cis-regulatory element is associated with a promoter and gene, this order is preferably considered in an upstream to downstream direction (i.e. in the direction from distal from the transcription start site (TSS) to proximal to the TSS). Spacer sequences may be provided between adjacent TFBS. In some embodiments the TFBS may suitably overlap, provided they remain functional, i.e. overlapping sequences are both able to bind their respective TFs.

In some embodiments the functional variant of LVR_CRE0066_NR1I2 (SEQ ID NO: 8) comprises the following TFBS sequences: GCAGGGCAAAGTGCA (HNF4G) (SEQ ID NO: 79) and GATGACTCAG (FOS::JUN) (SEQ ID NO: 80), sequences complementary thereto, or functional variants of these TFBS sequences that maintain the ability to bind to bind to their respective TF (see Table 12 for SEQ ID NOs). These may be present in the same order as SEQ ID NO: 8, i.e. the order in which they are set out above. It is well-known in the art that there is sequence variability associated with TFBS, and that for a given TFBS there is typically a consensus sequence, from which some degree of deviation is typically present.

In some embodiments of the invention, the functional variant of LVR_CRE0066_NR1I2 (SEQ ID NO: 8) comprises the sequence:

GCAGGGCAAAGTGCA-Na-GATGACTCAG (SEQ ID NO: 73) or a sequence that is at least 60%, 70%, 80%, 90%, 95% or 99% identical thereto, wherein Na represents an optional spacer sequence. When present, Na optionally has a length of from 10 to 28 nucleotides, preferably from 14 to 24 nucleotides, and more preferably 19 nucleotides.

In some embodiments, a functional variant of LVR_CRE0066_NR1I2 suitably comprises a sequence that is at least 60% identical to SEQ ID NO: 8, more preferably at least 70%, 80%, 90%, 95% or 99% identical to SEQ ID NO: 8. Additionally or alternatively, a functional variant of SEQ ID NO: 8 suitably comprises a sequence which hybridises under stringent conditions to SEQ ID NO: 8.

In some embodiments of the invention the cis-regulatory enhancer element consists of SEQ ID No: 8 or a functional variant thereof.

It will be noted that the synthetic liver-specific cis-regulatory enhancer element comprising a sequence according to SEQ ID NO: 8 or a functional variant thereof can be provided on either strand of a double stranded polynucleotide and can be provided in either orientation. As such, complementary and reverse complementary sequences of SEQ ID NO: 8 or a functional variant thereof fall within the scope of the invention. Single stranded nucleic acids comprising the sequence according to SEQ ID NO: 8 or a functional variant thereof also fall within the scope of the invention.

In some preferred embodiments of the present invention, there is provided a synthetic liver-specific cis-regulatory module (CRM) comprising one of the following combinations of cis-regulatory elements, or functional variants of the said cis-regulatory elements:

LVR_CRE0074_SEPP1, LVR_CRE0058_APOB, and LVR_CRE0065_APOA1;

A1, LVR_CRE0074_SEPP1LVR_CRE0058_APOB, LVR_CRE0065_APOA1;

V1, LVR_CRE0074_SEPP1, LVR_CRE0058_APOB, LVR_CRE0065_APOA1;

V2, LVR_CRE0074_SEPP1, LVR_CRE0058_APOB, LVR_CRE0065_APOA1;

LVR_CRE0058_APOB, LVR_CRE0065_APOA1, LVR_CRE0066_NR1I2;

A1, LVR_CRE0058_APOB, LVR_CRE0065_APOA1, LVR_CRE0066_NR1I2;

V1, LVR_CRE0058_APOB, LVR_CRE0065_APOA1, LVR_CRE0066_NR1I2;

V2, LVR_CRE0058_APOB, LVR_CRE0065_APOA1, LVR_CRE0066_NR1I2;

LVR_CRE0074_SEPP1, LVR_CRE0058_APOB, LVR_CRE0066_NR1I2;

A1, LVR_CRE0074_SEPP1, LVR_CRE0058_APOB, LVR_CRE0066_NR1I2;

V1, LVR_CRE0074_SEPP1, LVR_CRE0058_APOB, LVR_CRE0066_NR1I2;

V2, LVR_CRE0074_SEPP1, LVR_CRE0058_APOB, LVR_CRE0066_NR1I2;

LVR_CRE0074_SEPP1, LVR_CRE0058_APOB;

A1, LVR_CRE0074_SEPP1, LVR_CRE0058_APOB;

V1, LVR_CRE0074_SEPP1, LVR_CRE0058_APOB; or

V2, LVR_CRE0074_SEPP1, LVR_CRE0058_APOB.

In the above CRMs, the cis-regulatory elements, or functional variants of the said cis-regulatory elements, can be in any order. In preferred embodiments they are present in the CRM in the order set out above. One or more spacer sequences can optionally be positioned between adjacent cis-regulatory elements.

In some preferred embodiments of the present invention, there is provided a synthetic liver-specific cis-regulatory module (CRM) comprising one of the following combinations of cis-regulatory elements, or functional variants of the said cis-regulatory elements:

(LVR_CRE0074_SEPP1)-S-(LVR_CRE0058_APOB)-S-(LVR_CRE0065_APOA1);

(A1)-S-(LVR_CRE0074_SEPP1)-S-(LVR_CRE0058_APOB)-S-(LVR_CRE0065_APOA1);

(V1)-S-(LVR_CRE0074_SEPP1)-S-(LVR_CRE0058_APOB)-S-(LVR_CRE0065_APOA1);

(V2)-S-(LVR_CRE0074_SEPP1)-S-(LVR_CRE0058_APOB)-S-(LVR_CRE0065_APOA1);

(LVR_CRE0058_APOB)-S-(LVR_CRE0065_APOA1)-S-(LVR_CRE0066_NR1I2);

(A1)-S-(LVR_CRE0058_APOB)-S-(LVR_CRE0065_APOA1)-S-(LVR_CRE0066_NR1I2);

(V1)-S-(LVR_CRE0058_APOB)-S-(LVR_CRE0065_APOA1)-S-(LVR_CRE0066_NR1I2);

(V2)-S-(LVR_CRE0058_APOB)-S-(LVR_CRE0065_APOA1)-S-(LVR_CRE0066_NR1I2);

(LVR_CRE0074_SEPP1)-S-(LVR_CRE0058_APOB)-S-(LVR_CRE0066_NR1I2);

(A1)-S-(LVR_CRE0074_SEPP1)-S-(LVR_CRE0058_APOB)-S-(LVR_CRE0066_NR1I2);

(V1)-S-(LVR_CRE0074_SEPP1)-S-(LVR_CRE0058_APOB)-S-(LVR_CRE0066_NR1I2);

(V2)-S-(LVR_CRE0074_SEPP1)-S-(LVR_CRE0058_APOB)-S-(LVR_CRE0066_NR1I2);

(LVR_CRE0074_SEPP1)-S-(LVR_CRE0058_APOB);

(A1)-S-(LVR_CRE0074_SEPP1)-S-(LVR_CRE0058_APOB);

(V1)-S-(LVR_CRE0074_SEPP1)-S-(LVR_CRE0058_APOB); or (V2)-S-(LVR_CRE0074_SEPP1)-S-(LVR_CRE0058_APOB), wherein S represents an optional spacer sequence positioned between adjacent cis-regulatory elements.

Details of the recited cis-regulatory elements and functional variants thereof are set out above.

In some embodiments of the present invention, there is provided a synthetic liver-specific cis-regulatory module comprising SEQ ID NO: 15, SEQ ID NO: 16, SEQ ID NO: 17, SEQ ID NO: 18. SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30, or a functional variant thereof. The functional variant thereof may suitably comprise a sequence that is at least 60%, 70%, 80%, 90%, 95% or 99% identical to any one of SEQ ID NO: 15 to SEQ ID NO: 30. Additionally or alternatively, a functional variant of SEQ ID NO: 15 to SEQ ID NO: 30, suitably comprises a sequence which hybridises under stringent conditions to the reference sequence. Functional variants of SEQ ID NO: 15 to SEQ ID NO: 30 include variants in which one or more of the CREs provided therein has been replaced with a functional variant thereof as defined above, and/or where the order of the CREs provided therein has been altered.

In a further aspect of the invention there is provided a synthetic cis-regulatory enhancer element selected from the group consisting of:

LVR_CRE0074_SEPP1 or a functional variant thereof;

LVR_CRE0058_APOB or a functional variant thereof;

LVR_CRE0065_APOA1 or a functional variant thereof;

LVR_CRE0065_APOA1_v1 or a functional variant thereof; and

LVR_CRE0066_NR1I2 or a functional variant thereof.

Functional variants of LVR_CRE0074_SEPP1, LVR_CRE0058_APOB, LVR_CRE0065_APOA1, LVR_CRE0065_APOA1_v1, and LVR_CRE0066_NR1I2 are discussed above. These synthetic cis-regulatory enhancer elements can be used in the various aspects of the invention in the same way as the synthetic cis-regulatory enhancer elements of the first aspect of the invention (i.e. V1 or V2 or functional variants thereof).

In a further aspect of the present invention, there is provided a synthetic liver-specific promoter comprising a synthetic liver-specific cis-regulatory element or cis-regulatory module as set out above.

Suitably the synthetic liver-specific promoter comprises a synthetic liver-specific cis-regulatory element or cis-regulatory module of the present invention operably linked to a minimal promoter. Examples of suitable minimal promoters for use in the present invention include, but are not limited to, the CMV-minimal promoter, MinTk minimal promoter, and the LVR_CRE0052_G6PC minimal promoter.

In some embodiments of the present invention, the synthetic liver-specific cis-regulatory element or cis-regulatory module is operably linked to the LVR_CRE0052_G6PC minimal promoter, which has the sequence GGG-CATATAAAACAGGGGCAAGGCACAGACTCAT-AGCAGAGCAATCACCACCAAGCCT GGAATAACTGCAGCCACC (SEQ ID NO: 9).

Other suitable minimal promoters are known in the art.

In another embodiment of the invention, the synthetic liver-specific cis-regulatory element or cis-regulatory module can be operably linked to a liver-specific promoter, e.g. a liver-specific proximal promoter (i.e. a promoter, typically a proximal promoter, that is itself capable of driving liver-specific expression of an operably linked gene). In this case the synthetic liver-specific cis-regulatory element or cis-regulatory module may act to potentiate the liver-specific proximal promoter.

In some embodiments of the present invention, the synthetic liver-specific cis-regulatory element or cis-regulatory module is operably linked to the SERPINA7 proximal promoter (also referred to as LVR_CRE0079_SERPINA7), which has the following sequence CTCTTTTGTTTTACAT-GAAGGGTCTGGCAGCCAAAGCAATCACTCAA-AGTTCAAACCTTA TCATTTTTTGCTTTGTTCCT-CTTGGCCTTGGTTTTGTACATCAGCTTTGAAAATAC-CATCC CAGGGTTAATGCTGGGGTTAATTTATAAC-TAAGAGTGCTCTAGTTTTGCAATACAGGAC ATGC-TATAAAAATGGAAAGATGTTGCTTTCTGAGAGAT-GCGCCACC (SEQ ID NO: 10).

Non-limiting examples of liver-specific promoters that may be used include, but are not limited to, the ApoA-I promoter, the ApoA-II promoter, the ApoA-IV promoter, the ApoB promoter, the ApoC-1 promoter, the ApoC-II promoter, the ApoC-III promoter, the ApoE promoter, the albumin promoter, the α-fetoprotein promoter, the phosphoenolpyruvate carboxykinase (PCK1) promoter, the phosphoenolpyruvate carboxykinase 2 (PCK2) promoter, the transthyretin (TTR) promoter, the α-antitrypsin (AAT or SERPINA1) promoter, the TK (thymidine kinase) promoter, the hemopexin promoter, the alcohol dehydrogenase 6 promoter, the cholesterol 7alpha-25 hydroxylase promoter, the factor IX promoter, the a-microglobulin promoter, the SV40 promoter, the CMV promoter, the Rous Sarcoma Virus-LTR promoter and the HBV promoter. Minimal promoters derived from these promoters can of course also be used.

Minimal or proximal promoters used in the present invention can be natural (i.e. obtained or derived from a naturally occurring gene promoter) or can be synthetic (i.e., non-naturally occurring).

Functional variants of the minimal or proximal promoters described above also form part of the present invention, i.e. variants of the minimal or proximal promoters that remain capable of cooperating with the synthetic liver-specific cis-regulatory element or cis-regulatory module of the present invention to drive liver-specific transcription of an operably linked gene.

In some embodiments of the invention, the synthetic liver-specific promoter comprises or consists of a sequence according to SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO:40, SEQ ID NO: 41, SEQ ID NO: 42, SEQ ID NO: 43, SEQ ID NO: 44, SEQ ID NO: 45, SEQ ID NO: 46, or a functional variant of any thereof. The functional variant thereof may suitably comprise a sequence that is at least 60%, 70%, 80%, 90%, 95% or 99% identical to any one of SEQ ID NO: 31 to SEQ ID NO: 46.

In some embodiments a synthetic liver-specific promoter of the invention is able to increase expression of gene (e.g. a therapeutic gene or gene of interest) in the liver of a subject or in a liver cell by at least 20%, at least 40%, at least 60%, at least 80%, at least 100%, at least 200%, at least 300%, at least 500%, at least 1000% or more relative to a known liver-specific promoter, preferably the LP-1 promoter.

In some embodiments, a synthetic liver-specific promoter of the invention is able to promote liver-specific transgene expression and has an activity in liver cells which is at least 15%, 20%, 30%, 40%, 50%, 60%, 70%, 80%, 90%, 100%, 125%, 150%, 175%, 200%, 250%, 300%, 350% or 400% of the activity of the TBG promoter.

In some embodiment, the length of the synthetic liver-specific CRM is 450 nucleotides or fewer, optionally 400, 350, 300, 350, 200, 175, 150, 125, 110, 101 or fewer. In some embodiment, the length of the synthetic liver-specific promoter is 500 nucleotides or fewer, optionally 450, 400, 350, 300, 275 or fewer. Generally shorter length is preferable where, for example, capacity of a vector is limited. Short length combined with high activity is desirable.

In some embodiments of the invention, the CRM or synthetic liver-specific promoter does not comprise both V1 (or a functional variant thereof) and V2 (or a functional variant thereof). In some embodiments of the invention, where a CRE, CRM or synthetic liver-specific promoter comprises either V1 or V2 (or a functional variant thereof), it does not comprise a further CRE selected from the group consisting of: V1 (or a functional variant thereof) and V2 (or a functional variant thereof). In some embodiments of the invention, the CRM or synthetic liver-specific promoter does not comprise more than one CRE selected from the group consisting of: V1 (or a functional variant thereof) or V2 (or a functional variant thereof).

In some embodiments of the invention, the CRE, CRM or synthetic liver-specific promoter does not comprise V1 or a functional variant thereof or V2 or a functional variant thereof.

In some embodiments of the invention, the CRM or synthetic liver-specific promoter does not comprise the sequence GGACTTAGCCCCTGTTTGCTCCTCCGA-TAACTGGGGTGACCTTGGTTAATATTCACCA (SEQ ID NO: 81), or GCCCCTGTTTGCTCCTCCGA-TAACTGGGGGTGACCTTGGTTAATATTCACCA (SEQ ID NO: 82), or a functional variant of either thereof. These sequences are portions the SEPRINA1 promoter.

In some embodiments of the invention, where the CRM or synthetic liver-specific promoter comprises either V1 or V2 (or functional variants of any thereof), it does not contain SEQ ID NO: 81 or SEQ ID NO: 82 (or functional variants of any thereof). Thus, in some embodiments, the CRM or synthetic liver-specific promoter contains not more than one of sequences V1, V2, SEQ ID NO: 81 and SEQ ID NO: 82.

In some embodiments of the invention, the CRM or synthetic liver-specific promoter comprises not more than two of the following elements: LVR_CRE0080_PROC, LVR_CRE0081_APOA1, LVR_CRE0061_APOB, LVR_CRE0082_APOC4, SEQ ID NO: 81 and SEQ ID NO: 82, or functional variants of any thereof. In some embodiments of the invention, the CRM or synthetic liver-specific promoter comprises not more than one of said elements, or functional variants of any thereof. In some embodiments of the invention, the CRM or synthetic liver-specific promoter does not comprise any of said elements, or functional variants of any thereof. LVR_CRE0080_PROC, and LVR_CRE0081_APOA1 are components of V1, and LVR_CRE0061_APOB, LVR_CRE0082_APOC4 are components of V2 (see Tables 3 and 4 for further details).

In some embodiments of the invention, the synthetic liver-specific promoter does not comprise the LVR_CRE0052_G6PC minimal promoter or a functional variant thereof.

In some embodiments of the invention, the CRM or synthetic liver-specific promoter does not comprise a sequence as disclosed in European patent application no 18207027.6.

The functional variants of the any of the sequences in the disclaimers and embodiments discussed above can have, for example, a sequence having 60%, 70%, 80%, 90%, 95% or 99% identity to any of said reference sequences.

In a further aspect of the present invention, there is provided a synthetic liver-specific expression cassette comprising a synthetic liver-specific promoter of the present invention operatively linked to a gene (suitably a transgene).

The gene typically encodes a desired gene expression product such as a polypeptide (protein) or RNA. The gene may be a full-length cDNA or genomic DNA sequence, or any fragment, subunit or mutant thereof that has at least some desired biological activity.

Where the gene encodes a protein, it can be essentially any type of protein. By way of non-limiting example, the protein can be an enzyme, an antibody or antibody fragment (e.g. a monoclonal antibody), a viral protein (e.g. REP-CAP, REV, VSV-G, or RD114), a therapeutic protein, or a toxic protein (e.g. Caspase 3, 8 or 9).

In some preferred embodiments of the present invention, the gene encodes a therapeutic expression product, preferably a therapeutic polypeptide suitable for use in treating a disease or condition associated with the liver. The therapeutic expression product can be a protein, e.g. a secretable protein such as, e.g., a clotting factor (e.g., factor IX or factor VIII), a cytokine, a growth factor, an antibody or nanobody, a chemokine, a plasma factor, insulin, erythropoietin, lipoprotein lipase, or a toxic protein. Alternatively, the therapeutic expression product may be RNA, such as an siRNA or miRNA. A non-exhaustive list of therapeutic expression products (and sequences encoding them) envisaged for use in the present invention includes: factor VIII, factor IX, factor VII, factor X, von Willebrand factor, erythropoietin (EPO), interferon-a, interferon-B, interferon-y, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumour necrosis factor (TNF), afamin (AFM), a1-antitrypsin, a-galactosidase A, $\alpha$-L-iduronidase, ATP7b, ornithine transcarbamoylase, phenylalanine hydroxylase, lipoprotein lipase, aromatic amino acid decarboxylase (AADC), ATPase Sarcoplasmic/Endoplasmic Reticulum Ca2+ Transporting 2 (ATP2A2), cystic fibrosis transmembrane conductance regulator (CTFR), glutamic acid decarboxylase 65 kDa protein (GAD65), glutamic acid decarboxylase 67 kDa protein (GAD67), lipoprotein lipase (LPL), nerve growth factor (NGF), neurturin (NTN), porphobilinogen deaminase (PBGD), sarcoglycan alpha (SGCA), soluble fms-like tyrosine kinase-1 (sFLT-1), apoliproteins, low-density lipoprotein receptor (LDL-R), albumin, glucose-6-phosphatase, antibodies, nanobodies, aptamers, anti-viral dominant-negative proteins, and functional fragments, subunits or mutants thereof. Preferably the protein is a primate protein, more preferably a human protein.

In some embodiments of the invention, the synthetic liver-specific expression cassette comprises a gene useful for gene editing, e.g. a gene encoding a site-specific nuclease, such as a meganuclease, zinc finger nuclease (ZFN), transcription activator-like effector-based nuclease (TALEN), or the clustered regularly interspaced short palindromic repeats system (CRISPR-Cas). Suitably the site-specific nuclease is adapted to edit a desired target genomic locus by making a cut (typically a site-specific double-strand break) which is then repaired via non-homologous end-joining (NHEJ) or homology dependent repair (HDR), resulting in a desired edit. The edit can be the partial or complete repair of a gene that is dysfunctional, or the knock-down or knock-out of a functional gene.

Suitably the synthetic liver-specific expression cassette comprises sequences providing or coding for one or more of, and preferably all of, a ribosomal binding site, a start codon, a stop codon, and a transcription termination sequence. Suitably the expression cassette comprises a nucleic acid encoding a posttranscriptional regulatory element. Suitably the expression cassette comprises a nucleic acid encoding a polyA element.

In a further aspect of the present invention, there is provided a vector comprising a synthetic liver-specific cis-regulatory element, synthetic liver-specific cis-regulatory module, synthetic liver-specific promoter or synthetic liver-specific expression cassette as defined above.

In some preferred embodiments the vector is a gene therapy vector. Various gene therapy vectors are known in the art, and mention can be made of AAV vectors, adenoviral vectors, retroviral vectors and lentiviral vectors. Where the vector is a gene therapy vector the vector preferably comprises a nucleic acid sequence operably linked to the liver-specific cis-regulatory element, synthetic liver-specific cis-regulatory module or synthetic liver-specific promoter that encodes a therapeutic product, typically a therapeutic protein. The therapeutic protein may be a secretable protein. Non-limiting examples of secretable proteins are discussed above, and exemplary secretable therapeutic proteins, include clotting factors, such as factor VIII or factor IX, insulin, erythropoietin, lipoprotein lipase, antibodies or nanobodies, growth factors, cytokines, chemokines, plasma factors, toxic proteins, etc.

In some embodiments of the invention, the vector is a viral vector, such as a retroviral, lentiviral, adenoviral, or adeno-associated viral (AAV) vector. In some preferred embodiments the vector is an AAV vector. In some preferred embodiments the AAV has a serotype suitable for liver transduction. In some embodiments, the AAV is selected from the group consisting of: AAV2, AAV5, AAV6, AAV7, AAV8, AAV9, or derivatives thereof. AAV vectors are preferably used as self-complementary, double-stranded AAV vectors (scAAV) in order to overcome one of the limiting steps in AAV transduction (i.e. single-stranded to double-stranded AAV conversion), although the use of single-stranded AAV vectors (ssAAV) is also encompassed herein. In some embodiments of the invention, the AAV vector is chimeric, meaning it comprises components from at least two AAV serotypes, such as the ITRs of an AAV2 and the capsid protein of an AAV5.

The invention further provides recombinant virions (viral particles) comprising a synthetic liver-specific cis-regulatory element, synthetic liver-specific cis-regulatory module, synthetic liver-specific promoter or synthetic liver-specific expression cassette as described above.

In some embodiments of the invention, the vector is a plasmid. Such a plasmid may include a variety of other functional nucleic acid sequences, such as one or more selectable markers, one or more origins of replication, polycloning sites and the like.

In some embodiments of the invention, the vector is an expression vector for expression in eukaryotic cells. Examples of eukaryotic expression vectors include, but are not limited to, pW-LNEO, pSV2CAT, pOG44, pXTI and pSG available from Stratagene; pSVK3, pBPV, pMSG and pSVL available from Amersham Pharmacia Biotech; and pCMVDsRed2-express, pIRES2-DsRed2, pDsRed2-Mito, pCMV-EGFP available from Clontech. Many other vectors are well-known and commercially available. For mammalian cells adenoviral vectors, the pSV and the pCMV series of vectors are particularly well-known non-limiting examples. There are many well-known yeast expression vectors including, without limitation, yeast integrative plasmids (YIp) and yeast replicative plasmids (YRp). For plants the Ti plasmid of agrobacterium is an exemplary expression vector, and plant viruses also provide suitable expression vectors, e.g. tobacco mosaic virus (TMV), potato virus X, and cowpea mosaic virus.

The vectors or virions of the present invention may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

Accordingly, a further aspect of the invention provides a pharmaceutical composition comprising a vector or virion as described herein.

In a further aspect of the invention, there is provided a synthetic liver-specific cis-regulatory enhancer element, synthetic liver-specific cis-regulatory module, synthetic liver-specific promoter, nucleic acid expression construct, vector, virion or pharmaceutical composition according to various aspects of the present invention for use in the treatment of a disease, preferably a disease associated with aberrant gene expression in the liver (e.g. a genetic liver disease). Various diseases associated with aberrant gene expression in the liver are discussed above, and these include but are not limited to haemophilia (including haemophilia A or B), familial hypercholesterolemia, ornithine transcarbamylase deficiency, phenylketonuria, ornithine transcarbamylase deficiency, glycogen storage disease, α1-antitrypsin deficiency, hereditary hemochromatosis, tyrosinemia type 1, argininosuccinic aciduria, hepatitis virus infection, non-viral hepatitis, liver cancer, genetic cholestasis, Wilson's disease, and various other liver diseases (such as non-alcoholic fatty liver disease (NAFLD), and alcohol-related liver disease (ARLD). Use for the treatment of haemophilia A or B represent preferred embodiments of the invention.

In a further aspect of the invention, there is provided the use of a synthetic liver-specific cis-regulatory enhancer element, synthetic liver-specific cis-regulatory module, synthetic liver-specific promoter, synthetic liver-specific expression cassette, vector or virion according to various aspects of the present invention for the manufacture of a pharmaceutical composition for treatment of any condition or disease mentioned herein.

According to a further aspect of the present invention, there is provided a cell comprising a synthetic liver-specific cis-regulatory enhancer element, synthetic liver-specific cis-regulatory module, synthetic liver-specific promoter, synthetic liver-specific expression cassette, vector or virion according to various aspects of the invention. Suitably the cell is a eukaryotic cell. The eukaryotic cell can suitably be a fungal cell (e.g. yeast cell), an animal (metazoan) cell (e.g. mammalian cells), or a plant cell. Alternatively, the cell may be a prokaryotic cell.

In some embodiments of the invention, the cell is ex vivo, e.g. in cell culture. In other embodiments of the invention the cell may be part of a tissue or multicellular organism.

In a preferred embodiment, the cell is a liver cell (hepatocyte), which may be ex vivo or in vivo. The liver cell may be a primary liver cell or a cell of a liver-derived cell line, e.g. an immortalised cell line. The cell may be present within a liver tissue environment (e.g. within a liver) or may be isolated from liver tissue, e.g. and it may be in cell culture. Suitably the cell is a human cell.

The synthetic liver-specific cis-regulatory element, synthetic liver-specific cis-regulatory module, synthetic liver-specific promoter, synthetic liver-specific expression cassette or vector according to various aspects of the invention may be inserted into the genome of the cell, or it may be present in an episomal vector.

In a further aspect the present invention provides a method for producing an expression product, the method comprising providing a synthetic liver-specific expression cassette as set our above (preferably in a vector as set out above) in a liver cell (hepatocyte) and expressing the gene present in the synthetic liver-specific expression cassette.

The method suitably comprises maintaining said liver cell under suitable conditions for expression of the gene. In culture this may comprise incubating the cell, or tissue comprising the cell, under suitable culture conditions. The expression may of course be in vivo, e.g. in one or more cells in the liver of a subject.

Suitably the method comprises the step of introducing the synthetic liver-specific expression cassette into the liver cell. A wide range of methods of transfecting liver cells are well-known in the art. A preferred method of transfecting liver cells is transducing the cells with a viral vector comprising the synthetic liver-specific expression cassette, e.g. an AAV vector.

It will be evident to the skilled person that a synthetic liver-specific cis-regulatory element, synthetic liver-specific cis-regulatory module, synthetic liver-specific promoter, synthetic liver-specific expression cassette, vector or virion according to various aspects of the invention may be used for gene therapy. Accordingly, the use of the such nucleic acid sequences in gene therapy forms part of the present invention.

A preferred aspect of the invention provides synthetic liver-specific expression cassettes or vectors as set out above for use in gene therapy, preferably gene therapy through liver-specific expression of a therapeutic gene, preferably for treatment of a disease involving aberrant gene expression in the liver (for example haemophilia A or B).

In a further aspect the present invention provides a method of expressing a therapeutic transgene in a liver cell, the method comprising introducing into the liver cell a synthetic liver-specific expression cassette or vector according to the present invention. The liver cell can be in vivo or ex vivo.

In a further aspect the present invention provides a method of gene therapy of a subject, preferably a human, in need thereof, the method comprising:

introducing into the liver of the subject a synthetic liver-specific expression cassette, vector or virion of the present invention, which comprises a gene encoding a therapeutic product.

The method suitably comprises expressing a therapeutic amount of the therapeutic product from the gene in the liver of said subject.

Genes encoding suitable therapeutic gene products are discussed above. However, specific mention may be made of therapeutic proteins, such as factor VIII and IX for the treatment of haemophilia.

The method suitably comprises administering a vector or virion according to the present invention to the subject. Suitably the vector is a viral gene therapy vector, preferably an AAV vector.

In some embodiments, the method comprises administering the viral gene therapy vector systemically. Systemic administration may be enteral (e.g. oral, sublingual, and rectal) or parenteral (e.g. injection). Preferred routes of injection include intravenous, intramuscular, subcutaneous, intra-arterial, intra-articular, intrathecal, and intradermal injections.

In some embodiments, the viral gene therapy vector may be administered concurrently or sequentially with one or more additional therapeutic agents or with one or more saturating agents designed to prevent clearance of the vectors by the reticular endothelial system.

Where the vector is an AAV vector, the dosage of the vector may be from $1\times10^{10}$ gc/kg to $1\times10^{15}$ gc/kg or more, suitably from $1\times10^{12}$ gc/kg to $1\times10^{14}$ gc/kg, suitably from $5\times10^{12}$ gc/kg to $5\times10^{13}$ gc/kg.

In general, the subject in need thereof will be a mammal, and preferably primate, more preferably a human. Typically, the subject in need thereof will display symptoms characteristic of a disease. The method typically comprises ameliorating the symptoms displayed by the subject in need thereof, by expressing the therapeutic amount of the therapeutic product.

Gene therapy protocols for therapeutic gene expression in target cells in vitro and in vivo, are well-known in the art and will not be discussed in detail here. Briefly, they include intramuscular injection, interstitial injection, instillation in airways, application to endothelium, intra-hepatic parenchyme, and intravenous or intra-arterial administration (e.g. intra-hepatic artery, intra-hepatic vein) of plasmid DNA vectors (naked or in liposomes) or viral vectors. Various devices have been developed for enhancing the availability of DNA to the target cell. While a simple approach is to contact the target cell physically with catheters or implantable materials containing the relevant vector, more complex approaches can use jet injection devices an suchlike. Gene transfer into mammalian liver cells has been performed using both ex vivo and in vivo procedures. The ex vivo approach typically requires harvesting of the liver cells, in vitro transduction with suitable expression vectors, followed by reintroduction of the transduced hepatocytes the liver. In vivo gene transfer has been achieved by injecting DNA or viral vectors into the liver parenchyma, hepatic artery, or portal vein.

According to one preferred embodiment, the methods set out above may be used for the treatment of a subject with haemophilia, e.g. haemophilia A or B. Accordingly, the invention provides a method of treating a subject with haemophilia A or B, the method comprise the steps of:

introducing into the liver of the subject a synthetic liver-specific expression cassette or vector of the present invention which comprises gene encoding a suitable clotting factor (in particular, factor VIII in the case of haemophilia A or factor IX in the case of haemophilia B); and expressing a therapeutic amount of the clotting factor in the liver of said subject.

In some cases, the synthetic liver-specific expression cassette is provided in a vector suitable for gene therapy, preferably an AAV vector.

Preferably the method comprises expressing a suitable amount of the relevant clotting factor in the liver of the subject to alleviate or ameliorate the symptoms of haemophilia A or B.

BRIEF DESCRIPTION OF THE FIGURES

FIG. 3 shows a schematic illustration of further synthetic promoters according to the present invention, with the CRE enhancer elements indicated. These promoters correspond to the promoters of FIG. 1, but with the addition of the "V1" (LVR_CRE0077_V1), "V2" (or LVR_CRE0078_V2) and "A1" (or LVR_CRE0051_AMBP) CRE enhancers.

Figure 1:
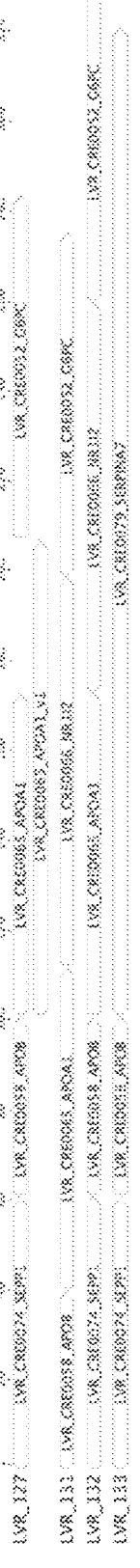
FIG. 1 shows a schematic illustration of synthetic liver-specific promoters according to the present invention, with the CRE enhancer elements indicated.

DETAILED DESCRIPTION OF EMBODIMENTS
OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Ausubel, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); U.S. Pat. No. 4,683,195; Nucleic Acid Hybridization (Harries and Higgins eds. 1984); Transcription and Translation (Hames and Higgins eds. 1984); Culture of Animal Cells (Freshney, Alan R. Liss, Inc., 1987); Immobilized Cells and Enzymes (IRL Press, 1986); Perbal, A Practical Guide to Molecular Cloning (1984); the series, Methods in Enzymology (Abelson and Simon, eds.-in-chief, Academic Press, Inc., New York), specifically, Vols. 154 and 155 (Wu et al. eds.) and Vol. 185, "Gene Expression Technology" (Goeddel, ed.); Gene Transfer Vectors For Mammalian Cells (Miller and Calos eds., 1987, Cold Spring Harbor Laboratory); Immunochemical Methods in Cell and Molecular Biology (Mayer and Walker, eds., Academic Press, London, 1987); Handbook of Experimental Immunology, Vols. I-IV (Weir and Blackwell, eds., 1986); and Manipulating the Mouse Embryo, (Cold Spring Harbor Laboratory Press, Cold Spring Harbor, N.Y., 1986).

To facilitate the understanding of this invention, a number of terms are defined or explained below. Terms used herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "cis-regulatory element" or "CRE", is a term well-known to the skilled person, and means a nucleic acid sequence such as an enhancer, promoter, insulator, or silencer, that can regulate or modulate the transcription of a neighbouring gene (i.e. in cis). CREs are found in the vicinity of the genes that they regulate. CREs typically regulate gene transcription by binding to TFs, i.e. they include TFBS. A single TF may bind to many CREs, and hence control the expression of many genes (pleiotropy). CREs are usually, but not always, located upstream of the transcription start site (TSS) of the gene that they regulate. "Enhancers" are CREs that enhance (i.e. upregulate) the transcription of genes that they are operably associated with, and can be found upstream, downstream, and even within the introns of the gene that they regulate. Multiple enhancers can act in a coordinated fashion to regulate transcription of one gene. "Silencers" in this context relates to CREs that bind TFs called repressors, which act to prevent or downregulate transcription of a gene. The term "silencer" can also refer to a region in the 3' untranslated region of messenger RNA, that bind proteins which suppress translation of that mRNA molecule, but this usage is distinct from its use in describing a CRE. Generally, the CREs of the present invention are liver-specific enhancers (often referred to as liver-specific CREs, or liver-specific CRE enhancers, or suchlike). In the present context, it is preferred that the CRE is located 1500 nucleotides or less from the transcription start site (TSS), more preferably 1000 nucleotides or less from the TSS, more preferably 500 nucleotides or less from the TSS, and suitably 250, 200, 150, or 100 nucleotides or less from the TSS. CREs of the present invention are preferably comparatively short in length, preferably 100 nucleotides or less in length, for example they may be 90, 80, 70, 60 nucleotides or less in length.

The term "cis-regulatory module" or "CRM" means a functional module made up of two or more CREs; in the present invention the CREs are typically liver-specific enhancers. Thus, in the present application a CRM typically comprises a plurality of liver-specific enhancer CREs. Typically, the multiple CREs within the CRM act together (e.g. additively or synergistically) to enhance the transcription of a gene that the CRM is operably associated with. There is conservable scope to shuffle (i.e. reorder), invert (i.e. reverse orientation), and alter spacing in CREs within a CRM. Accordingly, functional variants of CRMs of the present invention include variants of the referenced CRMs wherein CREs within them have been shuffled and/or inverted, and/or the spacing between CREs has been altered.

As used herein, the phrase "promoter" refers to a region of DNA that generally is located upstream of a nucleic acid sequence to be transcribed that is needed for transcription to occur, i.e. which initiates transcription. Promoters permit the proper activation or repression of transcription of a coding sequence under their control. A promoter typically contains specific sequences that are recognized and bound by plurality of TFs. TFs bind to the promoter sequences and result in the recruitment of RNA polymerase, an enzyme that synthesizes RNA from the coding region of the gene. A great many promoters are known in the art.

The term "synthetic promoter" as used herein relates to a promoter that does not occur in nature. In the present context it typically comprises a synthetic CRE and/or CRM of the present invention operably linked to a minimal (or core) promoter or liver-specific proximal promoter. The CREs and/or CRMs of the present invention serve to enhance liver-specific transcription of a gene operably linked to the promoter. Parts of the synthetic promoter may be naturally occurring (e.g. the minimal promoter or one or more CREs in the promoter), but the synthetic promoter as a complete entity is not naturally occurring.

As used herein, "minimal promoter" (also known as the "core promoter") refers to a short DNA segment which is inactive or largely inactive by itself, but can mediate transcription when combined with other transcription regulatory elements. Minimum promoter sequence can be derived from various different sources, including prokaryotic and eukaryotic genes. Examples of minimal promoters are discussed above, and include the dopamine beta-hydroxylase gene minimum promoter, cytomegalovirus (CMV) immediate early gene minimum promoter (CMV-MP), and the herpes thymidine kinase minimal promoter (MinTK). A minimal promoter typically comprises the transcription start site (TSS) and elements directly upstream, a binding site for RNA polymerase II, and general transcription factor binding sites (often a TATA box).

As used herein, "proximal promoter" relates to the minimal promoter plus the proximal sequence upstream of the gene that tends to contain primary regulatory elements. It often extends approximately 250 base pairs upstream of the TSS, and includes specific TFBS. In the present case, the proximal promoter is suitably a naturally occurring liver-specific proximal promoter that can be combined with one or more CREs or CRMs of the present invention. However, the proximal promoter can be synthetic.

A "functional variant" of a cis-regulatory element, cis-regulatory module, promoter or other nucleic acid sequence in the context of the present invention is a variant of a reference sequence that retains the ability to function in the same way as the reference sequence, e.g. as a liver-specific cis-regulatory enhancer element, liver-specific cis-regulatory module or liver-specific promoter. Alternative terms for such functional variants include "biological equivalents" or "equivalents".

It will be appreciated that the ability of a given cis-regulatory element to function as a liver-specific enhancer is determined principally by the ability of the sequence to bind the same liver-specific TFs that bind to the reference sequence. Accordingly, in most cases, a functional variant of a cis-regulatory element will contain TFBS for the same TFs as the reference cis-regulatory element. It is preferred, but not essential, that the TFBS of a functional variant are in the same relative positions (i.e. order) as the reference cis-regulatory element. It is also preferred, but not essential, that the TFBS of a functional variant are in the same orientation as the reference sequence (it will be noted that TFBS can in some cases be present in reverse orientation, e.g. as the reverse complement vis-à-vis the sequence in the reference sequence). It is also preferred, but not essential, that the TFBS of a functional variant are on the same strand as the reference sequence. Thus, in preferred embodiments, the functional variant comprises TFBS for the same TFs, in the same order, in the same orientation and on the same strand as the reference sequence. It will also be appreciated that the sequences lying between TFBS (referred to in some cases as spacer sequences, or suchlike) are of less consequence to the function of the cis-regulatory element. Such sequences can typically be varied considerably, and their lengths can be altered. However, in preferred embodiments the spacing (i.e. the distance between adjacent TFBS) is substantially the same (e.g. it does not vary by more than 20, preferably by not more than 10%, more preferably it is the same) in a functional variant as it is in the reference sequence. It will be apparent that in some cases a functional variant of a cis-regulatory enhancer element can be present in the reverse orientation, e.g. it can be the reverse complement of a cis-regulatory enhancer element as described above, or a variant thereof.

Levels of sequence identity between a functional variant and the reference sequence can also be an indicator or retained functionality. High levels of sequence identity in the TFBS of the cis-regulatory element is of generally higher importance than sequence identity in the spacer sequences (where there is little or no requirement for any conservation of sequence). However, it will be appreciated that even within the TFBS, a considerable degree of sequence variation can be accommodated, given that the sequence of a functional TFBS does not need to exactly match the consensus sequence.

The ability of one or more TFs to bind to a TFBS in a given functional variant can determined by any relevant means known in the art, including, but not limited to, electromobility shift assays (EMSA), binding assays, chromatin immunoprecipitation (ChIP), and ChIP-sequencing (ChIP-seq). In a preferred embodiment the ability of one or more TFs to bind a given functional variant is determined by EMSA. Methods of performing EMSA are well-known in the art. Suitable approaches are described in Sambrook et al. cited above. Many relevant articles describing this procedure are available, e.g. Hellman and Fried, Nat Protoc. 2007; 2(8): 1849-1861.

"Liver-specific" or "liver-specific expression" refers to the ability of a cis-regulatory element, cis-regulatory module or promoter to enhance or drive expression of a gene in the liver (or in liver-derived cells) in a preferential or predominant manner as compared to other tissues (e.g. spleen, muscle, heart, lung, and brain). Expression of the gene can be in the form of mRNA or protein. In preferred embodiments, liver-specific expression is such that there is negligible expression in other (i.e. non-liver) tissues or cells, i.e. expression is highly liver-specific.

The ability of a cis-regulatory element to function as a liver-specific cis-regulatory enhancer element can be readily assessed by the skilled person. The skilled person can thus easily determine whether any variant of the specific cis-regulatory elements recited above remains functional (i.e. it is a functional variant as defined above). For example, any given cis-regulatory element to be assessed can be operably linked to a minimal promoter (e.g. positioned upstream of CMV-MP) and the ability of the cis-regulatory element to drive liver-specific expression of a gene (typically a reporter gene) is measured. Alternatively, a variant of a cis-regulatory enhancer element can be substituted into a synthetic liver-specific promoter in place of a reference cis-regulatory enhancer element, and the effects on liver-specific expression driven by said modified promoter can be determined and compared to the unmodified form. Similarly, the ability of a cis-regulatory module or promoter to drive liver-specific expression can be readily assessed by the skilled person (e.g. as described in the examples below). Expression levels of a gene driven by a variant of a reference promoter can be compared to the expression levels driven by the reference sequence. In some embodiments, where liver-specific expression levels driven by a variant promoter are at least 50%, at least 60%, at least 70%, at least 80%, at least 90%, or at least 100% of the expression levels driven by the reference promoter, it can be said that the variant remains functional. Suitable nucleic acid constructs and reporter assays to assess liver-specific expression enhancement can easily constructed, and the examples set out below give suitable methodologies.

Liver-specificity can be identified wherein the expression of a gene (e.g. a therapeutic or reporter gene) occurs preferentially or predominantly in liver-derived cells. Preferential or predominant expression can be defined, for example, where the level of expression is significantly greater in liver-derived cells than in other types of cells (i.e. non-liver-derived cells). For example, expression in liver-derived cells is suitably at least 5-fold higher than non-liver cells, preferably at least 10-fold higher than non-liver cells, and it may be 50-fold higher or more in some cases. For convenience, liver-specific expression can suitably be demonstrated via a comparison of expression levels in a hepatic cell line (e.g. liver-derived cell line such as Huh7 and/or HepG2 cells) or liver primary cells, compared with expression levels in a kidney-derived cell line (e.g. HEK-293), a cervical tissue-derived cell line (e.g. HeLa) and/or a lung-derived cell line (e.g. A549).

The synthetic liver-specific promoters of the present invention preferably have a reduced expression at a level of at least 4-fold less than the CMV-IE promoter in non-liver-derived cells, suitably in HEK-293, HeLa, and/or A549 cells. Suitably this is compared to a non-tissue specific promoter such as CMV-IE. The synthetic liver-specific promoters of the present invention preferably have an activity of 50% or less than the CMV-IE promoter in non-liver-derived cells (suitably in HEK-293, HeLa, and/or A549 cells), suitably 25% or less, 20% or less, 15% or less, 10% or less, 5% or less or 1% or less. Generally, it is preferred that expression in non-liver-derived cells is minimized, but in some cases this may not be necessary. In some embodiments, the synthetic liver-specific promoters of the present invention are suitable for promoting gene expression at a level of at 50% or less than an LP1 promoter in non-liver-derived cells (e.g. HEK-293, HeLa, and/or A549 cells).

The synthetic liver-specific promoters of the present invention are preferably suitable for promoting expression in the liver of a subject, e.g. driving liver-specific expression of a transgene, preferably a therapeutic transgene. In some embodiments, the liver-specific promoters of the invention are suitable for promoting liver-specific transgene expression at a level at least 1.5-fold greater than the LP1 promoter, preferably 2-fold greater than the LP1 promoter, more preferably 3-fold greater than the LP1 promoter, and yet more preferably 5-fold greater than the LP1 promoter. Such expression is suitably determined in liver-derived cells, e.g. in Huh7, and/or HepG2 cells or primary liver cells (suitably primary human hepatocytes). In some embodiments, the synthetic liver-specific promoters of the present invention are suitable for promoting gene expression at a level of at least 1.5-fold less than an LP1 promoter in non-liver-derived cells (e.g. HEK-293, HeLa, and/or A549 cells).

Preferred synthetic liver-specific promoters of the present invention are suitable for promoting liver-specific transgene expression and have an activity in liver cells which is at least 15%, 20%, 30%, 40%, 50%, 60%, 70%, 80%, 90%, 100%, 125%, 150%, 175%, 200%, 250%, 300%, 350% or 400% of the activity of the TBG promoter.

The synthetic liver-specific promoters of the present invention are preferably suitable for promoting liver-specific expression at a level at least 1.5-fold greater than a CMV-IE promoter in liver-derived cells, preferably at least 2-fold greater than a CMV promoter in liver-derived cells (e.g. HEK-293, HeLa, and/or A549 cells).

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA RNA hybrid molecules, specifically including hnRNA, pre-mRNA, mRNA, cDNA, genomic DNA, amplification products, oligonucleotides, and synthetic (e.g., chemically synthesised) DNA, RNA or DNA RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

The terms "identity" and "identical" and the like refer to the sequence similarity between two polymeric molecules, e.g., between two nucleic acid molecules, such as between two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method. Typically, the percentage sequence identity is calculated over the entire length of the sequence.

For example, a global optimal alignment is suitably found by the Needleman-Wunsch algorithm with the following scoring parameters: Match score: +2, Mismatch score: −3; Gap penalties: gap open 5, gap extension 2. The percentage identity of the resulting optimal global alignment is suitably calculated by the ratio of the number of aligned bases to the total length of the alignment, where the alignment length includes both matches and mismatches, multiplied by 100.

The term "hybridising" means annealing to two at least partially complementary nucleotide sequences in a hybridization process. In order to allow hybridisation to occur complementary nucleic acid molecules are generally thermally or chemically denatured to melt a double strand into two single strands and/or to remove hairpins or other secondary structures from single-stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and Na-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. By way of non-limiting example, representative salt and temperature conditions for stringent hybridization are: 1×SSC, 0.5% SDS at 65° C. The abbreviation SSC refers to a buffer used in nucleic acid hybridization solutions. One litre of a 20× (twenty times concentrate) stock SSC buffer solution (pH 7.0) contains 175.3 g sodium chloride and 88.2 g sodium citrate. A representative time period for achieving hybridisation is 12 hours.

The meaning of "consensus sequence" is well-known in the art. In the present application, the following notation is used for the consensus sequences, unless the context dictates otherwise. Considering the following exemplary DNA sequence:

A[CT]N{A}YR

A means that an A is always found in that position; [CT] stands for either C or T in that position; N stands for any base in that position; and {A} means any base except A is found in that position. Y represents any pyrimidine, and R indicates any purine.

"Synthetic" in the present application means a nucleic acid molecule that does not occur in nature. Synthetic nucleic acid expression constructs of the present invention are produced artificially, typically by recombinant technologies. Such synthetic nucleic acids may contain naturally occurring sequences (e.g. promoter, enhancer, intron, and other such regulatory sequences), but these are present in a non-naturally occurring context. For example, a synthetic gene (or portion of a gene) typically contains one or more nucleic acid sequences that are not contiguous in nature (chimeric sequences), and/or may encompass substitutions, insertions, and deletions and combinations thereof.

"Complementary" or "complementarity", as used herein, refers to the Watson-Crick base-pairing of two nucleic acid sequences. For example, for the sequence 5'-AGT-3' binds to the complementary sequence 3'-TCA-5'. Complementarity between two nucleic acid sequences may be "partial", in which only some of the bases bind to their complement, or it may be complete as when every base in the sequence binds to its complementary base. The degree of complementarity between nucleic acid strands has significant effects on the efficiency and strength of hybridisation between nucleic acid strands.

"Transfection" in the present application refers broadly to any process of deliberately introducing nucleic acids into cells, and covers introduction of viral and non-viral vectors, and includes transformation, transduction and like terms and processes. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); Agrobacterium-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

As used herein, the phrase "transgene" refers to an exogenous nucleic acid sequence. In one example, a transgene is a gene encoding an industrially or pharmaceutically useful compound, or a gene encoding a desirable trait. In yet another example, the transgene encodes an antisense nucleic acid sequence, wherein expression of the antisense nucleic acid sequence inhibits expression of a target nucleic acid sequence.

The term "vector" is well known in the art, and as used herein refers to a nucleic acid molecule, e.g. double-stranded DNA, which may have inserted into it a nucleic acid sequence according to the present invention. A vector is suitably used to transport an inserted nucleic acid molecule into a suitable host cell. A vector typically contains all of the necessary elements that permit transcribing the insert nucleic acid molecule, and, preferably, translating the transcript into a polypeptide. A vector typically contains all of the necessary elements such that, once the vector is in a host cell, the vector can replicate independently of, or coincidental with, the host chromosomal DNA; several copies of the vector and its inserted nucleic acid molecule may be generated. Vectors of the present invention can be episomal vectors (i.e., that do not integrate into the genome of a host cell), or can be vectors that integrate into the host cell genome. This definition includes both non-viral and viral vectors. Non-viral vectors include but are not limited to plasmid vectors (e.g. pMA-RQ, pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Larger vectors such as artificial chromosomes (bacteria (BAC), yeast (YAC), or human (HAC)) may be used to accommodate larger inserts. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

The term "operably linked", "operably connected" or equivalent expressions as used herein refer to the arrangement of various nucleic acid elements relative to each such that the elements are functionally connected and are able to interact with each other in the manner intended. Such elements may include, without limitation, a promoter, an enhancer and/or a regulatory element, a polyadenylation sequence, one or more introns and/or exons, and a coding sequence of a gene of interest to be expressed. The nucleic acid sequence elements, when properly oriented or operably linked, act together to modulate the activity of one another, and ultimately may affect the level of expression of an expression product. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, cis-regulatory elements will typically be located immediately upstream of the promoter (although this is generally the case, it should definitely not be interpreted as a limitation or exclusion of positions within the nucleic acid expression cassette), but this needs not be the case in vivo, e.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

A "spacer sequence" or "spacer" as used herein is a nucleic acid sequence that separates two functional nucleic acid sequences (e.g. TFBS, CREs, CRMs etc.). It can have essentially any sequence, provided it does not prevent the functional nucleic acid sequence (e.g. cis-regulatory element) from functioning as desired (e.g. this could happen if it includes a silencer sequence, prevents binding of the desired transcription factor, or suchlike). Typically, it is non-functional, as in it is present only to space adjacent functional nucleic acid sequences from one another.

The term "pharmaceutically acceptable" as used herein is consistent with the art and means compatible with the other ingredients of the pharmaceutical composition and not deleterious to the recipient thereof.

"Therapeutically effective amount" and like phrases mean a dose or plasma concentration in a subject that provides the desired specific pharmacological effect, e.g. to express a therapeutic gene in the liver. It is emphasized that a therapeutically effective amount may not always be effective in treating the conditions described herein, even though such dosage is deemed to be a therapeutically effective amount by those of skill in the art. The therapeutically effective amount may vary based on the route of administration and dosage form, the age and weight of the subject, and/or the disease or condition being treated.

The terms "treatment" or "treating" refer to reducing, ameliorating or eliminating one or more signs, symptoms, or effects of a disease or condition.

The terms "individual," "subject," and "patient" are used interchangeably, and refer to any individual subject with a disease or condition in need of treatment. For the purposes of the present disclosure, the subject may be a primate, preferably a human, or another mammal, such as a dog, cat, horse, pig, goat, or bovine, and the like.

Example 1—Sequences

The following sequences are of relevance to the present invention:

TABLE 1

| Cis-regulatory elements (CREs): | |
|---|---|
| Name | Sequence |
| A1(alpha mic/bikor LVR_CRE0051_AMBP) | AGGTTAATTTTTAAAAAGCAGTCAAAAGTCCAAGTGGCCCTTGGC AGCATTTACTCTCTCTGTTTGCTCTGGTTAATAATCTCAGGAGCA CAAACATTCC (SEQ ID NO: 1) |
| V1(LVR_CRE0077_V1) | AAGCAAATATTTGTGGTTATGGATTAACTCGAACTGTTTGCCCAC TCTATTTGCCC (SEQ ID NO: 2) |
| V2(LVR_CRE0078_V2) | GGCGCCCTTTGGACCTTTTGCAATCCTGGAGCAAACAGCAAACAC (SEQ ID NO: 3) |
| LVR_CRE0074_SEPP1 | AGAATGAACATTGAACTTTGGACTATACCTGAGGGGTGAGGTAAA CAACAGGACTATAAAT (SEQ ID NO: 4) |
| LVR_CRE0058_APOB | GGCCCGGGAGGCGCCCTTTGGACCTTTTGCAATCCTGGCG (SEQ ID NO: 5) |
| LVR_CRE0065_APOA1 | CACTGAACCCTTGACCCCTGCCCTGCAGCCCCCGCAGCTTGCTGT TTGCCCACTCTATTTGCCCAGCCCCAG (SEQ ID NO: 6) |
| LVR_CRE0065_APOA1_v1 | CACTGAACCCTTGACCCCTGCCCTGCAGCCCCCGCAGCTTGCTGT TTGCCCACTCTATTTGCCCAGCCCCAGGGACAGAGCTGATCCTTG AACTCTTAAGTTCCAC (SEQ ID NO: 7) |
| LVR_CRE0066_NR1I2 | CCCTGGAGAGTCCTTTAGCAGGGCAAAGTGCAACATAGGCAGACC TTAAGGGATGACTCAGTAACAGATAAGCTTTGTGTGCCTGCA (SEQ ID NO: 8) |

TABLE 2

| Minimal/Proximal Promoters: | |
|---|---|
| Name | Sequence |
| LVR_CRE0052_G6PC | GGGCATATAAAACAGGGGCAAGGCACAGACTCATAGCAGAGCAAT CACCACCAAGCCTGGAATAACTGCAGCCACC (SEQ ID NO: 9) |

TABLE 2-continued

Minimal/Proximal Promoters:

| Name | Sequence |
|---|---|
| SERPINA7 proximal promoter (LVR_CRE0079_SERPINA7) | CTCTTTTGTTTTACATGAAGGGTCTGGCAGCCAAAGCAATCACTC AAAGTTCAAACCTTATCATTTTTTGCTTTGTTCCTCTTGGCCTTG GTTTTGTACATCAGCTTTGAAAATACCATCCCAGGGTTAATGCTG GGGTTAATTTATAACTAAGAGTGCTCTAGTTTTGCAATACAGGAC ATGCTATAAAAATGGAAAGATGTTGCTTTCTGAGAGATGCGCCAC C (SEQ ID NO: 10) |

TABLE 3

Component parts of V1 (LVR_CRE0077_V1):

| Name | Sequence |
|---|---|
| LVR_CRE0080_PROC | AAGCAAATATTTGTGGTTATGGATTAACTCGAA (SEQ ID NO: 11) |
| LVR_CRE0081_APOA1 | CTGTTTGCCCACTCTATTTGCCC (SEQ ID NO: 12) |

TABLE 4

Component parts of V2 (LVR_CRE0078_V2):

| Name | Sequence |
|---|---|
| LVR_CRE0061_APOB | GGCGCCCTTTGGACCTTTTGCAATCCTGG (SEQ ID NO: 13) |
| LVR_CRE0082_APOC4 | AGCAAACAGCAAACAC (SEQ ID NO: 14) |

TABLE 5

TFBS in A1 (LVR_CRE0051_AMBP)(TFBS shown in bold):

| A1 (LVR_CRE0051_AMBP) | AGGGTTAATTTTTAAAAAGCAGTCAAAAGTCCAAGTGGCCCTTGGCAGCATTTA CTCTCTCTGTTTGCTCTGGTTAATAATCTCAGGAGCACAAACATTCC (SEQ ID NO: 1) | | |
|---|---|---|---|
| TF | TFBS sequence | Position (SEQ ID NO:) | |
| HNF1 | 3..15 | GTTAATTTTTAAA(74) | |
| HNF4 | 34..44 | GTGGCCCTTGG(75) | |
| HNF3 | 61..67 | TGTTTGC(76) | |
| HNF1 | 70..84 | TGGTTAATAATCTCA(77) | |
| HNF3 | 90..96 | ACAAACA(78) | |

TABLE 6

TFBS in V1 (TFBS shown in bold):

| V1 | AAGCAAATATTTGTGGTTATGGATTAACTCGAA CTGTTTGCCCACTCTATTTGCCC (SEQ ID NO: 2) | |
|---|---|---|
| TF | Position | TFB Ssequence(SEQ ID NO:) |
| HNF3 | 2..12 | AGCAAATATTT(49) |
| HNF3 | 5..16 | AAATATTTGTGG(50) |

TABLE 6-continued

TFBS in V1 (TFBS shown in bold):

| | | |
|---|---|---|
| HNF1 | 15..29 | GGTTATGGATTAACT(51) |
| HNF3 | 34..43 | CTGTTTGCCC(52) |
| HNF3 | 47..56 | CTATTTGCCC(53) |

TABLE 7

TFBS in V2 (TFBS shown in bold):

| V2 | GGCGCCCTTTGGACCTTTTGCAATCCTGGA GCAAACAGCAAACAC (SEQ ID NO: 3) | |
|---|---|---|
| TF | TFBS sequence | Position |
| HNF4 | 3..15 | CGCCCTTTGGACC(54) |
| c/EBP | 12..29 | GACCTTTTGCAATCCTGG(55) |

TABLE 7-continued

TFBS in V2 (TFBS shown in bold):

| | | |
|---|---|---|
| HNF3 | 30..38 | CTGTTTGCT(56) |
| HNF3 | 36..45 | GTGTTTGCTG(57) |

TABLE 8

| TFBS in LVR_CRE0074_SEPP1 (TFBS shown in bold): | | |
| --- | --- | --- |
| LVR_CRE0074_SEPP1 | AGAATGAACATTGAACTTTGGACTATACC TGAGGGGTGAGGTAAACAACAGGACTATA AAT (SEQ ID NO: 4) | |

| TF | TFBS sequence | Position |
| --- | --- | --- |
| HNF4 | 7..25 | AACATTGAACTTTGGAC TA(58) |
| FoxO1a | 41..48 | GTAAACAA(59) |

TABLE 9

| TFBS in LVR_CRE0058_APOB (TFBS shown in bold): | |
| --- | --- |
| LVR_CRE0058_APOB | GGCCCGGGAGGGCGCCCTTTGGACCTTTTGC AATCCTGGCG (SEQ ID NO: 5) |

TABLE 9-continued

| TFBS in LVR_CRE0058_APOB (TFBS shown in bold): | | |
| --- | --- | --- |
| TF | Position | TFBS sequence |
| HNF4 | 12..24 | CGCCCTTTGGACC(60) |
| c/EBP | 21..38 | GACCTTTTGCAATCCTGG(61) |

TABLE 10

| TFBS in LVR_CRE0065 APOA1 (TFBS shown in bold): | | |
| --- | --- | --- |
| LVR_CRE0065_APOA1 | CACTGAACCCTTGACCCCTGCCCTGC AGCCCCCGCAGCTTGCTGTTTGCCCA CTCTATTTGCCCAGCCCCAG (SEQ ID NO: 6) | |

| TF | Position | TFBS sequence |
| --- | --- | --- |
| RXR Alpha | 2..24 | ACTGAACCCTTGACCCCTG CCCT(62) |
| HNF3 | 42..51 | CTGTTTGCCC(63) |
| HNF3 | 55..64 | CTATTTGCCC(53) |

TABLE 11

| TFBS in LVR_CRE0065 APOA1_v1 (TFBS shown in bold): | | |
| --- | --- | --- |
| LVR_CRE0065_APOA1_v1 | CACTGAACCCTTGACCCCTGCCCTGCAGCCCCCG CAGCTTGCTGTTTGCCCACTCTATTTGCCCAGCCCC AGGGACAGAGCTGATCCTTGAACTCTTAAGTTCCAC (SEQ ID NO: 7) | |

| TF | Position | TFBS sequence |
| --- | --- | --- |
| RXR Alpha | 2..24 | ACTGAACCCTTGACCCCTGCCCT(62) |
| HNF3 | 42..51 | CTGTTTGCCC(63) |
| HNF3 | 55..64 | CTATTTGCCC(53) |
| HNF4 | 82..96 | TGATCCTTGAACTCT(64) |

TABLE 12

| TFBS in LVR_CRE0066 NR1I2 (TFBS shown in bold): | | |
| --- | --- | --- |
| LVR_CRE0066_NR1I2 | CCCTGGAGAGTCCTTTAGCAGGGCAAAGT GCAACATAGGCAGACCTTAAGGGGATGACT CAGTAACAGATAAGCTTTGTGTGCCTGCA (SEQ ID NO: 8) | |

| TF | Position | TFBS sequence |
| --- | --- | --- |
| HNF4G | 18..32 | GCAGGGCAAAGTGCA (SEQ ID NO: 79) |
| FOS::JUN | 52..61 | GATGACTCAG (SEQ ID NO: 80) |

TABLE 13

Cis-regulatory modules (CRMs):

| Name | Sequence |
| --- | --- |
| CRM_LVR_127 | AGAATGAACATTGAACTTTGGACTATACCTGAGGGGTGAGGTAAACAACAGGACTATAAATGGCC<br>CGGGAGGCGCCCTTTGGACCTTTTGCAATCCTGGCGCACTGAACCCTTGACCCCTGCCCTGCAGCC<br>CCCGCAGCTGCTGTTTGCCCACTCTATTTGCCCAGCCCCAGGGACAGAGCTGATCCTTGAACTCTT<br>AAGTTCCAC<br>(SEQ ID NO: 15) |
| CRM_LVR_127_A1 | AGGTTAATTTTTAAAAAGCAGTCAAAAGTCCAAGTGGCCCTTGGCAGCATTTACTCTCTCTGTTTG<br>CTCTGGTTAATAATCTCAGGAGCACAAACATTCCTGTACCAGAATGAACATTGAACTTTGGACTAT<br>ACCTGAGGGGTGAGGTAAACAACAGGACTATAAATGGCCCGGGAGGCGCCCTTTGGACCTTTTG<br>CAATCCTGGCGCACTGAACCCTTGACCCCTGCCCTGCAGCCCCCGCAGCTTGCTGTTTGCCCACTCT<br>ATTTGCCCAGCCCCAGGGACAGAGCTGATCCTTGAACTCTTAAGTTCCAC<br>(SEQ ID NO: 16) |
| CRM_LVR_127_V1 | AAGCAAATATTTGTGGTTATGGATTAACTCGAACTGTTTGCCCACTCTATTTGCCCTGTACCAGAAT<br>GAACATTGAACTTTGGACTATACCTGAGGGGTGAGGTAAACAACAGGACTATAAATGGCCCGGG<br>AGGCGCCCTTTGGACCTTTTGCAATCCTGGCGCACTGAACCCTTGACCCCTGCCCTGCAGCCCCCG<br>CAGCTGCTGTTTGCCCACTCTATTTGCCCAGCCCCAGGGACAGAGCTGATCCTTGAACTCTTAAG<br>TTCCAC<br>(SEQ ID NO: 17) |
| CRM_LVR_127_V2 | GGCGCCCTTTGGACCTTTTGCAATCCTGGAGCAAACAGCAAACACTGTACCAGAATGAACATTGA<br>ACTTTGGACTATACCTGAGGGGTGAGGTAAACAACAGGACTATAAATGGCCCGGGAGGCGCCCT<br>TTGGACCTITTGCAATCCTGGCGCACTGAACCCTTGACCCCTGCCCTGCAGCCCCCGCAGCTGCT<br>GTTTGCCCACTCTATTTGCCCAGCCCCAGGGACAGAGCTGATCCTTGAACTCTTAAGTTCCAC<br>(SEQ ID NO: 18) |
| CRM_LVR_131 | GGCCCGGGAGGCGCCCTTTGGACCTTTTGCAATCCTGGCGCACTGAACCCTTGACCCCTGCCCTGC<br>AGCCCCCGCAGCTTGCTGTTTGCCCACTCTATTTGCCCAGCCCCAGCCCTGGAGAGTCCTTTAGCA<br>GGGCAAAGTGCAACATAGGCAGACCTTAAGGGATGACTCAGTAACAGATAAGCTTTGTGTGCCTG<br>CA<br>(SEQ ID NO: 19) |
| CRM_LVR_131_A1 | AGGTTAATTTTTAAAAAGCAGTCAAAAGTCCAAGTGGCCCTTGGCAGCATTTACTCTCTCTGTTTG<br>CTCTGGTTAATAATCTCAGGAGCACAAACATTCCTGTACCGGCCCGGGAGGCGCCCTTTGGACCTT<br>TTGCAATCCTGGCGCACTGAACCCTTGACCCCTGCCCTGCAGCCCCCGCAGCTTGCTGTTTGCCCA<br>CTCTATTTGCCCAGCCCCAGCCCTGGAGAGTCCTTTAGCAGGGCAAAGTGCAACATAGGCAGACC<br>TTAAGGGATGACTCAGTAACAGATAAGCTTTGTGTGCCTGCA<br>(SEQ ID NO: 20) |
| CRM_LVR_131_V1 | AAGCAAATATTTGTGGTTATGGATTAACTCGAACTGTTTGCCCACTCTATTTGCCCTGTACCGGCCC<br>GGGAGGCGCCCTTTGGACCTTTTGCAATCCTGGCGCACTGAACCCTTGACCCCTGCCCTGCAGCCC<br>CCGCAGCTTGCTGTTTGCCCACTCTATTTGCCCAGCCCCAGCCCTGGAGAGTCCTTTAGCAGGGCA<br>AAGTGCAACATAGGCAGACCTTAAGGGATGACTCAGTAACAGATAAGCTTTGTGTGCCTGCA<br>(SEQ ID NO: 21) |
| CRM_LVR_131_V2 | GGCGCCCTTTGGACCTTTTGCAATCCTGGAGCAAACAGCAAACACTGTACCGGCCCGGGAGGCGC<br>CCTTTGGACCTTTTGCAATCCTGGCGCACTGAACCCTTGACCCCTGCCCTGCAGCCCCCGCAGCTTG<br>CTGTTTGCCCACTCTATTTGCCCAGCCCCAGCCCTGGAGAGTCCTTTAGCAGGGCAAAGTGCAACA<br>TAGGCAGACCTTAAGGGATGACTCAGTAACAGATAAGCTTTGTGTGCCTGCA<br>(SEQ ID NO: 22) |
| CRM_LVR_132 | AGAATGAACATTGAACTTTGGACTATACCTGAGGGGTGAGGTAAACAACAGGACTATAAATGGCC<br>CGGGAGGCGCCCTTTGGACCTTTTGCAATCCTGGCGCACTGAACCCTTGACCCCTGCCCTGCAGCC<br>CCCGCAGCTGCTGTTTGCCCACTCTATTTGCCCAGCCCCAGCCCTGGAGAGTCCTTTAGCAGGGC<br>AAAGTGCAACATAGGCAGACCTTAAGGGATGACTCAGTAACAGATAAGCTTTGTGTGCCTGCA<br>(SEQ ID NO: 23) |
| CRM_LVR_132_A1 | AGGTTAATTTTTAAAAAGCAGTCAAAAGTCCAAGTGGCCCTTGGCAGCATTTACTCTCTCTGTTTG<br>CTCTGGTTAATAATCTCAGGAGCACAAACATTCCTGTACCAGAATGAACATTGAACTTTGGACTAT<br>ACCTGAGGGGTGAGGTAAACAACAGGACTATAAATGGCCCGGGAGGCGCCCTTTGGACCTTTTG<br>CAATCCTGGCGCACTGAACCCTTGACCCCTGCCCTGCAGCCCCCGCAGCTTGCTGTTTGCCCACTCT<br>ATTTGCCCAGCCCCAGCCCTGGAGAGTCCTTTAGCAGGGCAAAGTGCAACATAGGCAGACCTTAA<br>GGGATGACTCAGTAACAGATAAGCTTTGTGTGCCTGCA<br>(SEQ ID NO: 24) |
| CRM_LVR_132_V1 | AAGCAAATATTTGTGGTTATGGATTAACTCGAACTGTTTGCCCACTCTATTTGCCCTGTACCAGAAT<br>GAACATTGAACTTTGGACTATACCTGAGGGGTGAGGTAAACAACAGGACTATAAATGGCCCGGG<br>AGGCGCCCTTTGGACCTTTTGCAATCCTGGCGCACTGAACCCTTGACCCCTGCCCTGCAGCCCCCG<br>CAGCTGCTGTTTGCCCACTCTATTTGCCCAGCCCCAGCCCTGGAGAGTCCTTTAGCAGGGCAAAG<br>TGCAACATAGGCAGACCTTAAGGGATGACTCAGTAACAGATAAGCTTTGTGTGCCTGCA<br>(SEQ ID NO: 25) |

TABLE 13-continued

Cis-regulatory modules (CRMs):

| Name | Sequence |
|---|---|
| CRM_LVR_132_V2 | GGCGCCCTTTGGACCTTTTGCAATCCTGGAGCAAACAGCAAACACTGTACCAGAATGAACATTGA ACTTTGGACTATACCTGAGGGGTGAGGTAAACAACAGGACTATAAATGGCCCGGGAGGCGCCCT TTGGACCTITTGCAATCCTGGCGCACTGAACCCTTGACCCCTGCCCTGCAGCCCCCGCAGCTGCT GTTTGCCCACTCTATTTGCCCAGCCCCAGCCCTGGAGAGTCCTTTAGCAGGGCAAAGTGCAACATA GGCAGACCTTAAGGGATGACTCAGTAACAGATAAGCTTTGTGTGCCTGCA<br>(SEQ ID NO: 26) |
| CRM_LVR_133 | AGAATGAACATTGAACTTTGGACTATACCTGAGGGGTGAGGTAAACAACAGGACTATAAATGGCC CGGGAGGCGCCCTTTGGACCTTTTGCAATCCTGGCG<br>(SEQ ID NO: 27) |
| CRM_LVR_133_A1 | AGGTTAATTTTTAAAAAGCAGTCAAAAGTCCAAGTGGCCCTTGGCAGCATTTACTCTCTCTGTTTG CTCTGGTTAATAATCTCAGGAGCACAAACATTCCTGTACCAGAATGAACATTGAACTTTGGACTAT ACCTGAGGGGTGAGGTAAACAACAGGACTATAAATGGCCCGGGAGGCGCCCTTTGGACCTTTTG CAATCCTGGCG<br>(SEQ ID NO: 28) |
| CRM_LVR_133_V1 | AAGCAAATATTTGTGGTTATGGATTAACTCGAACTGTTTGCCCACTCTATTTGCCCTGTACCAGAAT GAACATTGAACTTTGGACTATACCTGAGGGGTGAGGTAAACAACAGGACTATAAATGGCCCGGG AGGCGCCCTTTGGACCTTTTGCAATCCTGGCG<br>(SEQ ID NO: 29) |
| CRM_LVR_133_V2 | GGCGCCCTTTGGACCTTTTGCAATCCTGGAGCAAACAGCAAACACTGTACCAGAATGAACATTGA ACTTTGGACTATACCTGAGGGGTGAGGTAAACAACAGGACTATAAATGGCCCGGGAGGCGCCCT TTGGACCTTTTGCAATCCTGGCG<br>(SEQ ID NO: 30) |

TABLE 14

Synthetic Promoters:

| Name | Sequence |
|---|---|
| LVR_127 | AGAATGAACATTGAACTTTGGACTATACCTGAGGGGTGAGGTAAACAACAGGACTATAAATGGCC CGGGAGGCGCCCTTTGGACCTTTTGCAATCCTGGCGCACTGAACCCTTGACCCCTGCCCTGCAGCC CCCGCAGCTGCTGTTTGCCCACTCTATTTGCCCAGCCCCAGGGACAGAGCTGATCCTTGAACTCTT AAGTTCCACGGGCATATAAAACAGGGGCAAGGCACAGACTCATAGCAGAGCAATCACCACCAAG CCTGGAATAACTGCAGCCACC<br>(SEQ ID NO: 31) |
| LVR_127_A1 | AGGTTAATTTTTAAAAAGCAGTCAAAAGTCCAAGTGGCCCTTGGCAGCATTTACTCTCTCTGTTTG CTCTGGTTAATAATCTCAGGAGCACAAACATTCCTGTACCAGAATGAACATTGAACTTTGGACTAT ACCTGAGGGGTGAGGTAAACAACAGGACTATAAATGGCCCGGGAGGCGCCCTTTGGACCTTTTG CAATCCTGGCGCACTGAACCCTTGACCCCTGCCCTGCAGCCCCCGCAGCTTGCTGTTTGCCCACTCT ATTTGCCCAGCCCCAGGGACAGAGCTGATCCTTGAACTCTTAAGTTCCACGGGCATATAAAACAG GGGCAAGGCACAGACTCATAGCAGAGCAATCACCACCAAGCCTGGAATAACTGCAGCCACC<br>(SEQ ID NO: 32) |
| LVR_127_V1 | AAGCAAATATTTGTGGTTATGGATTAACTCGAACTGTTTGCCCACTCTATTTGCCCTGTACCAGAAT GAACATTGAACTTTGGACTATACCTGAGGGGTGAGGTAAACAACAGGACTATAAATGGCCCGGG AGGCGCCCTTTGGACCTTTTGCAATCCTGGCGCACTGAACCCTTGACCCCTGCCCTGCAGCCCCCG CAGCTGCTGTTTGCCCACTCTATTTGCCCAGCCCCAGGGACAGAGCTGATCCTTGAACTCTTAAG TTCCACGGGCATATAAAACAGGGGCAAGGCACAGACTCATAGCAGAGCAATCACCACCAAGCCT GGAATAACTGCAGCCACC<br>(SEQ ID NO: 33) |
| LVR_127_V2 | GGCGCCCTTTGGACCTTTTGCAATCCTGGAGCAAACAGCAAACACTGTACCAGAATGAACATTGA ACTTTGGACTATACCTGAGGGGTGAGGTAAACAACAGGACTATAAATGGCCCGGGAGGCGCCCT TTGGACCTITTGCAATCCTGGCGCACTGAACCMGACCCCTGCCCTGCAGCCCCCGCAGCTGCT GTTTGCCCACTCTATTTGCCCAGCCCCAGGGACAGAGCTGATCCTTGAACTCTTAAGTTCCACGGG CATATAAAACAGGGGCAAGGCACAGACTCATAGCAGAGCAATCACCACCAAGCCTGGAATAACT GCAGCCACC<br>(SEQ ID NO: 34) |
| LVR_131 | GGCCCGGGAGGCGCCCTTTGGACCTTTTGCAATCCTGGCGCACTGAACCCTTGACCCCTGCCCTGC AGCCCCCGCAGCTTGCTGTTTGCCCACTCTATTTGCCCAGCCCCAGCCCTGGAGAGTCCTTTAGCA GGGCAAAGTGCAACATAGGCAGACCTTAAGGGATGACTCAGTAACAGATAAGCTTTGTGTGCCTG CAGGGCATATAAAACAGGGGCAAGGCACAGACTCATAGCAGAGCAATCACCACCAAGCCTGGAA TAACTGCAGCCACC<br>(SEQ ID NO: 35) |

TABLE 14-continued

| | |
|---|---|

Synthetic Promoters:

| Name | Sequence |
|---|---|

LVR_131_A1    AGGTTAATTTTTAAAAAGCAGTCAAAAGTCCAAGTGGCCCTTGGCAGCATTTACTCTCTCTGTTTG
CTCTGGTTAATAATCTCAGGAGCACAAACATTCCTGTACCGGCCCGGGAGGCGCCCTTTGGACCTT
TTGCAATCCTGGCGCACTGAACCCTTGACCCCTGCCCTGCAGCCCCCGCAGCTTGCTGTTTGCCCA
CTCTATTTGCCCAGCCCCAGCCCTGGAGAGTCCTTTAGCAGGGCAAAGTGCAACATAGGCAGACC
TTAAGGGATGACTCAGTAACAGATAAGCTTTGTGTGCCTGCAGGGCATATAAAACAGGGGCAAG
GCACAGACTCATAGCAGAGCAATCACCACCAAGCCTGGAATAACTGCAGCCACC
(SEQ ID NO: 36)

LVR_131_V1    AAGCAAATATTTGTGGTTATGGATTAACTCGAACTGTTTGCCCACTCTATTTGCCCTGTACCGGCCC
GGGAGGCGCCCTTTGGACCTTTTGCAATCCTGGCGCACTGAACCCTTGACCCCTGCCCTGCAGCCC
CCGCAGCTTGCTGTTTGCCCACTCTATTTGCCCAGCCCCAGCCCTGGAGAGTCCTTTAGCAGGGCA
AAGTGCAACATAGGCAGACCTTAAGGGATGACTCAGTAACAGATAAGCTTTGTGTGCCTGCAGGG
CATATAAAACAGGGGCAAGGCACAGACTCATAGCAGAGCAATCACCACCAAGCCTGGAATAACT
GCAGCCACC
(SEQ ID NO: 37)

LVR_131_V2    GGCGCCCTTTGGACCTTTTGCAATCCTGGAGCAAACAGCAAACACTGTACCGGCCCGGGAGGCGC
CCTTTGGACCTTTTGCAATCCTGGCGCACTGAACCCTTGACCCCTGCCCTGCAGCCCCCGCAGCTG
CTGTTTGCCCACTCTATTTGCCCAGCCCCAGCCCTGGAGAGTCCTTTAGCAGGGCAAAGTGCAACA
TAGGCAGACCTTAAGGGATGACTCAGTAACAGATAAGCTTTGTGTGCCTGCAGGGCATATAAAAC
AGGGGCAAGGCACAGACTCATAGCAGAGCAATCACCACCAAGCCTGGAATAACTGCAGCCACC
(SEQ ID NO: 38)

LVR_132    AGAATGAACATTGAACTTTGGACTATACCTGAGGGGTGAGGTAAACAACAGGACTATAAATGGCC
CGGGAGGCGCCCTTTGGACCTTTTGCAATCCTGGCGCACTGAACCCTTGACCCCTGCCCTGCAGCC
CCCGCAGCTGCTGTTTGCCCACTCTATTTGCCCAGCCCCAGCCCTGGAGAGTCCTTTAGCAGGGC
AAAGTGCAACATAGGCAGACCTTAAGGGATGACTCAGTAACAGATAAGCTTTGTGTGCCTGCAGG
GCATATAAAACAGGGGCAAGGCACAGACTCATAGCAGAGCAATCACCACCAAGCCTGGAATAAC
TGCAGCCACC
(SEQ ID NO: 39)

LVR_132_A1    AGGTTAATTTTTAAAAAGCAGTCAAAAGTCCAAGTGGCCCTTGGCAGCATTTACTCTCTCTGTTTG
CTCTGGTTAATAATCTCAGGAGCACAAACATTCCTGTACCAGAATGAACATTGAACTTTGGACTAT
ACCTGAGGGGTGAGGTAAACAACAGGACTATAAATGGCCCGGGAGGCGCCCTTTGGACCTTTTG
CAATCCTGGCGCACTGAACCCTTGACCCCTGCCCTGCAGCCCCCGCAGCTTGCTGTTTGCCCACTCT
ATTTGCCCAGCCCCAGCCCTGGAGAGTCCTTTAGCAGGGCAAAGTGCAACATAGGCAGACCTTAA
GGGATGACTCAGTAACAGATAAGCTTTGTGTGCCTGCAGGGCATATAAAACAGGGGCAAGGCAC
AGACTCATAGCAGAGCAATCACCACCAAGCCTGGAATAACTGCAGCCACC
(SEQ ID NO: 40)

LVR_132_V1    AAGCAAATATTTGTGGTTATGGATTAACTCGAACTGTTTGCCCACTCTATTTGCCCTGTACCAGAAT
GAACATTGAACTTTGGACTATACCTGAGGGGTGAGGTAAACAACAGGACTATAAATGGCCCGGG
AGGCGCCCTTTGGACCTTTTGCAATCCTGGCGCACTGAACCCTTGACCCCTGCCCTGCAGCCCCCG
CAGCTGCTGTTTGCCCACTCTATTTGCCCAGCCCCAGCCCTGGAGAGTCCTTTAGCAGGGCAAAG
TGCAACATAGGCAGACCTTAAGGGATGACTCAGTAACAGATAAGCTTTGTGTGCCTGCAGGGCAT
ATAAAACAGGGGCAAGGCACAGACTCATAGCAGAGCAATCACCACCAAGCCTGGAATAACTGCA
GCCACC
(SEQ ID NO: 41)

LVR_132_V2    GGCGCCCTTTGGACCTTTTGCAATCCTGGAGCAAACAGCAAACACTGTACCAGAATGAACATTGA
ACTTTGGACTATACCTGAGGGGTGAGGTAAACAACAGGACTATAAATGGCCCGGGAGGCGCCCT
TTGGACCTITTGCAATCCTGGCGCACTGAACCMGACCCCTGCCCTGCAGCCCCCGCAGCTGCT
GTTTGCCCACTCTATTTGCCCAGCCCCAGCCCTGGAGAGTCCTTTAGCAGGGCAAAGTGCAACATA
GGCAGACCTTAAGGGATGACTCAGTAACAGATAAGCTTTGTGTGCCTGCAGGGCATATAAAACAG
GGGCAAGGCACAGACTCATAGCAGAGCAATCACCACCAAGCCTGGAATAACTGCAGCCACC
(SEQ ID NO: 42)

LVR_133    AGAATGAACATTGAACTTTGGACTATACCTGAGGGGTGAGGTAAACAACAGGACTATAAATGGCC
CGGGAGGCGCCCTTTGGACCTTTTGCAATCCTGGCGCTCTTTTGTTTTACATGAAGGGTCTGGCAG
CCAAAGCAATCACTCAAAGTTCAAACCTTATCATTTTTTGCTTTGTTCCTCTTGGCCTTGGTTTTGTA
CATCAGCTTTGAAAATACCATCCCAGGGTTAATGCTGGGGTTAATTTATAACTAAGAGTGCTCTAG
TTTTGCAATACAGGACATGCTATAAAAATGGAAAGATGTTGCTTTCTGAGAGATGCGCCACC
(SEQ ID NO: 43)

LVR_133_A1    AGGTTAATTTTTAAAAAGCAGTCAAAAGTCCAAGTGGCCCTTGGCAGCATTTACTCTCTCTGTTTG
CTCTGGTTAATAATCTCAGGAGCACAAACATTCCTGTACCAGAATGAACATTGAACTTTGGACTAT
ACCTGAGGGGTGAGGTAAACAACAGGACTATAAATGGCCCGGGAGGCGCCCTTTGGACCTTTTG
CAATCCTGGCGCTCTTTTGTTTTACATGAAGGGTCTGGCAGCCAAAGCAATCACTCAAAGTTCAAA
CCTTATCATTTTTTGCTTTGTTCCTCTTGGCCTTGGTTTTGTACATCAGCTTTGAAAATACCATCCCA
GGGTTAATGCTGGGGTTAATTTATAACTAAGAGTGCTCTAGTTTTGCAATACAGGACATGCTATAA
AAATGGAAAGATGTTGCTTTCTGAGAGATGCGCCACC
(SEQ ID NO: 44)

TABLE 14-continued

Synthetic Promoters:

| Name | Sequence |
| --- | --- |
| LVR_133_V1 | AAGCAAATATTTGTGGTTATGGATTAACTCGAACTGTTTGCCCACTCTATTTGCCCTGTACCAGAAT<br>GAACATTGAACTTTGGACTATACCTGAGGGGTGAGGTAAACAACAGGACTATAAATGGCCCGGG<br>AGGCGCCCTTTGGACCTTTTGCAATCCTGGCGCTCTTTTGTTTTACATGAAGGGTCTGGCAGCCAA<br>AGCAATCACTCAAAGTTCAAACCTTATCATTTTTTGCTTTGTTCCTCTTGGCCTTGGTTTTGTACATC<br>AGCTTTGAAAATACCATCCCAGGGTTAATGCTGGGGTTAATTTATAACTAAGAGTGCTCTAGTTTT<br>GCAATACAGGACATGCTATAAAAATGGAAAGATGTTGCTTTCTGAGAGATGCGCCACC<br>(SEQ ID NO: 45) |
| LVR_133_V2 | GGCGCCCTTTGGACCTTTTGCAATCCTGGAGCAAACAGCAAACACTGTACCAGAATGAACATTGA<br>ACTTTGGACTATACCTGAGGGGTGAGGTAAACAACAGGACTATAAATGGCCCGGGAGGCGCCCT<br>TTGGACCTTTTGCAATCCTGGCGCTCTTTTGTTTTACATGAAGGGTCTGGCAGCCAAAGCAATCAC<br>TCAAAGTTCAAACCTTATCATTTTTTGCTTTGTTCCTCTTGGCCTTGGTTTTGTACATCAGCTTTGAA<br>AATACCATCCCAGGGTTAATGCTGGGGTTAATTTATAACTAAGAGTGCTCTAGTTTTGCAATACAG<br>GACATGCTATAAAAATGGAAAGATGTTGCTTTCTGAGAGATGCGCCACC<br>(SEQ ID NO: 46) |

TABLE 15

Prior art promoters:

| | |
| --- | --- |
| LP1 | CCCTAAAATGGGCAAACATTGCAAGCAGCAAACAGCAAACACACAGCCCTCCCTGCCTGCTGACC<br>TTGGAGCTGGGGCAGAGGTCAGAGACCTCTCTGGGCCCATGCCACCTCCAACATCCACTCGACCC<br>CTTGGAATTTCGGTGGAGAGGAGCAGAGGTTGTCCTGGCGTGGTTTAGGTAGTGTGAGAGGGGA<br>ATGACTCCTTTCGGTAAGTGCAGTGGAAGCTGTACACTGCCCAGGCAAAGCGTCCGGGCAGCGTA<br>GGCGGGCGACTCAGATCCCAGCCAGTGGACTTAGCCCCTGTTTGCTCCTCCGATAACTGGGGTGA<br>CCTTGGTTAATATTCACCAGCAGCCTCCCCCGTTGCCCCTCTGGATCCACTGCTTAAATACGGACGA<br>GGACAGGGCCCTGTCTCCTCAGCTTCAGGCACCACCACTGACCTGGGACAGTGAATCCGGACTCT<br>AAGGTAAATATAAAATTTTTAAGTGTATAATGTGTTAAACTACTGATTCTAATTGTTTCTCTCTTTTA<br>GATTCCAACCTTTGGAACTGAATTCTAGACCACC<br>(SEQ ID NO: 47) |
| CMV-IE | ATAGTAATCAATTACGGGGTCATTAGTTCATAGCCCATATATGGAGTTCCGCGTTACATAACTTAC<br>GGTAAATGGCCCGCCTGGCTGACCGCCCAACGACCCCCGCCCATTGACGTCAATAATGACGTATG<br>TTCCCATAGTAACGCCAATAGGGACTTTCCATTGACGTCAATGGGTGGAGTATTTACGGTAAACTG<br>CCCACTTGGCAGTACATCAAGTGTATCATATGCCAAGTACGCCCCCTATTGACGTCAATGACGGTA<br>AATGGCCCGCCTGGCATTATGCCCAGTACATGACCTTATGGGACTTTCCTACTTGGCAGTACATCT<br>ACGTATTAGTCATCGCTATTACCATGGTGATGCGGTTTTGGCAGTACATCAATGGGCGTGGATAG<br>CGGTTTGACTCACGGGGATTTCCAAGTCTCCACCCCATTGACGTCAATGGGAGTTTGTTTTGGCAC<br>CAAAATCAACGGGACTTTCCAAAATGTCGTAACAACTCCGCCCCATTGACGCAAATGGGCGGTAG<br>GCGTGTACGGTGGGAGGTCTATATAAGCAGAGCTGGTTTAGTGAACCGTCAGATC<br>(SEQ ID NO: 48) |
| CBA | AGATCTGAATTCGGTACCTAGTTATTAATAGTAATCAATTACGGGGTCATTAGTTCATAGCCCATA<br>TATGGAGTTCCGCGTTACATAACTTACGGTAAATGGCCCGCCTGGCTGACCGCCCAACGACCCCC<br>GCCCATTGACGTCAATAATGACGTATGTTCCCATAGTAACGCCAATAGGGACTTTCCATTGACGTC<br>AATGGGTGGAGTATTTACGGTAAACTGCCCACTTGGCAGTACATCAAGTGTATCATATGCCAAGT<br>ACGCCCCCTATTGACGTCAATGACGGTAAATGGCCCGCCTGGCATTATGCCCAGTACATGACCTTA<br>TGGGACTTTCCTACTTGGCAGTACATCTACGTATTAGTCATCGCTATTACCATGGTCGAGGTGAGC<br>CCCACGTTCTGCTTCACTCTCCCCATCTCCCCCCCCTCCCCACCCCCAATTTTGTATTTATTTATTTTTT<br>AATTATTTTGTGCAGCGATGGGGGCGGGGGGGGGGGGGGGGCGCGCGCCAGGCGGGGCGGGG<br>CGGGGCGAGGGGCGGGGCGGGGCGAGGCGGAGAGGTGCGGCGGCAGCCAATCAGAGCGGCG<br>CGCTCCGAAAGTTTCCTTTTATGGCGAGGCGGCGGCGGCGGCGGCCCTATAAAAAGCGAAGCGC<br>GCGGCGGGCGGGAGTCGCTGCGCGCTGCCTTCGCCCCGTGCCCCGCTCCGCCGCCGCCTCGCGCC<br>GCCCGCCCCGGCTCTGACTGACCGCGTTACTCCCACAGGTGAGCGGGCGGGACGGCCCTTCTCCT<br>CCGGGCTGTAATTAGCGCTTGGTTTAATGACGGCTTGTTTCTTTTCTGTGGCTGCGTGAAAGCCTT<br>GAGGGGCTCCGGGAGGGCCCTTTGTGCGGGGGGAGCGGCTCGGGGGGTGCGTGCGTGTGTGTG<br>TGCGTGGGGAGCGCCGCGTGCGGCTCCGCGCTGCCCGGCGGCTGTGAGCGCTGCGGGCGCGGC<br>GCGGGGCTTTGTGCGCTCCGCAGTGTGCGCGAGGGGAGCGCGGCCGGGGGCGGTGCCCCGCGG<br>TGCGGGGGGGGCTGCGAGGGGAACAAAGGCTGCGTGCGGGGTGTGTGCGTGGGGGGGTGAGC<br>AGGGGGTGTGGGCGCGTCGGTCGGGCTGCAACCCCCCCTGCACCCCCCTCCCCGAGTTGCTGAGC<br>ACGGCCCGGCTTCGGGTGCGGGGCTCCGTACGGGGCGTGGCGCGGGGCTCGCCGTGCCGGGCG<br>GGGGGTGGCGGCAGGTGGGGGTGCCGGGCGGGGCGGGGCCGCCTCGGGCCGGGGAGGGCTC<br>GGGGGAGGGGCGCGGCGGCCCCCGGAGCGCCGGCGGCTGTCGAGGCGCGGCGAGCCGCAGCC<br>ATTGCCTTTTATGGTAATCGTGCGAGAGGGCGCAGGGACTTCCTTTGTCCCAAATCTGTGCGGAG<br>CCGAAATCTGGGAGGCGCCGCCGCACCCCCTCTAGCGGGCGCGGGGCGAAGCGGTGCGGCGCC<br>GGCAGGAAGGAAATGGGCGGGGAGGGCCTTCGTGCGTCGCCGCGCCGCCGTCCCCTTCTCCCTC<br>TCCAGCCTCGGGGCTGTCCGCGGGGGGACGGCTGCCTTCGGGGGGGACGGGGCAGGGCGGGGT<br>TCGGCTTCTGGCGTGTGACCGGCGGCTCTAGAGCCTCTGCTAACCATGTTCATGCCTTCTTCTTTTT<br>CCTACAGCTCCTGGGCAACGTGCTGGTTATTGTGCTGTCTCATCATTTTGGCAAAGAATTCCTCGA<br>AGATCTAGGCAACGCGTCTCGAGGCGGCCGCCGCCACC<br>(SEQ ID NO: 72) |

TABLE 15-continued

Prior art promoters:

```
TBG     AGGTTAATTTTTAAAAAGCAGTCAAAAGTCCAAGTGGCCCTTGGCAGCATTTACTCTCTCTGTTTG
        CTCTGGTTAATAATCTCAGGAGCACAAACATTCCAGATCCAGGTTAATTTTTAAAAAGCAGTCAAA
        AGTCCAAGTGGCCCTTGGCAGCATTTACTCTCTCTGTTTGCTCTGGTTAATAATCTCAGGAGCACA
        AACATTCCAGATCCGGCGCGCCAGGGCTGGAAGCTACCTTTGACATCATTTCCTCTGCGAATGCAT
        GTATAATTTCTACAGAACCTATTAGAAAGGATCACCCAGCCTCTGCTTTTGTACAACTTTCCCTTAA
        AAAACTGCCAATTCCACTGCTGTTTGGCCCAATAGTGAGAACTTTTTCCTGCTGCCTCTTGGIGCTT
        TTGCCTATGGCCCCTATTCTGCCTGCTGAAGACACTCTTGCCAGCATGGACTTAAACCCCTCCAGCT
        CTGACAATCCTCTTTCTCTTTTGTTTTACATGAAGGGTCTGGCAGCCAAAGCAATCACTCAAAGTTC
        AAACCTTATCATTTTTTGCTTTGTTCCTCTTGGCCTTGGTTTTGTACATCAGCTTTGAAAATACCATC
        CCAGGGTTAATGCTGGGGTTAATTTATAACTAAGAGTGCTCTAGTTTTGCAATACAGGACATGCTA
        TAAAAATGGAAAGATGTTGCTTTCTGAGAGACTGCAGAAGTTGGTCGTGAGGCACTGGGCAGGT
        AAGTATCAAGGTTACAAGACAGGTTTAAGGAGACCAATAGAAACTGGGCTTGTCGAGACAGAGA
        AGACTCTTGCGTTTCTGATAGGCACCTATTGGTCTTACTGACATCCACTTTGCCTTTCTCTCCACAG
        GGCAATCCGGTACTGTTGGTAAAGCCACC
        (SEQ ID NO: 83)
```

Example 2

Materials and Methods

Promoters were designed using Synpromics' proprietary platform PROMPT® and synthesised by GeneArt®. This involved an analysis of liver gene expression datasets to identify candidate genes, including microarray and NGS datasets and scientific literature reviews to identify genes expressed to very high levels in liver cells. Cis-regulatory element selection and analysis was performed. TFBS within the CREs were identified.

Synthetic promoters comprising the CRMs linked to minimal/proximal promoters as discussed herein, were cloned upstream of the luciferase reporter gene followed by SV40 late PolyA signal into a vector with a backbone having properties to pUC19. DNA preparations were transfected into either Huh7 (a hepato-cellular carcinoma cell line), HeLa (an immortal cell line derived from cervical cancer) or HEK293 (human embryonic kidney cells) to asses transcriptional activity. Huh-7 cells were sourced from JCRB Cell Bank (JCRB0403), HeLa and HEK293 were sourced from ECACC cell bank. All cell lines were grown and maintained according to the cell banks' recommendations.

Transfections were performed in 48 well plates in triplicate using FuGene HD Transfection Reagent (Promega #E2311) ata DNA:FuGene HD ratio of 1:1.1. Luciferase activity was measured 24 hours after transfection. Cells were washed with phosphate buffered saline (PBS), lysed in 100 μl Passive Lysis Buffer (Promega #E194A) and stored at −80° C. overnight. Luciferase activity was quantified using the Luciferase Reporter 1000 assay system (Promega #E4550) following manufacturer's guidelines in 10 μl of lysate using 96 well flat bottom solid white Microplate FluoroNunc plates (ThermoFisher #236105) and luminescence quantified in a FLUOstar Omega plate reader (BMG Labtech) machine.

The above luciferase methods are conventional in the art, and similar techniques have been described extensively in the literature, e.g. in Alam and Cook, "*Reporter Genes: Application to the Study of Mammalian Gene Transcription*", ANALYTICAL BIOCHEMISTRY 188, 245-254 (1990).

Discussion and Results

Bioinformatic analysis of large genomic data sets led to the discovery of cis-regulatory elements (CRE) expected to be useful to enhance liver-specific gene expression. The top 12 CREs were selected for the design of four synthetic liver-specific promoters. These promoters were named LVR_127, LVR_131, LVR_132 and LVR_133 respectively. The structure of these promoters is shown in FIG. 1, including the CRE and minimal/proximal promoter elements that are present in each promoter.

The sequences of these promoters are shown in Table 14, and the CRMs comprised in these promoters are shown in Table 13. The sequences of the component parts (CREs) of these CRMs/promoters are set out in Table 1, and the minimal/proximal promoters that are operably linked to three CRMs are set out in Table 2. For the promoters LVR_127, LVR_131, LVR_132 the CRMs comprising the various combinations of CREs (Table 13) were positioned upstream of the minimal promoter LVR_CRE0052_G6PC (see Table 2). For LVR_133 the CRM was placed upstream of the SERPINA7 proximal promoter (LVR_CRE0079_SERPINA7, see Table 2).

Figure 2:
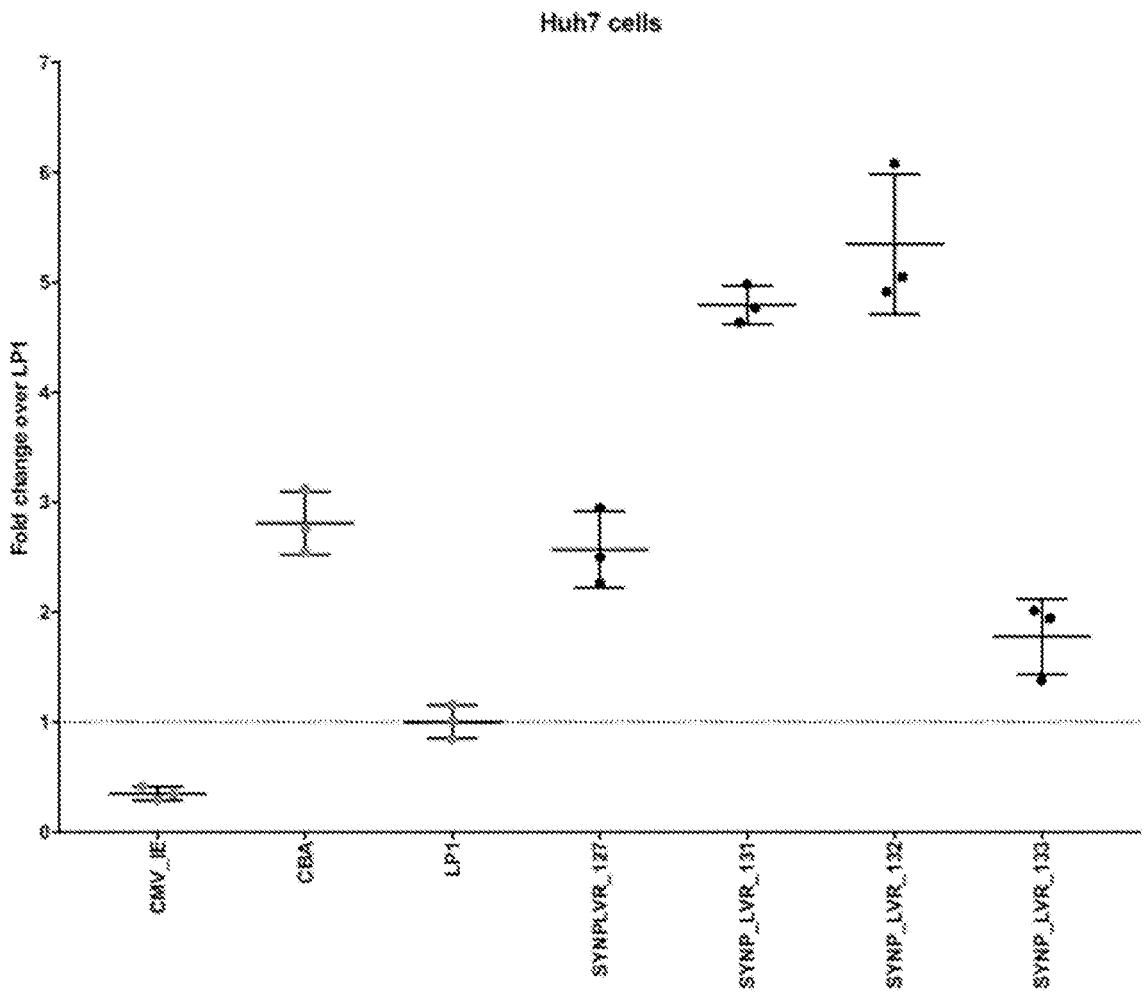
FIG. 2 shows a graph of expression levels of a luciferase reporter protein driven by various synthetic liver-specific promoters in the liver-derived cell line Huh7 relative to expression levels driven by the known liver-specific promoter LP1 and the ubiquitous CMV-IE and CBA promoters. The CBA (chicken beta actin) promoter as used herein comprises the CMV immediate early enhancer+chicken beta actin proximal promoter+intron).
Figure 4A:
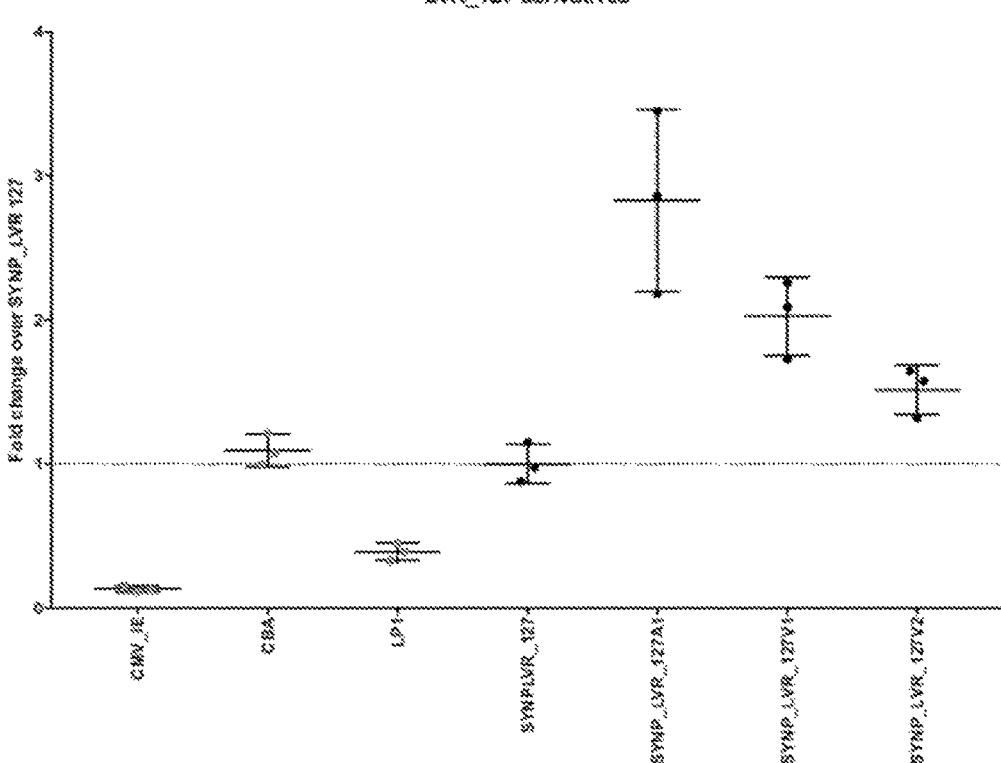
FIG. 4*a* shows a graph of expression levels of luciferase reporter protein driven by variants of the LVR_127 synthetic liver-specific promoter in Huh7 cells, i.e. LVR_127 alone, and with the A1, V1 and V2 CRE enhancer elements added immediately upstream of the LVR_127 promoter. Again, a comparison with the LP1, CMV-IE and CBA promoters is shown.
Figure 4B:
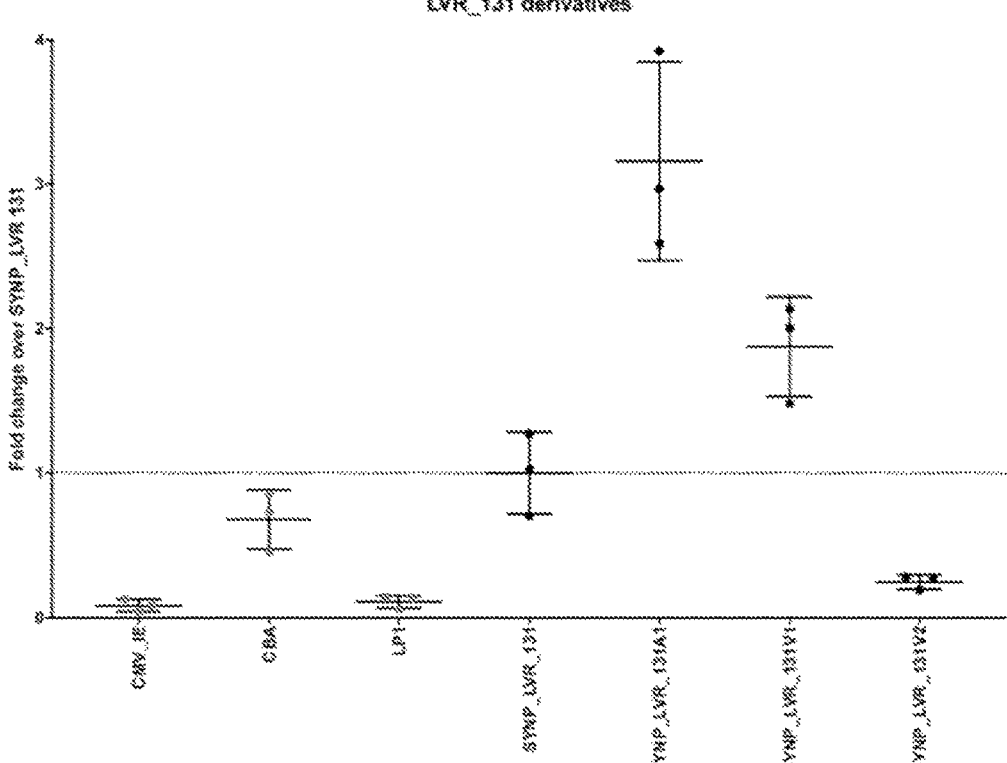
FIG. 4*b* shows a graph of expression levels of luciferase reporter protein driven by variants of the LVR_131 synthetic liver-specific promoter in Huh7 cells, i.e. LVR_131 alone, and with the A1, V1 and V2 CRE enhancer elements added immediately upstream of the LVR_131 promoter. Again, a comparison with the LP1, CMV-IE and CBA promoters is shown.
Figure 4C:
FIG. 4*c* shows a graph of expression levels of luciferase reporter protein driven by variants of the LVR_132 synthetic liver-specific promoter in Huh7 cells, i.e. LVR_132 alone, and with the A1, V1 and V2 CRE enhancer elements added immediately upstream of the LVR_132 promoter. Again, a comparison with the LP1, CMV-IE and CBA promoters is shown.
Figure 4C:
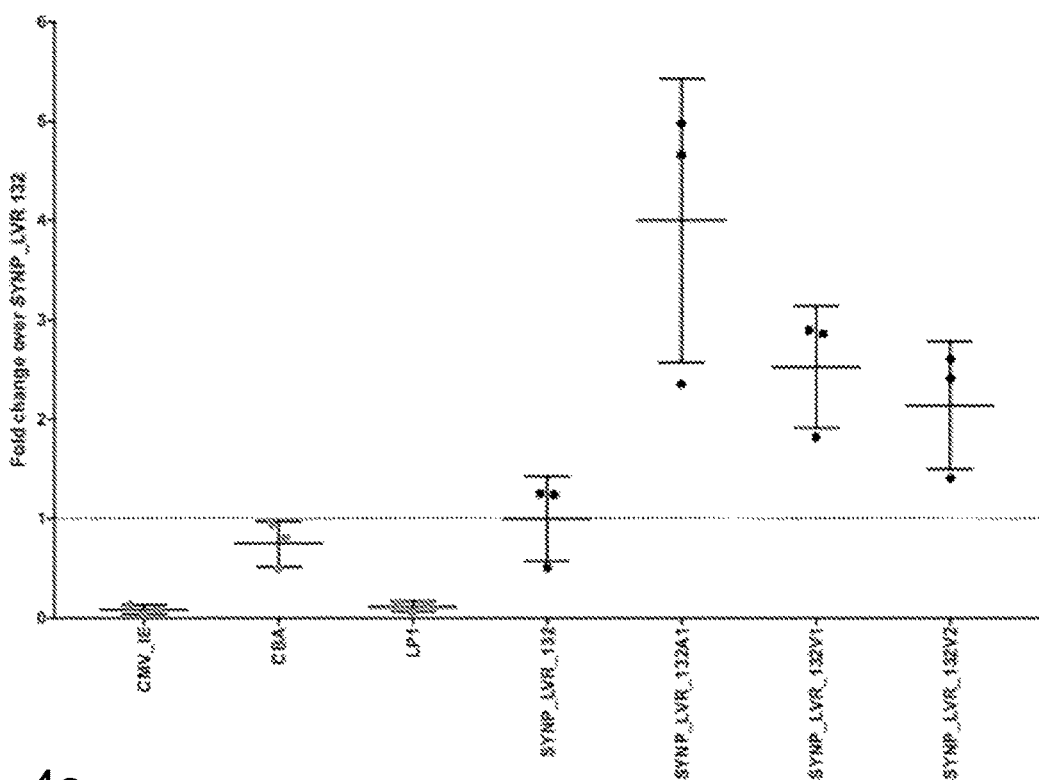
Figure 4D:
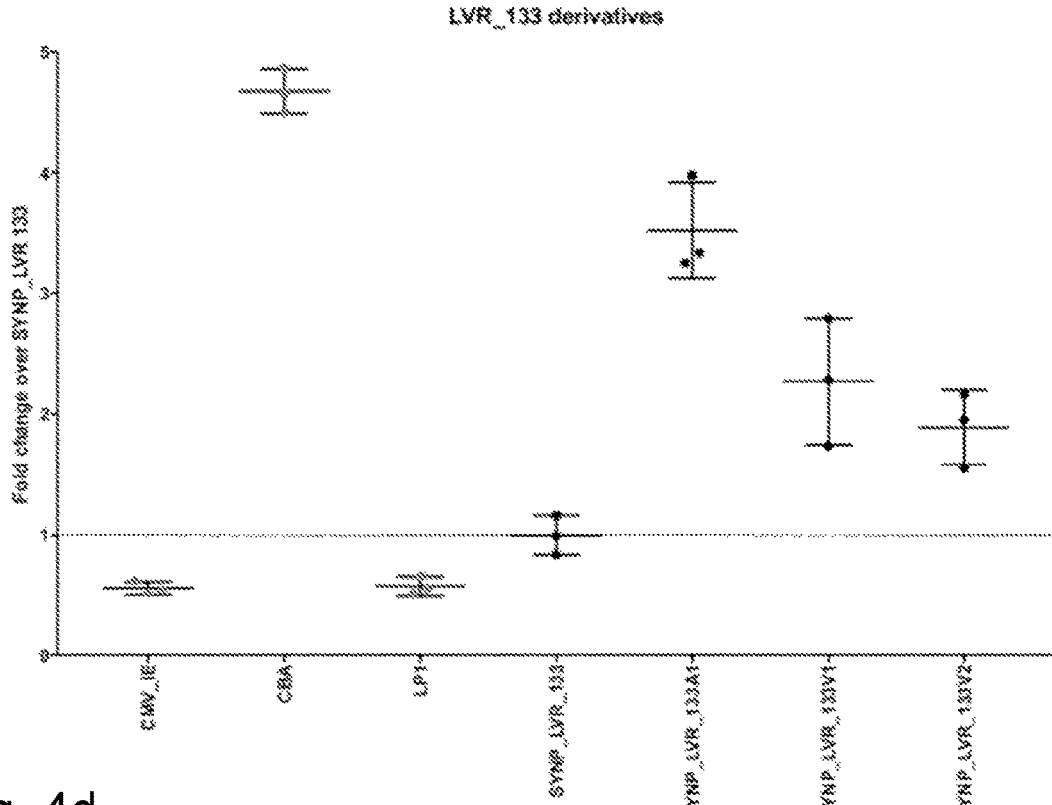
FIG. 4*d* shows a graph of expression levels of luciferase reporter protein driven by variants of the LVR_133 synthetic liver-specific promoter in Huh7 cells, i.e. LVR_133 alone, and with the A1, V1 and V2 CRE enhancer elements added immediately upstream of the LVR_133 promoter. Again, a comparison with the LP1, CMV-IE and CBA promoters is shown.

The ability of these synthetic promoters to drive expression in liver cells was benchmarked against the ubiquitous CMV_IE and CBA promoters, and also against the known liver specific promoter LP1. The sequences of these promoters are provided in Table 14. The results of this experiment are shown in FIG. 2, which shows a mean of 3 replicates. The bars show standard deviation.

All of the synthetic promoters according to the invention showed higher activity than the LP1 promoter in Huh7 cells (FIG. 2). When these promoters were counter-screened in non-liver-derived HEK293 and HeLa cells, they showed negligible activity compared to the ubiquitously active promoters CMV_IE and CBA (see FIG. 5 and FIG. 6). This indicates that the LVR_127, LVR_131, LVR_132 and LVR_133 promoters are highly-specific for activity in liver cell lines.

Figure 3:
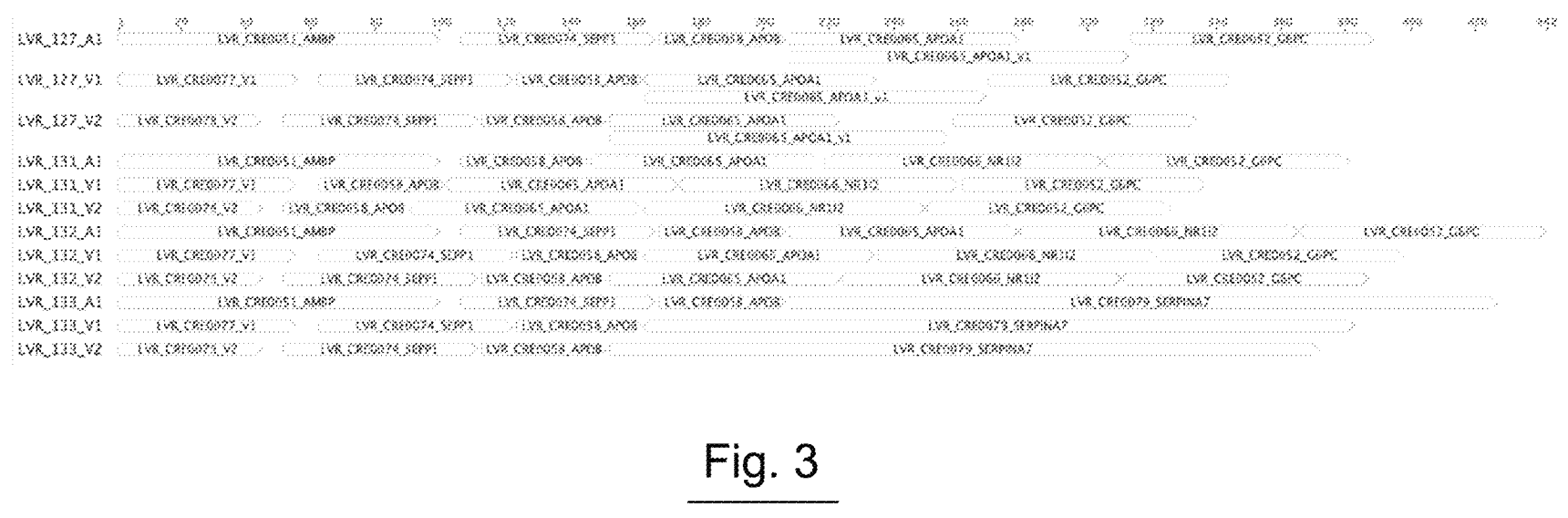

Subsequently, two candidate enhancers were designed based on bioinformatic predictions using the following CREs LVR_CRE0080_PROC, LVR_CRE0081_APOA1, LVR_CRE0061_APOB and LVR_CRE0082_APOC4. These synthetic enhancers were designated as "V1" (or LVR_CRE0077_V1) and "V2" (or LVR_CRE0078_V2), respectively (FIG. 3). The effects of these candidate enhancers were tested by adding them to the previously described LVR_127, LVR_131, LVR_132 and LVR_133 liver-specific promoters. The known human alpha(1)-microglobulin/bi-kunin precursor (AMBP) enhancer, designated herein as "A1" (or LVR_CRE0051_AMBP, SEQ ID NO: 1) (Rouet et al., 1992) was also adding them to the LVR_127, LVR_131, LVR_132 and LVR_133 liver-specific promoters. These new promoters with the additional enhancer element were tested in Huh7 cells, as previously described for the LVR_127, LVR_131, LVR_132 and LVR_133 liver-specific promoters.

Figure 5:
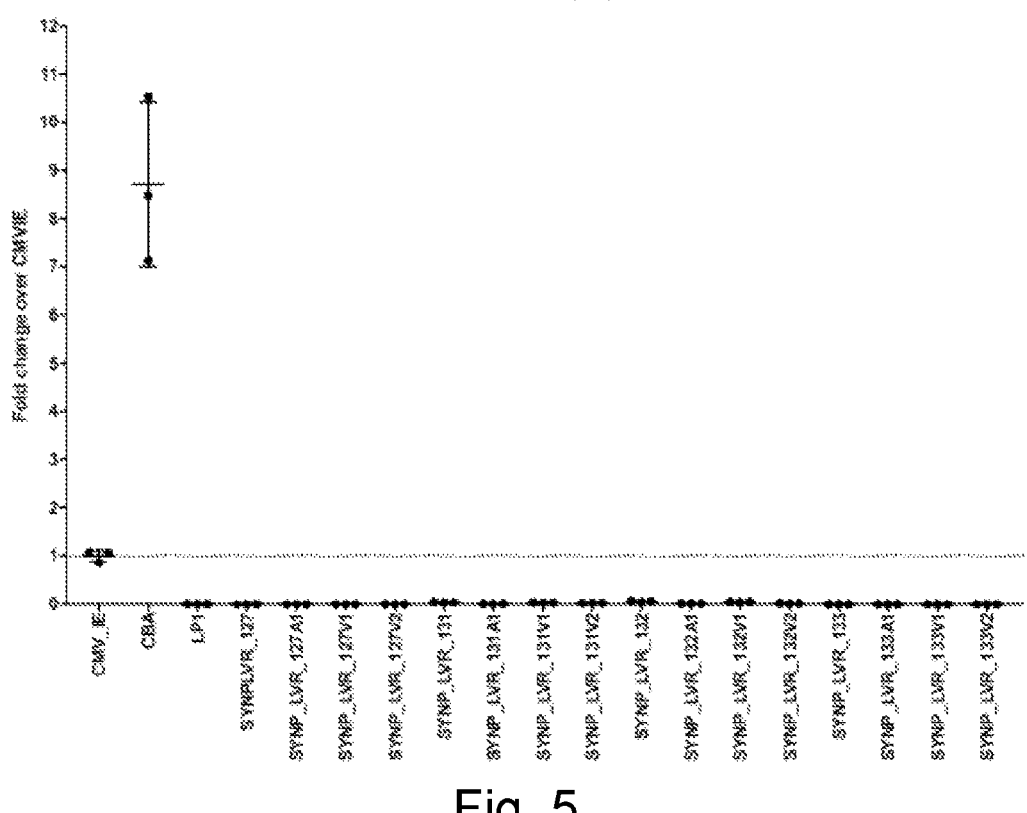
FIG. 5 shows a graph of expression levels of luciferase reporter protein in HEK-293 cells (i.e. non-liver-derived cells) driven by the LVR_127, LVR_131, LVR_132 and LVR_133 synthetic liver-specific promoters, and the variants thereof as set out in respect of FIGS. 4*a*-4*d*. Again, a comparison with the LP1, CMV-IE and CBA promoters is shown.
Figure 6:
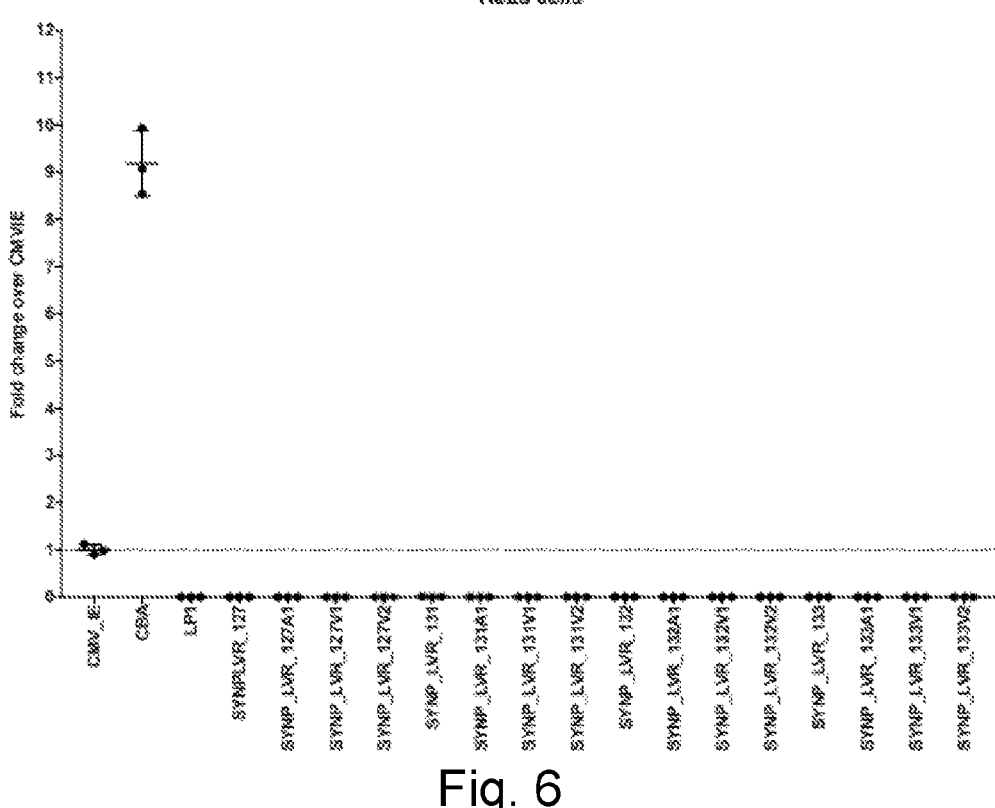
FIG. 6 shows a graph of expression levels of luciferase reporter protein in HeLa cells (i.e. non-liver-derived cells) driven by the LVR_127, LVR_131, LVR_132 and LVR_133 synthetic liver-specific promoters, and the variants thereof as set out in respect of FIGS. 4*a*-4*d*. Again, a comparison with the LP1, CMV-IE and CBA promoters is shown.

As shown in FIGS. 4a to 4d, addition of any one of V1 or V2 enhancer significantly enhanced promoter activity of LVR_127, LVR_132 and LVR_133. The only exception observed was combining LVR_131 with V2. Moreover, addition of V1 and V2 enhancer sequences retained promoter liver-specificity, which was confirmed when the promoters were counter-screened in HEK293 and HeLa cells (FIG. 5).

The SYNP_LVR_131 family of promoters (SEQ ID NO: 35 to SEQ ID NO: 38), and in particular SYNP_LVR_131_A1 (SEQ ID NO: 36), appears to be especially powerful. Thus, these promoters, and the CRMs that they comprise (SEQ ID NO: 19 to SEQ ID NO: 22, and especially SEQ ID NO: 20), and functional variants thereof, are of particular interest. However, all of the synthetic promoters according to the present invention appear to be both powerful and liver-specific.

It is expected that the CREs used in the specifically exemplified CRMs and promoters can be rearranged (for example, shuffled or inverted) and liver-specific promoter activity will be remained. Furthermore, it is expected that the sequence of the CREs, CRMs and promoters can be altered considerably while retaining liver-specific promoter activity. Generally, the TFBS within CREs should be preserved to the extent that the CRE is still able bind the same TFs, and preferably in the same order and approximate spacing as the reference CRE, in order to maintain function. Generally, the disclosed CREs (i.e. enhancers) themselves are self-contained regulatory units, and they can be moved, and/or orientation altered, without loss of function. The skilled person can readily determine the effects of any alteration to a CRE, CRM or promoter (e.g. in absolute terms or in comparison to a reference CRE, CRM or promoter) using the methodologies described herein. Furthermore, the CREs can be incorporated in other promoters in order to drive liver-specific expression (especially V1 and V2, which are believed to have particularly broad utility, but also the other CREs disclosed herein).

In summary, these new synthetic promoters and enhancers are valuable tools for gene therapy through lever specific gene expression and for the design of liver-specific gene therapies.

Example 3

Figure 7:
FIG. 7 shows the relative activity of the LVR_127, LVR_127 A1, LVR_127V1, LVR_127V2, LVR_131, LVR_131 A1, LVR_131V1, LVR_131V2, LVR_132, LVR_132 A1, LVR_132V1, LVR_132V2, LVR_133, LVR_133 A1, LVR_133V1 and LVR_133V2 compared with the promoter TBG.

The synthetic liver specific promoters as used in Example 2 were further analysed in comparison to the liver-specific promoter TBG (SEQ ID NO: 76). TBG was found to have stronger and more consistent in vitro expression than LP1. The methodology was essentially identical to Example 2, and the results are shown in FIG. 7. 'Relative activity' in this graph showing the activity of the liver-specific promoters tested in Huh7 cells is the activity of the named promoter expressed as a percentage of the activity of TBG (i.e. wherein 100 is the same activity as TBG, more than 100 is higher activity compared to TBG, and less than 100 is lower activity compared to TBG). It should be noted that TBG is an extremely powerful liver-specific promoter, and thus a promoter which shows expression which is less than TBG may still be extremely useful. In particular, promoters which are shorter than TBG, but which still demonstrate high levels of activity (e.g. 15%, more preferably 25%, 50%, or 75% of the activity of TBG or higher) are of particular interest. It can be seen again that the synthetic liver-specific promoters of the present invention are all highly active in liver cells.

It can be seen that these synthetic liver-specific promoters are all highly active in liver cells.

While the present inventions have been described and illustrated in conjunction with a number of specific embodiments, those skilled in the art will appreciate that variations and modifications may be made without departing from the principles of the inventions as herein illustrated, as described and claimed. The present inventions may be embodied in other specific forms without departing from their spirit or essential characteristics. The described embodiments are considered in all respects to be illustrative and not restrictive.

The invention claimed is:

1. A synthetic liver-specific cis-regulatory enhancer element comprising a sequence according to SEQ ID NO: 2 or SEQ ID NO: 65, wherein each n of SEQ ID NO: 65 represent an spacer sequence.

2. The synthetic liver-specific cis-regulatory enhancer element according to claim 1 which is 100 nucleotides or less.

3. A synthetic liver-specific cis-regulatory module (CRM) comprising the cis-regulatory enhancer element according to claim 1.

4. The synthetic liver-specific CRM according to claim 3 further comprising at least one, liver-specific cis-regulatory enhancer elements selected from the group consisting of: SEQ ID NO: 1; SEQ ID NO: 3; SEQ ID NO: 4; SEQ ID NO: 5; SEQ ID NO: 6; SEQ ID NO: 7; SEQ ID NO: 8; SEQ ID NO: 67, wherein each n of SEQ ID NO: 67 represent spacer sequences; SEQ ID NO: 68, wherein n of SEQ ID NO: 68 represents an spacer sequence; SEQ ID NO: 69; SEQ ID NO: 70, wherein each n of SEQ ID NO: 70 represent spacer sequences; SEQ ID NO: 71, wherein each n of SEQ ID NO: 71 represent spacer sequences; and SEQ ID NO: 73, wherein n of SEQ ID NO: 73 represents an spacer sequence.

5. The synthetic liver-specific CRM according to claim 4 comprising a combination of cis-regulatory elements, selected from the group consisting of:

(V1)-S-(LVR_CRE0074_SEPP1)-S-(LVR_CRE0058_
   APOB)-S-(LVR_CRE0065_APOA1);
(V1)-S-(LVR_CRE0058_APOB)-S-
   (LVR_CRE0065_APOA1)-S-(LVR_CRE0066_
   NR1I2);
(V1)-S-(LVR_CRE0074_SEPP1)-S-
   (LVR_CRE0058_APOB)-S-(LVR_CRE0066_NR1I2);
   and (V1)-S-(LVR_CRE0074_SEPP1)-S-(LVR_CRE0058_
   APOB),
      wherein S represents an spacer sequence positioned
      between adjacent cis-regulatory elements.

6. The synthetic liver-specific CRM according to claim 4, comprising any one of SEQ ID NO: 17, SEQ ID NO: 21, SEQ ID NO: 25 or SEQ ID NO: 29.

7. A synthetic liver-specific promoter comprising the synthetic liver-specific cis-regulatory element according to claim 1.

8. The synthetic liver-specific promoter according to claim 7 comprising the cis-regulatory element and/or the cis-regulatory module operably linked to a minimal promoter or proximal promoter, wherein the minimal promoter comprises or consists of the LVR_CRE0052_G6PC minimal promoter, which has the sequence: GGG-CATATAAAACAGGGGCAAGGCACAGACTCAT-AGCAGAGCAATCACCACCAAGC CTGGAATA-ACTGCAGCCACC (SEQ ID NO: 9); or wherein the proximal promoter comprises a liver-specific proximal promoter that comprises of consists of the SERPINA7 proximal promoter, which has the sequence: CTCTTTTGTTTTA-CATGAAGGGTCTGGCAGCCAAAGCAATCACT-CAAAGTTCAAACC TTATCATTTTTTGCTTTGTT-CCTCTTGGCCTTGGTTTTGTACATCAGCTTTGAA-AATAC CATCCCAGGGTTAATGCTGGGGTTAATT-TATAACTAAGAGTGCTCTAGTTTTGCAAT ACAGGA-CATGCTATAAAAATGGAAAGATGTTGCTTTCT-GAGAGATGCGCCACC (SEQ ID NO: 10).

9. The synthetic liver-specific promoter according to claim 7 which comprises or consists of a sequence according to any one of SEQ ID NO: 33, SEQ ID NO: 37, SEQ ID NO: 41, SEQ ID NO: 45.

10. The synthetic liver-specific promoter according to claim 7 which is able to increase expression of gene in the liver of a subject or in a liver cell by at least 40% relative to the LP-1 promoter.

11. A synthetic liver-specific expression cassette comprising the synthetic liver-specific promoter according to claim 7 operatively linked to a gene, wherein the gene encodes a therapeutic expression product, a therapeutic polypeptide suitable for use in treating a disease or condition associated with the liver.

12. A vector comprising the synthetic liver-specific cis-regulatory element according to claim 1, wherein the vector is a gene therapy vector, suitably an AAV vector, an adeno-viral vector, a retroviral vector or a lentiviral vector.

13. A pharmaceutical composition comprising the synthetic liver-specific expression cassette according to claim 11.

14. A cell comprising the synthetic liver-specific cis-regulatory enhancer element according to claim 1, wherein the cell is a eukaryotic cell.

15. A method for producing an expression product, the method comprising providing introducing the synthetic liver-specific expression cassette according to claim 11 into a liver cell and expressing the gene present in the synthetic liver-specific expression cassette.

16. A method of expressing a therapeutic transgene in a liver cell, the method comprising introducing into the liver cell the synthetic liver-specific expression cassette according to claim 11.

17. The method of claim 16 comprising administering the synthetic liver-specific expression cassette in a vector and the vector, according to claim 12 to a subject, wherein the vector is an AAV vector.

* * * * *

SEQUENCE LISTING

```
<160> NUMBER OF SEQ ID NOS: 83

<210> SEQ ID NO 1
<211> LENGTH: 100
<212> TYPE: DNA
<213> ORGANISM: Artificial Sequence
<220> FEATURE:
<223> OTHER INFORMATION: A1 (alpha mic/bik or LVR_CRE0051_AMBP)

<400> SEQUENCE: 1
aggttaattt ttaaaaagca gtcaaaagtc caagtggccc ttggcagcat ttactctctc         60
tgtttgctct ggttaataat ctcaggagca caaacattcc                              100

<210> SEQ ID NO 2
<211> LENGTH: 56
<212> TYPE: DNA
<213> ORGANISM: Artificial Sequence
<220> FEATURE:
<223> OTHER INFORMATION: V1 (LVR_CRE0077_V1)

<400> SEQUENCE: 2
aagcaaatat ttgtggttat ggattaactc gaactgtttg cccactctat ttgccc           56

<210> SEQ ID NO 3
```

-continued

<211> LENGTH: 45
<212> TYPE: DNA
<213> ORGANISM: Artificial Sequence
<220> FEATURE:
<223> OTHER INFORMATION: V2 (LVR_CRE0078_V2)

<400> SEQUENCE: 3
ggcgcccttt ggaccttttg caatcctgga gcaaacagca aacac                    45

<210> SEQ ID NO 4
<211> LENGTH: 61
<212> TYPE: DNA
<213> ORGANISM: Artificial Sequence
<220> FEATURE:
<223> OTHER INFORMATION: LVR_CRE0074_SEPP1

<400> SEQUENCE: 4
agaatgaaca ttgaactttg gactatacct gaggggtgag gtaaacaaca ggactataaa    60
t                                                                    61

<210> SEQ ID NO 5
<211> LENGTH: 40
<212> TYPE: DNA
<213> ORGANISM: Artificial Sequence
<220> FEATURE:
<223> OTHER INFORMATION: LVR_CRE0058_APOB

<400> SEQUENCE: 5
ggcccgggag gcgccctttg gaccttttgc aatcctggcg                          40

<210> SEQ ID NO 6
<211> LENGTH: 72
<212> TYPE: DNA
<213> ORGANISM: Artificial Sequence
<220> FEATURE:
<223> OTHER INFORMATION: LVR_CRE0065_APOA1

<400> SEQUENCE: 6
cactgaaccc ttgacccctg ccctgcagcc cccgcagctt gctgtttgcc cactctattt    60
gcccagcccc ag                                                        72

<210> SEQ ID NO 7
<211> LENGTH: 106
<212> TYPE: DNA
<213> ORGANISM: Artificial Sequence
<220> FEATURE:
<223> OTHER INFORMATION: LVR_CRE0065_APOA1_v1

<400> SEQUENCE: 7
cactgaaccc ttgacccctg ccctgcagcc cccgcagctt gctgtttgcc cactctattt    60
gcccagcccc agggacagag ctgatccttg aactcttaag ttccac                  106

<210> SEQ ID NO 8
<211> LENGTH: 87
<212> TYPE: DNA
<213> ORGANISM: Artificial Sequence
<220> FEATURE:
<223> OTHER INFORMATION: LVR_CRE0066_NR1I2

<400> SEQUENCE: 8
ccctggagag tcctttagca gggcaaagtg caacataggc agaccttaag ggatgactca    60
gtaacagata agctttgtgt gcctgca                                        87

<210> SEQ ID NO 9
<211> LENGTH: 76
<212> TYPE: DNA
<213> ORGANISM: Artificial Sequence
<220> FEATURE:
<223> OTHER INFORMATION: LVR_CRE0052_G6PC

<400> SEQUENCE: 9
gggcatataa aacagggggca aggcacagac tcatagcaga gcaatcacca ccaagcctgg     60
aataactgca gccacc                                                     76

<210> SEQ ID NO 10
<211> LENGTH: 226
<212> TYPE: DNA
<213> ORGANISM: Artificial Sequence
<220> FEATURE:
<223> OTHER INFORMATION: SERPINA7 proximal promoter
      (LVR_CRE0079_SERPINA7)

<400> SEQUENCE: 10
ctcttttgtt ttacatgaag ggtctggcag ccaaagcaat cactcaaagt tcaaacctta     60 tcatttttg ctttgttcct cttggccttg gttttgtaca tcagctttga aaataccatc    120
ccagggttaa tgctgggggtt aatttataac taagagtgct ctagtttttgc aatacaggac    180 atgctataaa aatggaaaga tgttgctttc tgagagatgc gccacc                   226

<210> SEQ ID NO 11
<211> LENGTH: 33
<212> TYPE: DNA
<213> ORGANISM: Artificial Sequence
<220> FEATURE:
<223> OTHER INFORMATION: LVR_CRE0080_PROC

<400> SEQUENCE: 11
aagcaaatat ttgtggttat ggattaactc gaa                                  33

<210> SEQ ID NO 12
<211> LENGTH: 23
<212> TYPE: DNA
<213> ORGANISM: Artificial Sequence
<220> FEATURE:
<223> OTHER INFORMATION: LVR_CRE0081_APOA1

<400> SEQUENCE: 12
ctgtttgccc actctatttg ccc                                             23

<210> SEQ ID NO 13
<211> LENGTH: 29
<212> TYPE: DNA
<213> ORGANISM: Artificial Sequence
<220> FEATURE:
<223> OTHER INFORMATION: LVR_CRE0061_APOB

<400> SEQUENCE: 13
ggcgcccttt ggaccttttg caatcctgg                                       29

<210> SEQ ID NO 14
<211> LENGTH: 16
<212> TYPE: DNA
<213> ORGANISM: Artificial Sequence
<220> FEATURE:
<223> OTHER INFORMATION: LVR_CRE0082_APOC4

<400> SEQUENCE: 14
agcaaacagc aaacac                                                     16

```
<210> SEQ ID NO 15
<211> LENGTH: 207
<212> TYPE: DNA
<213> ORGANISM: Artificial Sequence
<220> FEATURE:
<223> OTHER INFORMATION: CRM_LVR_127

<400> SEQUENCE: 15
agaatgaaca ttgaactttg gactatacct gaggggtgag gtaaacaaca ggactataaa      60
tggcccggga ggcgccttt ggacctttg caatcctggc gcactgaacc cttgacccct      120
gccctgcagc ccccgcagct tgctgtttgc ccactctatt tgcccagccc cagggacaga      180
gctgatcctt gaactcttaa gttccac      207

<210> SEQ ID NO 16
<211> LENGTH: 313
<212> TYPE: DNA
<213> ORGANISM: Artificial Sequence
<220> FEATURE:
<223> OTHER INFORMATION: CRM_LVR_127_A1

<400> SEQUENCE: 16
aggttaattt ttaaaaagca gtcaaaagtc caagtggccc ttggcagcat ttactctctc      60
tgtttgctct ggttaataat ctcaggagca caaacattcc tgtaccagaa tgaacattga      120
actttggact atacctgagg ggtgaggtaa acaacaggac tataaatggc ccgggaggcg      180 cccttttggac cttttgcaat cctggcgcac tgaacccttg accctgccc tgcagccccc      240 gcagcttgct gtttgcccac tctatttgcc cagccccagg gacagagctg atccttgaac      300
tcttaagttc cac      313

<210> SEQ ID NO 17
<211> LENGTH: 269
<212> TYPE: DNA
<213> ORGANISM: Artificial Sequence
<220> FEATURE:
<223> OTHER INFORMATION: CRM_LVR_127_V1

<400> SEQUENCE: 17
aagcaaatat ttgtggttat ggattaactc gaactgtttg cccactctat ttgccctgta      60
ccagaatgaa cattgaactt tggactatac ctgaggggtg aggtaaacaa caggactata      120
aatggcccgg gaggcgccct ttggaccttt tgcaatcctg gcgcactgaa cccttgaccc      180
ctgccctgca gccccgcag cttgctgttt gcccactcta tttgcccagc ccagggaca      240 gagctgatcc ttgaactctt aagttccac      269

<210> SEQ ID NO 18
<211> LENGTH: 258
<212> TYPE: DNA
<213> ORGANISM: Artificial Sequence
<220> FEATURE:
<223> OTHER INFORMATION: CRM_LVR_127_V2

<400> SEQUENCE: 18 ggcgccttt ggacctttg caatcctgga gcaaacagca aacactgtac cagaatgaac      60
attgaacttt ggactatacc tgaggggtga ggtaaacaac aggactataa atggcccggg      120
aggcgccctt tggacctttt gcaatcctgg cgcactgaac ccttgacccc tgccctgcag      180
cccccgcagc ttgctgtttg cccactctat ttgcccagcc ccagggacag agctgatcct      240
```

-continued

```
tgaactctta agttccac                                                     258

<210> SEQ ID NO 19
<211> LENGTH: 199
<212> TYPE: DNA
<213> ORGANISM: Artificial Sequence
<220> FEATURE:
<223> OTHER INFORMATION: CRM_LVR_131

<400> SEQUENCE: 19
ggcccgggag gcgccctttg dacctttgc aatcctggcg cactgaaccc ttgacccctg          60
ccctgcagcc cccgcagctt gctgtttgcc cactctattt gcccagcccc agccctggag         120
agtcctttag cagggcaaag tgcaacatag gcagaccta aggatgact cagtaacaga          180 taagctttgt gtgcctgca                                                      199

<210> SEQ ID NO 20
<211> LENGTH: 305
<212> TYPE: DNA
<213> ORGANISM: Artificial Sequence
<220> FEATURE:
<223> OTHER INFORMATION: CRM_LVR_131_A1

<400> SEQUENCE: 20
aggttaattt ttaaaaagca gtcaaaagtc caagtggccc ttggcagcat ttactctctc          60
tgtttgctct ggttaataat ctcaggagca caaacattcc tgtaccggcc cgggaggcgc         120
cctttggacc ttttgcaatc ctggcgcact gaacccttga cccctgccct gcagcccccg         180
cagcttgctg tttgcccact ctatttgccc agccccagcc ctggagagtc ctttagcagg         240
gcaaagtgca acataggcag accttaaggg atgactcagt aacagataag ctttgtgtgc         300
ctgca                                                                     305

<210> SEQ ID NO 21
<211> LENGTH: 261
<212> TYPE: DNA
<213> ORGANISM: Artificial Sequence
<220> FEATURE:
<223> OTHER INFORMATION: CRM_LVR_131_V1

<400> SEQUENCE: 21
aagcaaatat ttgtggttat ggattaactc gaactgtttg cccactctat ttgccctgta          60
ccggcccggg aggcgccctt tggacctttt gcaatcctgg cgcactgaac ccttgaccccc        120 tgccctgcag cccccgcagc ttgctgtttg cccactctat ttgcccagcc ccagccctgg         180
agagtccttt agcagggcaa agtgcaacat aggcagacct taagggatga ctcagtaaca         240
gataagcttt gtgtgcctgc a                                                   261

<210> SEQ ID NO 22
<211> LENGTH: 250
<212> TYPE: DNA
<213> ORGANISM: Artificial Sequence
<220> FEATURE:
<223> OTHER INFORMATION: CRM_LVR_131_V2

<400> SEQUENCE: 22
ggcgcccttt ggaccttttg caatcctgga gcaaacagca aacactgtac cggcccggga          60
ggcgcccttt ggaccttttg caatcctggc gcactgaacc cttgacccct gccctgcagc         120 cccgcagct tgctgtttgc ccactctatt tgcccagccc cagccctgga gagtcctta         180 gcagggcaaa gtgcaacata ggcagacctt aagggatgac tcagtaacag ataagctttg         240
```

-continued tgtgcctgca                                                                250

<210> SEQ ID NO 23
<211> LENGTH: 260
<212> TYPE: DNA
<213> ORGANISM: Artificial Sequence
<220> FEATURE:
<223> OTHER INFORMATION: CRM_LVR_132

<400> SEQUENCE: 23
agaatgaaca ttgaactttg gactatacct gaggggtgag gtaaacaaca ggactataaa      60
tggcccggga ggcgcccttt ggaccttttg caatcctggc gcactgaacc cttgacccct     120
gccctgcagc ccccgcagct tgctgtttgc ccactctatt tgcccagccc cagccctgga     180
gagtccttta gcagggcaaa gtgcaacata ggcagacctt aagggatgac tcagtaacag     240
ataagctttg tgtgcctgca                                                 260

<210> SEQ ID NO 24
<211> LENGTH: 366
<212> TYPE: DNA
<213> ORGANISM: Artificial Sequence
<220> FEATURE:
<223> OTHER INFORMATION: CRM_LVR_132_A1

<400> SEQUENCE: 24
aggttaattt ttaaaaagca gtcaaaagtc caagtggccc ttggcagcat ttactctctc      60
tgtttgctct ggttaataat ctcaggagca caaacattcc tgtaccagaa tgaacattga     120
actttggact atacctgagg ggtgaggtaa acaacaggac tataaatggc ccgggaggcg     180 cccctttggac cttttgcaat cctggcgcac tgaacccttg accctgccc tgcagccccc     240 gcagcttgct gtttgcccac tctatttgcc cagccccagc cctggagagt cctttagcag     300
ggcaaagtgc aacataggca gaccttaagg gatgactcag taacagataa gctttgtgtg     360
cctgca                                                                366

<210> SEQ ID NO 25
<211> LENGTH: 322
<212> TYPE: DNA
<213> ORGANISM: Artificial Sequence
<220> FEATURE:
<223> OTHER INFORMATION: CRM_LVR_132_V1

<400> SEQUENCE: 25
aagcaaatat ttgtggttat ggattaactc gaactgtttg cccactctat ttgccctgta      60
ccagaatgaa cattgaactt tggactatac ctgaggggtg aggtaaacaa caggactata     120
aatggcccgg gaggcgccct ttggaccttt tgcaatcctg cgcactgaa cccttgaccc     180 ctgccctgca gccccgcag cttgctgttt gcccactcta tttgcccagc cccagccctg     240
gagagtcctt tagcagggca aagtgcaaca taggcagacc ttaagggatg actcagtaac     300
agataagctt tgtgtgcctg ca                                              322

<210> SEQ ID NO 26
<211> LENGTH: 311
<212> TYPE: DNA
<213> ORGANISM: Artificial Sequence
<220> FEATURE:
<223> OTHER INFORMATION: CRM_LVR_132_V2

<400> SEQUENCE: 26

-continued

```
ggcgccctt tggacctttg caatcctgga gcaaacagca aacactgtac cagaatgaac      60
attgaacttt ggactatacc tgaggggtga ggtaaacaac aggactataa atggcccggg     120
aggcgcccct tggaccttt gcaatcctgg cgcactgaac ccttgacccc tgccctgcag     180 ccccgcagc ttgctgtttg cccactctat ttgcccagcc ccagccctgg agagtccttt     240
agcagggcaa agtgcaacat aggcagacct taagggatga ctcagtaaca gataagcttt     300
gtgtgcctgc a                                                         311
```

<210> SEQ ID NO 27
<211> LENGTH: 101
<212> TYPE: DNA
<213> ORGANISM: Artificial Sequence
<220> FEATURE:
<223> OTHER INFORMATION: CRM_LVR_133

<400> SEQUENCE: 27

```
agaatgaaca ttgaactttg gactatacct gaggggtgag gtaaacaaca ggactataaa      60
tggcccggga ggcgccctt ggaccttttg caatcctggc g                        101
```

<210> SEQ ID NO 28
<211> LENGTH: 207
<212> TYPE: DNA
<213> ORGANISM: Artificial Sequence
<220> FEATURE:
<223> OTHER INFORMATION: CRM_LVR_133_A1

<400> SEQUENCE: 28

```
aggttaattt ttaaaaagca gtcaaaagtc caagtggccc ttggcagcat ttactctctc      60
tgtttgctct ggttaataat ctcaggagca caaacattcc tgtaccagaa tgaacattga     120
actttggact atacctgagg ggtgaggtaa acaacaggac tataaatggc ccgggaggcg     180 cccttggac cttttgcaat cctggcg                                          207
```

<210> SEQ ID NO 29
<211> LENGTH: 163
<212> TYPE: DNA
<213> ORGANISM: Artificial Sequence
<220> FEATURE:
<223> OTHER INFORMATION: CRM_LVR_133_V1

<400> SEQUENCE: 29

```
aagcaaatat ttgtggttat ggattaactc gaactgtttg cccactctat ttgccctgta      60
ccagaatgaa cattgaactt tggactatac ctgaggggtg aggtaaacaa caggactata     120
aatggcccgg gaggcgccct ttggaccttt tgcaatcctg gcg                       163
```

<210> SEQ ID NO 30
<211> LENGTH: 152
<212> TYPE: DNA
<213> ORGANISM: Artificial Sequence
<220> FEATURE:
<223> OTHER INFORMATION: CRM_LVR_133_V2

<400> SEQUENCE: 30

```
ggcgccctt tggacctttg caatcctgga gcaaacagca aacactgtac cagaatgaac      60
attgaacttt ggactatacc tgaggggtga ggtaaacaac aggactataa atggcccggg     120
aggcgcccct tggaccttt gcaatcctgg cg                                    152
```

<210> SEQ ID NO 31
<211> LENGTH: 283

```
<212> TYPE: DNA
<213> ORGANISM: Artificial Sequence
<220> FEATURE:
<223> OTHER INFORMATION: LVR_127

<400> SEQUENCE: 31
agaatgaaca ttgaactttg gactatacct gaggggtgag gtaaacaaca ggactataaa      60
tggcccggga ggcgcccttt ggaccttttg caatcctggc gcactgaacc cttgacccct     120
gccctgcagc ccccgcagct tgctgtttgc ccactctatt tgcccagccc cagggacaga     180
gctgatcctt gaactcttaa gttccacggg catataaaac aggggcaagg cacagactca     240
tagcagagca atcaccacca agcctggaat aactgcagcc acc                       283

<210> SEQ ID NO 32
<211> LENGTH: 389
<212> TYPE: DNA
<213> ORGANISM: Artificial Sequence
<220> FEATURE:
<223> OTHER INFORMATION: LVR_127_A1

<400> SEQUENCE: 32
aggttaattt ttaaaaagca gtcaaaagtc caagtggccc ttggcagcat ttactctctc      60
tgtttgctct ggttaataat ctcaggagca caaacattcc tgtaccagaa tgaacattga     120
actttggact atacctgagg ggtgaggtaa acaacaggac tataaatggc ccggaggcg      180 ccctttggac cttttgcaat cctggcgcac tgaacccttg accctgccc tgcagccccc      240 gcagcttgct gtttgcccac tctatttgcc cagccccagg gacagagctg atccttgaac     300
tcttaagttc cacgggcata taaaacaggg gcaaggcaca gactcatagc agagcaatca     360
ccaccaagcc tggaataact gcagccacc                                       389

<210> SEQ ID NO 33
<211> LENGTH: 345
<212> TYPE: DNA
<213> ORGANISM: Artificial Sequence
<220> FEATURE:
<223> OTHER INFORMATION: LVR_127_V1

<400> SEQUENCE: 33
aagcaaatat ttgtggttat ggattaactc gaactgtttg cccactctat ttgccctgta      60
ccagaatgaa cattgaactt tggactatac ctgaggggtg aggtaaacaa caggactata     120
aatggcccgg gaggcgccct ttggaccttt tgcaatcctg gcgcactgaa cccttgaccc     180
ctgccctgca gccccgcag cttgctgttt gcccactcta tttgcccagc cccagggaca     240
gagctgatcc ttgaactctt aagttccacg ggcatataaa acaggggcaa ggcacagact     300
catagcagag caatcaccac caagcctgga ataactgcag ccacc                     345

<210> SEQ ID NO 34
<211> LENGTH: 334
<212> TYPE: DNA
<213> ORGANISM: Artificial Sequence
<220> FEATURE:
<223> OTHER INFORMATION: LVR_127_V2

<400> SEQUENCE: 34
ggcgcccttt ggaccttttg caatcctgga gcaaacagca aacactgtac cagaatgaac      60
attgaacttt ggactatacc tgaggggtga ggtaaacaac aggactataa atggcccggg     120
aggcgccctt tggaccttt gcaatcctgg cgcactgaac ccttgacccc tgccctgcag     180
```

-continued

```
cccccgcagc ttgctgtttg cccactctat ttgcccagcc ccagggacag agctgatcct     240
tgaactctta agttccacgg gcatataaaa caggggcaag gcacagactc atagcagagc     300
aatcaccacc aagcctggaa taactgcagc cacc                                  334

<210> SEQ ID NO 35
<211> LENGTH: 275
<212> TYPE: DNA
<213> ORGANISM: Artificial Sequence
<220> FEATURE:
<223> OTHER INFORMATION: LVR_131

<400> SEQUENCE: 35
ggcccgggag gcgccctttg dacctttttgc aatcctggcg cactgaaccc ttgacccctg      60
ccctgcagcc cccgcagctt gctgtttgcc cactctattt gcccagcccc agccctggag     120
agtcctttag cagggcaaag tgcaacatag gcagaccttag agggatgact cagtaacaga     180
taagctttgt gtgcctgcag ggcatataaa acaggggcaa ggcacagact catagcagag     240
caatcaccac caagcctgga ataactgcag ccacc                                  275

<210> SEQ ID NO 36
<211> LENGTH: 381
<212> TYPE: DNA
<213> ORGANISM: Artificial Sequence
<220> FEATURE:
<223> OTHER INFORMATION: LVR_131_A1

<400> SEQUENCE: 36
aggttaattt ttaaaaagca gtcaaaagtc caagtggccc ttggcagcat ttactctctc       60
tgtttgctct ggttaataat ctcaggagca caaacattcc tgtaccggcc cgggaggcgc      120
cctttggacc ttttgcaatc ctggcgcact gaacccttga ccctgccct gcagcccccg      180 cagcttgctg tttgcccact ctatttgccc agccccagcc ctggagagtc ctttagcagg     240
gcaaagtgca acataggcag accttaaggg atgactcagt aacagataag ctttgtgtgc     300
ctgcagggca tataaaacag gggcaaggca cagactcata gcagagcaat caccaccaag     360
cctggaataa ctgcagccac c                                                 381

<210> SEQ ID NO 37
<211> LENGTH: 337
<212> TYPE: DNA
<213> ORGANISM: Artificial Sequence
<220> FEATURE:
<223> OTHER INFORMATION: LVR_131_V1

<400> SEQUENCE: 37
aagcaaatat ttgtggttat ggattaactc gaactgtttg cccactctat ttgccctgta       60
ccggcccggg aggcgccctt tggacctttt gcaatcctgg cgcactgaac ccttgacccc      120
tgccctgcag cccccgcagc ttgctgtttg cccactctat ttgcccagcc ccagccctgg      180
agagtccttt agcagggcaa agtgcaacat aggcagacct taagggatga ctcagtaaca      240
gataagcttt gtgtgcctgc agggcatata aaacaggggc aaggcacaga ctcatagcag      300
agcaatcacc accaagcctg gaataactgc agccacc                                337

<210> SEQ ID NO 38
<211> LENGTH: 326
<212> TYPE: DNA
<213> ORGANISM: Artificial Sequence
<220> FEATURE:
<223> OTHER INFORMATION: LVR_131_V2
```

-continued

```
<400> SEQUENCE: 38 ggcgccctt ggacctttg caatcctgga gcaaacagca aacactgtac cggcccggga      60
ggcgcccttt ggacctttg caatcctggc gcactgaacc cttgacccct gccctgcagc     120
ccccgcagct tgctgtttgc ccactctatt tgcccagccc cagccctgga gagtccttta    180
gcagggcaaa gtgcaacata ggcagacctt aagggatgac tcagtaacag ataagctttg    240
tgtgcctgca gggcatataa aacaggggca aggcacagac tcatagcaga gcaatcacca    300
ccaagcctgg ataactgca gccacc                                         326

<210> SEQ ID NO 39
<211> LENGTH: 336
<212> TYPE: DNA
<213> ORGANISM: Artificial Sequence
<220> FEATURE:
<223> OTHER INFORMATION: LVR_132

<400> SEQUENCE: 39
agaatgaaca ttgaactttg gactatacct gaggggtgag gtaaacaaca ggactataaa     60
tggcccggga ggcgcccttt ggacctttg caatcctggc gcactgaacc cttgaccccct    120 gccctgcagc ccccgcagct tgctgtttgc ccactctatt tgcccagccc cagccctgga    180
gagtccttta gcagggcaaa gtgcaacata ggcagacctt aagggatgac tcagtaacag    240
ataagctttg tgtgcctgca gggcatataa aacaggggca aggcacagac tcatagcaga    300
gcaatcacca ccaagcctgg ataactgca gccacc                              336

<210> SEQ ID NO 40
<211> LENGTH: 442
<212> TYPE: DNA
<213> ORGANISM: Artificial Sequence
<220> FEATURE:
<223> OTHER INFORMATION: LVR_132_A1

<400> SEQUENCE: 40
aggttaattt ttaaaaagca gtcaaaagtc caagtggccc ttggcagcat ttactctctc     60
tgtttgctct ggttaataat ctcaggagca caaacattcc tgtaccagaa tgaacattga    120
actttggact atacctgagg ggtgaggtaa acaacaggac tataaatggc ccgggaggcg    180 cccttttggac cttttgcaat cctggcgcac tgaacccttg acccctgccc tgcagccccc    240
gcagcttgct gtttgcccac tctatttgcc cagccccagc cctggagagt cctttagcag    300
ggcaaagtgc aacataggca gaccttaagg gatgactcag taacagataa gctttgtgtg    360
cctgcagggc atataaaaca ggggcaaggc acagactcat agcagagcaa tcaccaccaa    420
gcctggaata actgcagcca cc                                            442

<210> SEQ ID NO 41
<211> LENGTH: 398
<212> TYPE: DNA
<213> ORGANISM: Artificial Sequence
<220> FEATURE:
<223> OTHER INFORMATION: LVR_132_V1

<400> SEQUENCE: 41
aagcaaatat ttgtggttat ggattaactc gaactgtttg cccactctat ttgccctgta     60
ccagaatgaa cattgaactt tggactatac ctgaggggtg aggtaaacaa caggactata    120
aatggcccgg gaggcgccct ttggaccttt tgcaatcctg gcgcactgaa cccttgaccc    180
```

-continued

```
ctgccctgca gcccccgcag cttgctgttt gcccactcta tttgcccagc cccagccctg      240
gagagtcctt tagcagggca aagtgcaaca taggcagacc ttaagggatg actcagtaac      300
agataagctt tgtgtgcctg cagggcatat aaaacagggg caaggcacag actcatagca      360
gagcaatcac caccaagcct ggaataactg cagccacc                              398

<210> SEQ ID NO 42
<211> LENGTH: 387
<212> TYPE: DNA
<213> ORGANISM: Artificial Sequence
<220> FEATURE:
<223> OTHER INFORMATION: LVR_132_V2

<400> SEQUENCE: 42
ggcgcccttt ggaccttttg caatcctgga gcaaacagca aacactgtac cagaatgaac       60
attgaacttt ggactatacc tgaggggtga ggtaaacaac aggactataa atggcccggg      120
aggcgcccct tggacctttt gcaatcctgg cgcactgaac ccttgacccc tgccctgcag      180
cccccgcagc ttgctgtttg cccactctat ttgcccagcc ccagccctgg agagtccttt      240
agcagggcaa agtgcaacat aggcagacct taagggatga ctcagtaaca gataagcttt      300
gtgtgcctgc agggcatata aaacaggggc aaggcacaga ctcatagcag agcaatcacc      360
accaagcctg gaataactgc agccacc                                        387

<210> SEQ ID NO 43
<211> LENGTH: 327
<212> TYPE: DNA
<213> ORGANISM: Artificial Sequence
<220> FEATURE:
<223> OTHER INFORMATION: LVR_133

<400> SEQUENCE: 43
agaatgaaca ttgaactttg gactatacct gaggggtgag gtaaacaaca ggactataaa       60
tggcccggga ggcgcccttt ggaccttttg caatcctggc gctcttttgt tttacatgaa      120
gggtctggca gccaaagcaa tcactcaaag ttcaaacctt atcatttttt gctttgttcc      180
tcttggcctt ggttttgtac atcagctttg aaaataccat cccagggtta atgctggggt      240
taatttataa ctaagagtgc tctagttttg caatacagga catgctataa aaatggaaag      300
atgttgcttt ctgagagatg cgccacc                                        327

<210> SEQ ID NO 44
<211> LENGTH: 433
<212> TYPE: DNA
<213> ORGANISM: Artificial Sequence
<220> FEATURE:
<223> OTHER INFORMATION: LVR_133_A1

<400> SEQUENCE: 44
aggttaattt ttaaaaagca gtcaaaagtc caagtggccc ttggcagcat ttactctctc       60
tgtttgctct ggttaataat ctcaggagca caaacattcc tgtaccagaa tgaacattga      120
actttggact atacctgagg ggtgaggtaa acaacaggac tataaatggc ccgggaggcg      180 cccctttggac cttttgcaat cctggcgctc ttttgtttta catgaagggt ctggcagcca      240
aagcaatcac tcaaagttca aaccttatca tttttttgctt tgttcctctt ggccttggtt      300
ttgtacatca gctttgaaaa taccatccca gggttaatgc tggggttaat ttataactaa      360
gagtgctcta gttttgcaat acaggacatg ctataaaaat ggaaagatgt tgctttctga      420
gagatgcgcc acc                                                       433
```

-continued

```
<210> SEQ ID NO 45
<211> LENGTH: 389
<212> TYPE: DNA
<213> ORGANISM: Artificial Sequence
<220> FEATURE:
<223> OTHER INFORMATION: LVR_133_V1

<400> SEQUENCE: 45
aagcaaatat ttgtggttat ggattaactc gaactgtttg cccactctat ttgccctgta        60
ccagaatgaa cattgaactt tggactatac ctgaggggtg aggtaaacaa caggactata       120
aatggcccgg gaggcgccct ttggaccttt tgcaatcctg gcgctctttt gttttacatg       180
aagggtctgg cagccaaagc aatcactcaa agttcaaacc ttatcatttt ttgctttgtt       240
cctcttggcc ttggttttgt acatcagctt tgaaaatacc atcccagggt taatgctggg       300
gttaatttat aactaagagt gctctagttt tgcaatacag gacatgctat aaaaatggaa       360
agatgttgct ttctgagaga tgcgccacc                                        389

<210> SEQ ID NO 46
<211> LENGTH: 378
<212> TYPE: DNA
<213> ORGANISM: Artificial Sequence
<220> FEATURE:
<223> OTHER INFORMATION: LVR_133_V2

<400> SEQUENCE: 46
ggcgcccttt ggaccttttg caatcctgga gcaaacagca aacactgtac cagaatgaac        60
attgaacttt ggactatacc tgaggggtga ggtaaacaac aggactataa atggcccggg       120
aggcgccctt tggacctttt gcaatcctgg cgctcttttg ttttacatga agggtctggc       180
agccaaagca atcactcaaa gttcaaacct tatcattttt tgctttgttc ctcttggcct       240
tggttttgta catcagcttt gaaaatacca tcccagggtt aatgctgggg ttaatttata       300
actaagagtg ctctagtttt gcaatacagg acatgctata aaaatggaaa gatgttgctt       360
tctgagagat gcgccacc                                                    378

<210> SEQ ID NO 47
<211> LENGTH: 558
<212> TYPE: DNA
<213> ORGANISM: Artificial Sequence
<220> FEATURE:
<223> OTHER INFORMATION: LP1

<400> SEQUENCE: 47
ccctaaaatg ggcaaacatt gcaagcagca aacagcaaac acacagccct ccctgcctgc        60
tgaccttgga gctggggcag aggtcagaga cctctctggg cccatgccac ctccaacatc       120
cactcgaccc cttggaattt cggtggagag gagcagaggt tgtcctggcg tggtttaggt       180
agtgtgagag gggaatgact cctttcggta agtgcagtgg aagctgtaca ctgcccaggc       240
aaagcgtccg ggcagcgtag gcgggcgact cagatcccag ccagtggact tagcccctgt       300
ttgctcctcc gataactggg gtgaccttgg ttaatattca ccagcagcct ccccgttgc       360 ccctctggat ccactgctta aatacggacg aggacagggc cctgtctcct cagcttcagg       420
caccaccact gacctgggac agtgaatccg gactctaagg taaatataaa atttttaagt       480
gtataatgtg ttaaactact gattctaatt gtttctctct tttagattcc aacctttgga       540
actgaattct agaccacc                                                    558
```

```
<210> SEQ ID NO 48
<211> LENGTH: 580
<212> TYPE: DNA
<213> ORGANISM: Artificial Sequence
<220> FEATURE:
<223> OTHER INFORMATION: CMV-IE

<400> SEQUENCE: 48
atagtaatca attacggggt cattagttca tagcccatat atggagttcc gcgttacata        60
acttacggta aatggcccgc ctggctgacc gcccaacgac ccccgcccat tgacgtcaat       120
aatgacgtat gttcccatag taacgccaat agggactttc cattgacgtc aatgggtgga       180
gtatttacgg taaactgccc acttggcagt acatcaagtg tatcatatgc caagtacgcc       240
ccctattgac gtcaatgacg gtaaatggcc cgcctggcat tatgcccagt acatgacctt       300
atgggacttt cctacttggc agtacatcta cgtattagtc atcgctatta ccatggtgat       360
gcggttttgg cagtacatca atgggcgtgg atagcggttt gactcacggg gatttccaag       420
tctccacccc attgacgtca atgggagttt gttttggcac caaaatcaac gggactttcc       480
aaaatgtcgt aacaactccg ccccattgac gcaaatgggc ggtaggcgtg tacggtggga       540
ggtctatata agcagagctg gtttagtgaa ccgtcagatc                              580

<210> SEQ ID NO 49
<211> LENGTH: 11
<212> TYPE: DNA
<213> ORGANISM: Artificial Sequence
<220> FEATURE:
<223> OTHER INFORMATION: HNF3 TFBS in V1

<400> SEQUENCE: 49
agcaaatatt t                                                              11

<210> SEQ ID NO 50
<211> LENGTH: 12
<212> TYPE: DNA
<213> ORGANISM: Artificial Sequence
<220> FEATURE:
<223> OTHER INFORMATION: HNF3 TFBS in V1

<400> SEQUENCE: 50
aaatatttgt gg                                                             12

<210> SEQ ID NO 51
<211> LENGTH: 15
<212> TYPE: DNA
<213> ORGANISM: Artificial Sequence
<220> FEATURE:
<223> OTHER INFORMATION: HNF1 TFBS in V1

<400> SEQUENCE: 51
ggttatggat taact                                                          15

<210> SEQ ID NO 52
<211> LENGTH: 10
<212> TYPE: DNA
<213> ORGANISM: Artificial Sequence
<220> FEATURE:
<223> OTHER INFORMATION: HNF3 TFBS in V1

<400> SEQUENCE: 52
ctgtttgccc                                                                10
```

-continued

```
<210> SEQ ID NO 53
<211> LENGTH: 10
<212> TYPE: DNA
<213> ORGANISM: Artificial Sequence
<220> FEATURE:
<223> OTHER INFORMATION: HNF3 TFBS in V1 and CRE0065

<400> SEQUENCE: 53
ctatttgccc                                                        10

<210> SEQ ID NO 54
<211> LENGTH: 13
<212> TYPE: DNA
<213> ORGANISM: Artificial Sequence
<220> FEATURE:
<223> OTHER INFORMATION: HNF4 TFBS in V2

<400> SEQUENCE: 54
cgccctttgg acc                                                    13

<210> SEQ ID NO 55
<211> LENGTH: 18
<212> TYPE: DNA
<213> ORGANISM: Artificial Sequence
<220> FEATURE:
<223> OTHER INFORMATION: c/EBP TFBS in V2

<400> SEQUENCE: 55
gaccttttgc aatcctgg                                               18

<210> SEQ ID NO 56
<211> LENGTH: 9
<212> TYPE: DNA
<213> ORGANISM: Artificial Sequence
<220> FEATURE:
<223> OTHER INFORMATION: HNF3 TFBS in V2

<400> SEQUENCE: 56 ctgtttgct                                                          9

<210> SEQ ID NO 57
<211> LENGTH: 10
<212> TYPE: DNA
<213> ORGANISM: Artificial Sequence
<220> FEATURE:
<223> OTHER INFORMATION: HNF3 TFBS in V2

<400> SEQUENCE: 57
gtgtttgctg                                                        10

<210> SEQ ID NO 58
<211> LENGTH: 19
<212> TYPE: DNA
<213> ORGANISM: Artificial Sequence
<220> FEATURE:
<223> OTHER INFORMATION: HNF4 binding site in CRE0074

<400> SEQUENCE: 58
aacattgaac tttggacta                                              19

<210> SEQ ID NO 59
<211> LENGTH: 8
<212> TYPE: DNA
<213> ORGANISM: Artificial Sequence
<220> FEATURE:
<223> OTHER INFORMATION: FoxO1a TFBS in CRE0074
```

-continued

<400> SEQUENCE: 59 gtaaacaa                                                                8

<210> SEQ ID NO 60
<211> LENGTH: 13
<212> TYPE: DNA
<213> ORGANISM: Artificial Sequence
<220> FEATURE:
<223> OTHER INFORMATION: HNF4 TFBS in CRE0058

<400> SEQUENCE: 60
cgccctttgg acc                                                         13

<210> SEQ ID NO 61
<211> LENGTH: 18
<212> TYPE: DNA
<213> ORGANISM: Artificial Sequence
<220> FEATURE:
<223> OTHER INFORMATION: c/EBP TFBS in CRE0058

<400> SEQUENCE: 61
gaccttttgc aatcctgg                                                    18

<210> SEQ ID NO 62
<211> LENGTH: 23
<212> TYPE: DNA
<213> ORGANISM: Artificial Sequence
<220> FEATURE:
<223> OTHER INFORMATION: RxR alpha TFBS in CRE0065 and CRE0065.1

<400> SEQUENCE: 62
actgaaccct tgacccctgc cct                                              23

<210> SEQ ID NO 63
<211> LENGTH: 10
<212> TYPE: DNA
<213> ORGANISM: Artificial Sequence
<220> FEATURE:
<223> OTHER INFORMATION: HNF3 TFBS in CRE0065 and CRE0065.1

<400> SEQUENCE: 63
ctgtttgccc                                                             10

<210> SEQ ID NO 64
<211> LENGTH: 15
<212> TYPE: DNA
<213> ORGANISM: Artificial Sequence
<220> FEATURE:
<223> OTHER INFORMATION: HNF4 TFBS in CRE0065.1

<400> SEQUENCE: 64
tgatccttga actct                                                       15

<210> SEQ ID NO 65
<211> LENGTH: 50
<212> TYPE: DNA
<213> ORGANISM: Artificial Sequence
<220> FEATURE:
<223> OTHER INFORMATION: functional variant of SEQ ID NO: 2
<220> FEATURE:
<221> NAME/KEY: misc_feature
<222> LOCATION: (29)..(29)
<223> OTHER INFORMATION: optional spacer sequence
<220> FEATURE:
<221> NAME/KEY: misc_feature
<222> LOCATION: (40)..(40)
<223> OTHER INFORMATION: optional spacer sequence

```
<400> SEQUENCE: 65
agcaaatatt tgtggttatg gattaactnc tgtttgcccn ctatttgccc              50

<210> SEQ ID NO 66
<211> LENGTH: 43
<212> TYPE: DNA
<213> ORGANISM: Artificial Sequence
<220> FEATURE:
<223> OTHER INFORMATION: functional variant of SEQ ID NO: 3

<400> SEQUENCE: 66
cgccctttgg accttttgca atcctggagc aaacagcaaa cac                    43

<210> SEQ ID NO 67
<211> LENGTH: 57
<212> TYPE: DNA
<213> ORGANISM: Artificial Sequence
<220> FEATURE:
<223> OTHER INFORMATION: functional variant of A1 (SEQ ID NO: 1)
<220> FEATURE:
<221> NAME/KEY: misc_feature
<222> LOCATION: (14)..(14)
<223> OTHER INFORMATION: optional spacer sequence
<220> FEATURE:
<221> NAME/KEY: misc_feature
<222> LOCATION: (26)..(26)
<223> OTHER INFORMATION: optional spacer sequence
<220> FEATURE:
<221> NAME/KEY: misc_feature
<222> LOCATION: (34)..(34)
<223> OTHER INFORMATION: optional spacer sequence
<220> FEATURE:
<221> NAME/KEY: misc_feature
<222> LOCATION: (50)..(50)
<223> OTHER INFORMATION: optional spacer sequence

<400> SEQUENCE: 67
gttaattttt aaangtggcc cttggntgtt tgcntggtta ataatctcan acaaaca      57

<210> SEQ ID NO 68
<211> LENGTH: 28
<212> TYPE: DNA
<213> ORGANISM: Artificial Sequence
<220> FEATURE:
<223> OTHER INFORMATION: the functional variant of LVR_CRE0074_SEPP1
<220> FEATURE:
<221> NAME/KEY: misc_feature
<222> LOCATION: (20)..(20)
<223> OTHER INFORMATION: optional spacer sequence

<400> SEQUENCE: 68
aacattgaac tttggactan gtaaacaa                                      28

<210> SEQ ID NO 69
<211> LENGTH: 28
<212> TYPE: DNA
<213> ORGANISM: Artificial Sequence
<220> FEATURE:
<223> OTHER INFORMATION: functional variant of LVR_CRE0058_APOB

<400> SEQUENCE: 69
gcgccctttg gaccttttgc aatcctgg                                      28

<210> SEQ ID NO 70
<211> LENGTH: 39
<212> TYPE: DNA
<213> ORGANISM: Artificial Sequence
<220> FEATURE:
```

-continued

```
<223> OTHER INFORMATION: functional variant of LVR_CRE0065_APOA1
<220> FEATURE:
<221> NAME/KEY: misc_feature
<222> LOCATION: (19)..(19)
<223> OTHER INFORMATION: optional spacer sequence
<220> FEATURE:
<221> NAME/KEY: misc_feature
<222> LOCATION: (30)..(30)
<223> OTHER INFORMATION: optional spacer sequence

<400> SEQUENCE: 70
actgaaccct tgacccctnc tgtttgcccn tatttgccc                            39

<210> SEQ ID NO 71
<211> LENGTH: 55
<212> TYPE: DNA
<213> ORGANISM: Artificial Sequence
<220> FEATURE:
<223> OTHER INFORMATION: functional variant of LVR_CRE0065_APOA1_v1
<220> FEATURE:
<221> NAME/KEY: misc_feature
<222> LOCATION: (19)..(19)
<223> OTHER INFORMATION: optional spacer sequence
<220> FEATURE:
<221> NAME/KEY: misc_feature
<222> LOCATION: (30)..(30)
<223> OTHER INFORMATION: optional spacer sequence
<220> FEATURE:
<221> NAME/KEY: misc_feature
<222> LOCATION: (40)..(40)
<223> OTHER INFORMATION: optional spacer sequence

<400> SEQUENCE: 71
actgaaccct tgacccctnc tgtttgcccn tatttgcccn tgatccttga actct         55

<210> SEQ ID NO 72
<211> LENGTH: 1775
<212> TYPE: DNA
<213> ORGANISM: Artificial Sequence
<220> FEATURE:
<223> OTHER INFORMATION: CBA

<400> SEQUENCE: 72
agatctgaat tcggtaccta gttattaata gtaatcaatt acggggtcat tagttcatag     60
cccatatatg gagttccgcg ttacataact tacggtaaat ggcccgcctg gctgaccgcc    120
caacgacccc cgcccattga cgtcaataat gacgtatgtt cccatagtaa cgccaatagg    180
gactttccat tgacgtcaat gggtggagta tttacggtaa actgcccact tggcagtaca    240
tcaagtgtat catatgccaa gtacgccccc tattgacgtc aatgacggta aatggcccgc    300
ctggcattat gcccagtaca tgaccttatg ggactttcct acttggcagt acatctacgt    360
attagtcatc gctattacca tggtcgaggt gagccccacg ttctgcttca ctctcccat     420 ctccccccc tccccacccc caatttttgta tttatttatt ttttaattat tttgtgcagc   480 gatggggggcg ggggggggg ggggcgcgc gccaggcggg gcggggcggg gcgaggggcg    540
gggcggggcg aggcggagag gtgcggcggc agccaatcag agcggcgcgc tccgaaagtt    600 tcctttttatg gcgaggcggc ggcggcggcg gccctataaa aagcgaagcg cgcggcgggc    660
gggagtcgct gcgcgctgcc ttcgccccgt gccccgctcc gccgccgcct cgcgccgccc    720
gccccggctc tgactgaccg cgttactccc acaggtgagc gggcgggacg gcccttctcc    780
tccgggctgt aattagcgct tggtttaatg acggcttgtt tcttttctgt ggctgcgtga    840
aagccttgag gggctccggg agggccctt gtgcggggggg agcggctcgg ggggtgcgtg    900
cgtgtgtgtg tgcgtgggga gcgccgcgtg cggctccgcg ctgcccggcg gctgtgagcg    960
```

-continued

```
ctgcgggcgc ggcgcggggc tttgtgcgct ccgcagtgtg cgcgaggggga gcgcggccgg      1020 gggcggtgcc ccgcggtgcg ggggggggctg cgagggggaac aaaggctgcg tgcggggtgt      1080
gtgcgtgggg gggtgagcag ggggtgtggg cgcgtcggtc gggctgcaac ccccctgca       1140 cccctctccc cgagttgctg agcacggccc ggcttcgggt gcggggctcc gtacggggcg      1200
tggcgcgggg ctcgccgtgc cgggcggggg gtggcggcag gtggggggtgc cgggcggggc      1260 ggggccgcct cgggccgggg agggctcggg ggaggggcgc ggcggccccc ggagcgccgg      1320
cggctgtcga ggcgcggcga gccgcagcca ttgcctttta tggtaatcgt gcgagagggc      1380
gcagggactt cctttgtccc aaatctgtgc ggagccgaaa tctgggaggc gccgccgcac      1440
cccctctagc gggcgcgggg cgaagcggtg cggcgccggc aggaaggaaa tgggcggggga      1500 gggccttcgt gcgtcgccgc gccgccgtcc ccttctccct ctccagcctc ggggctgtcc      1560
gcggggggac ggctgccttc ggggggggacg gggcagggcg gggttcggct tctggcgtgt      1620
gaccggcggc tctagagcct ctgctaacca tgttcatgcc ttcttctttt tcctacagct      1680
cctgggcaac gtgctggtta ttgtgctgtc tcatcatttt ggcaaagaat tcctcgaaga      1740
tctaggcaac gcgtctcgag gcggccgccg ccacc                                1775
```

```
<210> SEQ ID NO 73
<211> LENGTH: 26
<212> TYPE: DNA
<213> ORGANISM: Artificial Sequence
<220> FEATURE:
<223> OTHER INFORMATION: functional variant of LVR_CRE0066_NR1I2
<220> FEATURE:
<221> NAME/KEY: misc_feature
<222> LOCATION: (16)..(16)
<223> OTHER INFORMATION: optional spacer sequence

<400> SEQUENCE: 73
gcagggcaaa gtgcangatg actcag                                             26

<210> SEQ ID NO 74
<211> LENGTH: 13
<212> TYPE: DNA
<213> ORGANISM: Artificial Sequence
<220> FEATURE:
<223> OTHER INFORMATION: HNF1 TFBS in CRE0051

<400> SEQUENCE: 74
gttaattttt aaa                                                           13

<210> SEQ ID NO 75
<211> LENGTH: 11
<212> TYPE: DNA
<213> ORGANISM: Artificial Sequence
<220> FEATURE:
<223> OTHER INFORMATION: HNF4 TFBS in CRE0051

<400> SEQUENCE: 75
gtggcccttg g                                                             11

<210> SEQ ID NO 76
<211> LENGTH: 7
<212> TYPE: DNA
<213> ORGANISM: Artificial Sequence
<220> FEATURE:
<223> OTHER INFORMATION: HNF3 TFBS in CRE0051

<400> SEQUENCE: 76
``` tgtttgc                                                                                                  7

<210> SEQ ID NO 77
<211> LENGTH: 15
<212> TYPE: DNA
<213> ORGANISM: Artificial Sequence
<220> FEATURE:
<223> OTHER INFORMATION: HNF1 TFBS in CRE0051

<400> SEQUENCE: 77
tggttaataa tctca                                                                                         15

<210> SEQ ID NO 78
<211> LENGTH: 7
<212> TYPE: DNA
<213> ORGANISM: Artificial Sequence
<220> FEATURE:
<223> OTHER INFORMATION: HNF3 TFBS in CRE0051

<400> SEQUENCE: 78 acaaaca                                                                                                  7

<210> SEQ ID NO 79
<211> LENGTH: 15
<212> TYPE: DNA
<213> ORGANISM: Artificial Sequence
<220> FEATURE:
<223> OTHER INFORMATION: HNF4G TFBS in CRE0066

<400> SEQUENCE: 79
gcagggcaaa gtgca                                                                                         15

<210> SEQ ID NO 80
<211> LENGTH: 10
<212> TYPE: DNA
<213> ORGANISM: Artificial Sequence
<220> FEATURE:
<223> OTHER INFORMATION: FOS::JUN TFBS in CRE0066

<400> SEQUENCE: 80
gatgactcag                                                                                               10

<210> SEQ ID NO 81
<211> LENGTH: 58
<212> TYPE: DNA
<213> ORGANISM: Artificial Sequence
<220> FEATURE:
<223> OTHER INFORMATION: sequence not comprised in CRM/liver-specific
      promoter

<400> SEQUENCE: 81
ggacttagcc cctgtttgct cctccgataa ctggggtgac cttggttaat attcacca          58

<210> SEQ ID NO 82
<211> LENGTH: 51
<212> TYPE: DNA
<213> ORGANISM: Artificial Sequence
<220> FEATURE:
<223> OTHER INFORMATION: sequence not comprised in CRM/liver-specific
      promoter

<400> SEQUENCE: 82
gcccctgttt gctcctccga taactggggt gaccttggtt aatattcacc a                 51

<210> SEQ ID NO 83
<211> LENGTH: 890

-continued

```
<212> TYPE: DNA
<213> ORGANISM: Artificial Sequence
<220> FEATURE:
<223> OTHER INFORMATION: TBG

<400> SEQUENCE: 83
aggttaattt ttaaaaagca gtcaaaagtc caagtggccc ttggcagcat ttactctctc      60
tgtttgctct ggttaataat ctcaggagca caaacattcc agatccaggt taatttttaa     120
aaagcagtca aaagtccaag tggcccttgg cagcatttac tctctctgtt tgctctggtt     180
aataatctca ggagcacaaa cattccagat ccggcgcgcc agggctggaa gctacctttg     240
acatcatttc ctctgcgaat gcatgtataa tttctacaga acctattaga aaggatcacc     300
cagcctctgc ttttgtacaa ctttcccta aaaaactgcc aattccactg ctgtttggcc      360
caatagtgag aactttttcc tgctgcctct tggtgctttt gcctatggcc cctattctgc     420
ctgctgaaga cactcttgcc agcatggact taaacccctc cagctctgac aatcctcttt     480
ctcttttgtt ttacatgaag ggtctggcag ccaaagcaat cactcaaagt tcaaaccta     540 tcatttttg ctttgttcct cttggccttg gttttgtaca tcagctttga aaataccatc      600
ccagggttaa tgctggggtt aatttataac taagagtgct ctagttttgc aatacaggac     660
atgctataaa aatggaaaga tgttgctttc tgagagactg cagaagttgg tcgtgaggca     720
ctgggcaggt aagtatcaag gttacaagac aggtttaagg agaccaatag aaactgggct     780
tgtcgagaca gagaagactc ttgcgtttct gataggcacc tattggtctt actgacatcc     840
actttgcctt tctctccaca gggcaatccg gtactgttgg taaagccacc               890
```